(12) United States Patent
Gonzalez

(10) Patent No.: US 8,906,355 B2
(45) Date of Patent: Dec. 9, 2014

(54) SYNTHETIC STEREOISOMER PEPTIDES IN THE RETRO-INVERSO AND INVERSO CONFIGURATION, AND WITH CYCLIC AND LINEAR STRUCTURE, THEIR POLYMER CONJUGATES, THEIR ENCAPSULATION IN POLYMER PARTICLES, AND USES THEREOF

(71) Applicant: Lucia Irene Gonzalez, Baltimore, MD (US)

(72) Inventor: Lucia Irene Gonzalez, Baltimore, MD (US)

(*) Notice: Subject to any disclaimer, the term of this patent is extended or adjusted under 35 U.S.C. 154(b) by 0 days.

(21) Appl. No.: 13/732,951

(22) Filed: Jan. 2, 2013

(65) Prior Publication Data
US 2013/0156723 A1 Jun. 20, 2013

Related U.S. Application Data

(63) Continuation-in-part of application No. 12/914,050, filed on Oct. 28, 2010, which is a continuation-in-part of application No. PCT/US2010/054583, filed on Oct. 28, 2010.

(60) Provisional application No. 61/582,989, filed on Jan. 4, 2012, provisional application No. 61/256,260, filed on Oct. 29, 2009.

(51) Int. Cl.
| | |
|---|---|
| A61K 31/74 | (2006.01) |
| A61K 47/48 | (2006.01) |
| C08G 63/48 | (2006.01) |
| C08G 63/91 | (2006.01) |
| C08L 89/00 | (2006.01) |
| C07K 17/08 | (2006.01) |
| C08F 222/38 | (2006.01) |
| C07K 7/64 | (2006.01) |
| C12N 9/96 | (2006.01) |
| C07K 7/06 | (2006.01) |
| C07K 7/08 | (2006.01) |
| A61K 38/00 | (2006.01) |

(52) U.S. Cl.
CPC .............. *C08G 63/912* (2013.01); *A61K 38/00* (2013.01); *C07K 17/08* (2013.01); *C08F 222/38* (2013.01); *C07K 7/64* (2013.01); *C12N 9/96* (2013.01); *C07K 7/06* (2013.01); *A61K 47/482* (2013.01); *A61K 47/48176* (2013.01); *C07K 2319/33* (2013.01); *C07K 7/08* (2013.01)
USPC ...................... 424/78.27; 424/78.17; 525/54.1

(58) Field of Classification Search
CPC ........ A61K 38/00; C08G 63/912; C08F 22/38
See application file for complete search history.

(56) References Cited

U.S. PATENT DOCUMENTS 7,192,921 B2 * 3/2007 Laakkonen et al. .......... 530/317

FOREIGN PATENT DOCUMENTS

WO WO 03040693 A2 * 5/2003

OTHER PUBLICATIONS

Nori A "Design, synthesis and evaluation of HPMA copolymer-Tat conjugates as potential carriers for drug delivery" Doctoral Dissertation. Published May 2009.*
Kopecek J and Kopeckova P "HPMA coplymers: Origins, early developments, present, and future" Adv Drug Deliv Rev 62:122-149. Published Feb. 17, 2010.*
Weide et al "Spatial Screening for the Identification of the Bioactive Conformation of Integrin Ligands" Top Curr Chem 272:1-50. Published online Jul. 22, 2006.*

* cited by examiner

*Primary Examiner* — Maury Audet
*Assistant Examiner* — Zachary J Miknis

(57) ABSTRACT

This invention discloses ligand-targeted multi-stereoisomer peptide-polymer conjugate compounds comprising a plurality of different synthetic and chemically modified stereoisomer peptides that have been conjugated to a biocompatible polymer carrying a peptide ligand for targeted delivery or encapsulated in ligand targeted polymer nanoparticles. The unique physicochemical properties of the stereoisomer peptides provide therapeutic compounds with ideal biopharmaceutical properties. The stereoisomer peptides carried by the polymer are delivered to cells or tissues to inhibit, suppress, block, or disrupt, simultaneously and independently, the functional domain of a different disease causing protein. Therefore the compounds are useful therapeutics for the treatment of abnormal angiogenesis and inflammation which are the hall mark of most human diseases including but not limited to cancer, metastasis, pathological conditions of the eye, cardiovascular, brain, and neurodegenerative disorders, diabetes, and diseases caused by infectious microorganisms.

9 Claims, 5 Drawing Sheets

Cyclic D-peptide with disulfide bond

Cyclic D-peptide with peptide (terminal residues) or lactam (terminal side chain residues) bond (i.e., amide bond)

Cyclic D-peptide with disulfide bond adjacent to a motif of interest

Cyclic D-peptide with lactam bond adjacent to a motif of interest

Where: X1, 2, 3, ....etc. = amino acid residue and X-Y-Y-X = sequence motif

PLGA - Peptide- Ligand nanoparticles loaded with different PLGA- stereoisomer peptides Conjugation of a stereoisomer peptide or a peptide ligand to activated PLGA by amide bond formation Diagram representing a ligand-targetd multi-stereoisomer peptide-HPMA conjugate compound

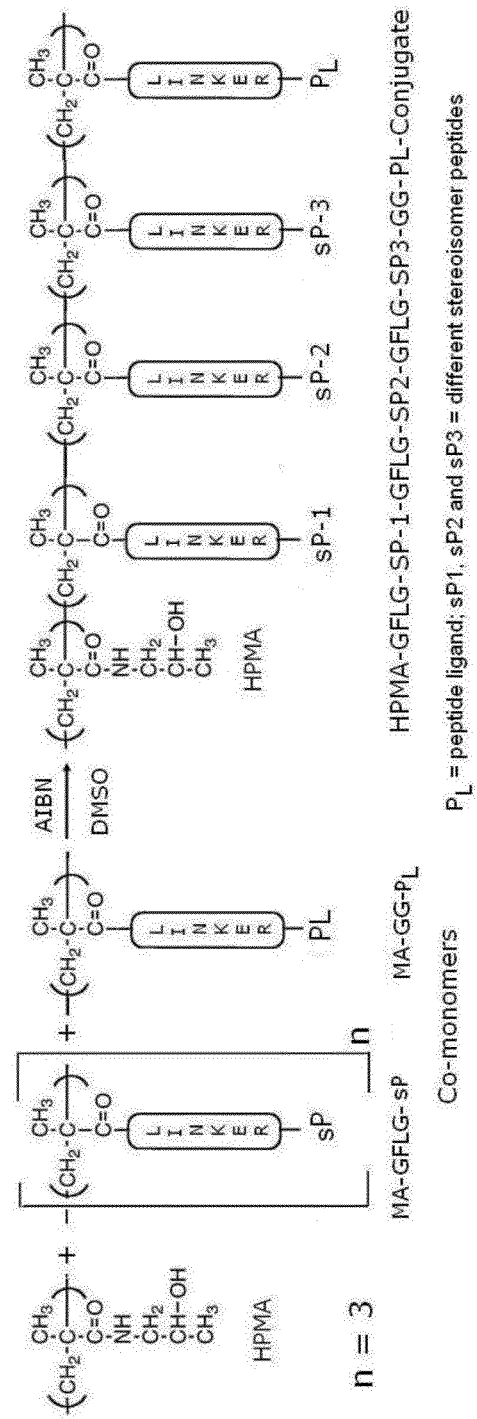

SYNTHETIC STEREOISOMER PEPTIDES IN THE RETRO-INVERSO AND INVERSO CONFIGURATION, AND WITH CYCLIC AND LINEAR STRUCTURE, THEIR POLYMER CONJUGATES, THEIR ENCAPSULATION IN POLYMER PARTICLES, AND USES THEREOF

RELATED APPLICATIONS

This application claims priority to U.S. Provisional Application No. 61/582,989, filed on Jan. 4, 2012. This application is also a continuation in part of U.S. application Ser. No. 12/914,050, filed Oct. 28, 2010 which claims priority to U.S. Provisional Application No. 61/256, 260, filed Oct. 29, 2009. This application is also a continuation in part of PCT Application No. PCT/US2010/054583, filed Oct. 28, 2010, which claims priority to U.S. Provisional Application No. 61/256, 260, filed Oct. 29, 2009. Each of these applications is incorporated herein by reference in its entirety.

TECHNICAL FIELD

This invention, relates to therapeutic compounds comprising a plurality of different synthetic and chemically modified stereoisomer peptides in retro-inverso and inverso configuration and with linear or cyclic constrained structure that are conjugated to a polymer carrying a peptide-ligand or encapsulated in ligand targeted polymer nanoparticles to create novel and unique ligand-targeted multi-stereoisomer peptide polymer conjugate compounds, and uses thereof for the treatment of a plurality of mammalian diseases induced by abnormal angiogenesis and inflammation caused by the abnormal activation of a variety of proteins in the body or proteins from infectious microorganisms.

Incorporated by reference herein in its entirety is the Sequence Listing entitled "Sequence_Listing_ST25.txt."

BACKGROUND

The following description provides a summary of information relevant to present disclosure and is not a concession that any of the information provided or publications referenced herein is prior art to the presently claimed invention.

Angiogenesis is the growth of new blood vessels from existing ones, and it is an important biological process for tissue development, growth, and repair. Angiogenesis is also an integral component of many physiological and pathological conditions such as wound healing, inflammation, and tumor growth (Folkman, J. and Klagsbrun, M. 1987. Science, 235: 442-447). Under abnormal conditions, angiogenesis can either directly or indirectly cause a particular disease that may include cancer, solid tumors, metastasis, diabetes, inflammation, cardiovascular disease, rheumatoid arthritis, psoriasis, inflammatory diseases, and Alzheimer's and Parkinson's diseases, and related neurological disease conditions, brain disorders, neurodegenerative disorders, neuropsychiatric illnesses, bipolar disorder, and diseases caused by aging. Angiogenesis may also exacerbate an existing pathological condition leading to other diseases, including eye retinopathies such as wet age-related macular degeneration, choroidal neovascularization, diabetic retinopathy, diabetic macular edema, retinal vein occlusion, and retinal angiomatus. These angiogenesis-dependent diseases are the result of new blood vessels growing excessively. In these conditions, new blood vessels feed diseased tissues and destroy normal tissues, and in the case of cancer, the new vessels allow tumor cells to grow and establish solid tumors or to escape into the circulation and lodge in other organs leading to tumor metastases.

There is considerable evidence showing that angiogenesis and chronic inflammation are closely related; the nature of this link involves both a considerable increase of cellular infiltration and proliferation, and the intervention of many growth factors and cytokines with overlapping activities (Jackson, J R et al. 1997, FASEB J, 11:457-465). Thus, targeting abnormal angiogenesis is important for the treatment of inflammation which is at the root of all chronic illnesses including but not limited to cancer, eye pathologies, diabetes, obesity, arthrosclerosis, reumathoid arthritis, heart, metabolic, skin, and brain diseases disorders, Alzheimer's, Parkinson's, Crohn's, pulmonary and bowel disease, dementia, depression, bipolar disorders, autism, to name a few. Inflammation, therefore, is a complex biological response of the vascular tissues (angiogenesis) to harmful stimuli such as cell damage, infections by pathogens, physical injuries, toxicants, irritants, foreign debris, burns, stress, and trauma.

Inflammation is a process by which the body's white blood cells and chemicals protect the body from infection and foreign substances such as bacteria and viruses. Inflammation can be acute or chronic. Acute inflammation is the initial response of the body to harmful stimuli and involves the vascular system, the immune system, the movement of blood cells and local cells into the injured tissues along with a cascade of biological events. When inflammation persists becomes chronic. There is stimulation of pro-inflammatory immune cells when they are not needed causing progressive damage to the cells and tissues (e.g., pancreatic tissues, gut mucosa, blood vessel lining, and joint tissue, to name a few) at the site of inflammation leading to a variety of diseases.

Many pro-angiogenic factors are mediators of inflammation (Campa et al. 2010, ID 546826, 1-14), and in some diseases, the body's immune system inappropriately triggers an inflammatory response when there are no foreign substances to fight off; in these autoimmune diseases, the body's normally protective immune system causes damage to its own tissues. Multiple sclerosis, type 1 diabetes mellitus, thyroiditis, rheumatoid arthritis, and lupus are autoimmune diseases. Thus, it is reasonable to deduce that most human diseases are inflammatory, and that this is mainly due to abnormal angiogenesis, defined as the uncontrolled growth of new blood vessels induced by the abnormal balance of many proteins involved in different cellular signaling pathways and biochemical functions in the body.

Numerous studies have demonstrated the direct association of abnormal angiogenesis, chronic inflammation and many human diseases. For example, inflammation triggered by microbes is a protective response against pathogens; however, it causes secondary damage to host tissues, i.e., DNA damage in various cell types resulting in carcinogenesis. Such inflammatory response induced by chronic infections with pathogens trigger liver, colorectal, and cervical cancers, and lymphoma (Kipanyula, M J. et al. 2012. Cell Signal, October 30. doi:pii: 50898-6568(12)00294-X. 10.1016/j.cellsig.2012.10.014). Therefore, chronic inflammation is a high risk for many cancers, including pancreatic cancer. For example, proteins such as nitric oxide synthase (iNOS) and cyclooxygenase-2 (COX-2) are over-expressed in pancreatic cancer tissues; hyperlipidemia, obesity, and type II diabetes are also associated with chronic inflammation in the pancreas and involved in pancreatic cancer development (Takahashi M, et al. 2012. Semin Immunopathol. September 7 [Epub ahead of print]). It is clear from the examples that abnormal angiogenesis and inflammation play important roles in the pathogenesis of diseases.

Diseases of the eye are also closely related to angiogenesis and inflammation. Although there is not known lymphatic system in the eye, evidence from research studies have shown that the eye and their different surrounding tissues also have several lymphatic channels. Thus, both lymphangiogenesis and inflammation play important roles in pathological conditions in the eye including corneal transplant rejection, ocular tumor progression, macular edema, macular degeneration, choroidal neovascularization, among other abnormal conditions (Nakao S. et al. 2012, J. Ophthalmology. Article ID 783163, 11 pages doi: 10.1155/2012/783163).

The central nervous system (CNS) tissues, including the brain, the eye, and the spinal cord are protected from the circulation by a complex of biological barriers, and covered with a myeloid cell population known as microglia. When the CNS is damaged by acute insults, neurodegenerative conditions, and psychiatric disorders, there is an impairment of mechanisms such as neurogenesis and angiogenesis. This vascular dysfunction leads to cerebrovascular disorders, which cause neuropathological changes in the brain leading for example to dementia (e.g., Alzheimer's disease). Thus, cerebrovascular disease and microvascular alterations seem to interact with the underlying brain pathology, affecting the progression of cognitive deficits and encompassing changes in virtually all cell types of the neurovascular unit, including endothelial cells, vascular smooth muscle cells, pericytes, and astrocytes (Pimentel-Coelho P M and Rivest S. 2012. Eur J. Neurosci., 35(12):1917-37; Grammas P. et al, 2011. Int J Clin Exp Pathol. 15; 4(6):616-27).

Growth factors are capable of stimulating cellular growth, proliferation, and cellular differentiation and are involved in most cancers. They are important for regulating a variety of cellular processes and act as signaling molecules between cells (Welsh et al. Amer. J. Surg. 194, 2007, S76-S83). Excessive angiogenesis occurs when diseased cells produce abnormal amounts of growth factors or pro-angiogenic factors, overwhelming the effects of natural angiogenesis inhibitors. Pro-angiogenic growth factors include vascular endothelial growth factor (VEGF-A, B and C), fibroblast growth factor (bFGF), platelet-derived growth factor (PDGF-a/b), epidermal growth factor (EGF), proepithelin (PEPI) or PC cell-derived growth factor (PCDGF) among many others (Marjon P L et al. Molecular Cancer 2004, 3:1-12; Kwabi-Addo B et al. Endocr Relat Cancer. 2004 11(4):709-24).

Cancer is caused by over-expression, and up-regulation of proteins (i.e., growth factors) implicated in many physiological pathways and endocrine functions, as well as the dysfunction of proteins that suppress cancer (i.e., p53) by interacting with other proteins (i.e., MDM2). When these cellular proteins become disfunctional, abnormal cells divide without control, and migrate and spread to any tissue through the blood and lymph systems (Hanahan D, Weinberg R A. 2000, Cell, 100(1):57-70) causing cancer. The most common cancers include breast, colon, pancreas, prostate, blood, bladder, brain, blood, bone, kidney, lung, liver, skin, ovarian, thyroid, gastrointestinal, head and neck, and neural, among others (Jemal et al. CA Cancer J. Clin. 2008, 58(2):71-96). Progress in cancer research has been slow since the drugs are mainly palliative and do not cure cancer; hence, there is a persisting need to develop effective therapeutic compounds that are more stable, more potent, with minimum or no toxicity, and that prolong the life of patients while providing significant improvement in their quality of life (QOL).

Pathological conditions of the eye include age-related macular degeneration, choroidal neovascularization, (AMD), proliferative diabetic retinopathy (PDR), diabetic macular edema (DME), among others. These diseases are the result of aberrant proliferation of new blood microvessels or neoangiogenesis (Hubschman et al. Clinical Ophthalmology 2009, 3 167-174). VEGF is a major factor in neovascular eye diseases and is the target of several anti-VEGF therapies based on monoclonal antibodies. Unfortunately, such therapies induce considerably side effects; thus, effective therapies are an unmet medical need.

Receptors, found in the extra cellular matrix, are transmembrane proteins that bind ligands. Integrins are receptors for a variety of extra cellular matrix proteins mediating migration of endothelial cells, and regulating their growth, survival, and differentiation, but there are also present on tumor cells of various origins (Cox et al, Nat Rev Drug Discov. 2010, 9(10):804-20). Receptors involved in human diseases include but are not limited to VEGF receptors, G protein receptors, ERBB receptors, platelet derived growth factor receptor (PDGFR), CXR1, CXR2, CCR3, CCR5 receptors, and NOGO receptors. Neurodegenerative diseases and mood disorders are example of diseases caused by the unbalanced neurotransmission of receptors and structural impairment of neuroplasticity. Chronic stress causes decrease of neurotrophin levels inducing depression. Antidepressants like lithium help increase expression of neurotrophins like BDNF and VEGF, thereby blocking, or reversing structural and functional pathologies via neurogenesis. Lithium also induces mood stabilization and neurogenesis due to the inhibition of glycogen synthase kinase-3beta (GSK-3beta), which allows the accumulation of beta-catenin. Increased levels of GSK-3beta and beta-catenin are associated with various neuropsychiatric and neurodegenerative diseases (Wada A. J Pharmacol Sci 2009, 110, 14-28). Thus, inhibition of GSK-3 beta expression seems therefore beneficial to ameliorate and/or stabilize mood disorders and induce neurogenesis.

The unbalanced presence of receptors also causes neurodegeneration. The Nogo receptor binds to the myelin-associated proteins Nogo-A, MAG, and OMgp, causing neurodegeneration. It can inhibit differentiation, migration, and neurite outgrowth of neurons, causing poor recovery of the adult central nervous system (CNS) from damage. Brain-derived neurotrophic factor stimulates the phosphorylation, suppressing Nogo-dependent inhibition of neurite outgrowth from neuroblastoma-derived neural cells; thus, it is important to control Nogo signaling to prevent neuronal damage.

Some proteins in the human body when suppressed exert a positive or beneficial effect. The target of rapamycin, mTOR, when inhibited suppresses the overexpression of HER2 oncoprotein, which is involved in cancer, or inhibits the process of aging by extending the lifespan of organisms (e.g., worms, fruit fly, yeast, and mice); mTOR, is therefore a suitable target to create potential anti-cancer and anti-aging compounds (Liu et al. Nature Reviews Drug Discovery 2009, 8:627-644). Other negative regulators of angiogenesis include thrombospondin-1, brain derived antiangiogenesis inhibitor, tumnstatin, angiostatin, somatostatin, tropomyosin, and endostatin among others. These proteins inhibit endothelial cell proliferation and tumor angiogenesis in vivo.

Diseases caused by pathogen agents include those acquired by blood borne pathogens like viruses (e.g., HIV, HCV, HBV, HSV, HTLV among others) through blood via infected people or animals, blood transfusions, or sexual contact. HIV/AIDS is a worldwide disease of large proportions (Richman, et al. Science 2009, 323, 1304-1307); yet there is no cure in spite of nearly four decades of basic and vaccine research.

Diseases caused by infectious agents include those caused by prions, which induce their own replication and derive from self; those caused by parasites (e.g., malaria, TB) acquired through bites by host organisms (e.g., insects, rodents), and those caused by pathogens acquired by contaminated food or water, or open wounds (e.g., bacteria, fungi, yeast).

Prions contain a protein (PrP) 27-30, which aggregates forming amyloid plaques that accumulate selectively in the central nervous system cells causing neurodegenerative diseases such as Creuzfeldt-Jakob and Alzheimer's diseases, Down's syndrome, fatal familial insomnia, and Parkinson's Disease. Prions are transmitted through contaminated plasma products, meat, and feeds or by person to person (Gu et al. JBC 2002, 277(3):2275-228). There are no drugs to treat prion infection, hence the need to develop novel drugs for this disease.

Bacterial and parasitic infections are a worldwide health problem. *Staphylococcus aureus* (MRSA) is a highly infectious bacteria and the cause of worldwide nosocomial infections. (Kaufmann et al., Exper. Opin. Biol. Ther. 2008, 8(6): 719-724). Tuberculosis, caused by the pathogenic bacteria *Mycobacterium tuberculosis* (Mtb), is presently the leading cause of death from infectious disease, infecting more than a third of the world's population (Ciulli et al. Chem Bio Chem 2008, 9, 2606-2611). It is acquired from small-infected mammals or by person to person. *Salmonella typhimurium*, other highly infectious and deadly bacteria, spreads by drinking contaminated water (Townes et al. Biochemical and Biophysical Research Communications 2009, 387: 500-503). Malaria, caused by the protozoan *Plasmodium falciparum*, is spread by mosquito bites infecting the red blood cells (Van-Buskirk et al. PNAS, 2009, 106(31):13004-13009).

The diseases described above are the result of the abnormal balance of many proteins involved in different functions and physiological pathways in the body. Thus, it is clear that many different signaling proteins and biochemical pathways are involved in abnormal angiogenesis and chronic inflammation and many proteins that are abnormally over-expressed or down-regulated trigger such abnormal angiogenesis and inflammation. Drugs approved to treat many of these diseases are single target drugs that provide a modest and transient clinical effect, but do not cure the aimed disease, and most are non-specific. Furthermore, clinical trials of drugs targeting many of these diseases have shown numerous times that targeting a single protein or an angiogenesis pathway or a single mechanism, or a single disease condition, is unlikely to result in the best possible benefit for the patient; clinical trials with combination therapies, for cancer, (i.e., chemo, radiation, and antibodies), or HIV (HAART), to name a few, have proven unsuccessful since none of these approaches cure either cancer or HIV infection. Therefore, there is an urgent and persisting need to develop novel and unique multi-targeted therapies.

It would be therefore advantageous to create therapeutic compounds carrying a plurality of different synthetic stereoisomer peptides in their retro-inverso or inverso and linear and cyclic configuration for the purpose of simultaneously and independently targeting different pathologic proteins involved in a disease. This approach may allow simultaneous interference at different levels in the biochemical cascade, or interference of different cellular pathways that lead to disease when proteins are abnormally over-expressed or down regulated. For example, targeting simultaneously several proteins involved in abnormal angiogenesis and inflammation would enable therapeutic applications for cancer, eye pathologies, brain diseases, neurological diseases, diabetes, cardiovascular diseases, arthritis, infectious diseases, psoriasis, Alzheimer's and Parkinson's diseases, diabetes, bipolar disorders, among many others.

Accordingly, there is need to create novel and unique compounds by searching, finding, integrating, converging, modifying, and applying existing knowledge and technologies. This invention precisely follows such approach to create for the first time novel and unique ligand-targeted multi-stereoisomer peptide-polymer conjugate compounds that can be used as therapeutics for the treatment of a variety of human diseases. The particular medical application of a therapeutic compound created in this invention, will depend on the plurality of specific and unique stereoisomer peptides comprised in the polymer conjugate.

A variety of methods described in the literature to synthesize peptides, are aimed at improving, modifying or providing alternative approaches for their synthesis, and for the terminal groups protection, and coupling that can be applied depending on the structure of the peptide to be synthesized, and the conformation. Such peptide synthesis methods are well known to those of skill in the art (see Stewart J M and Young J D, 1984, Solid phase peptide synthesis (2nd ed.). Rockford, Pierce Chemical Company; Atherton E and Sheppard R C, 1989, Solid Phase peptide synthesis: a practical approach. Oxford, England: IRL Press; and Henklein et al, 2008, J. Peptide Science 14 (8): P10401-104; Greene's Protective Groups in Organic Synthesis, 4th ed., John Wiley & Sons, Inc., 2007). Methods for synthesizing retroinverso peptides, which are similar to their L-counterparts, may also vary depending on the sequence of the stereoisomer peptide, their configuration and structure (see Briand et al. 1997, PNAS 94:12545-50, and Venkataramanarao et al. 2006, Tetrahedron Letters 47: 9139-9141). However, none of these methods provide any detail as to how synthesize, and chemically modify the stereoisomer peptides of this invention.

Cyclization of stereoisomer peptides to create cyclo peptides is an important feature of this invention. Peptides containing several Cys residues in the core of the peptide or at the ends of each side of a linear peptide form disulfide bonds which are achieved by using a variety of oxidation reactions. Similarly, methods of peptide cyclization that do not form disulfide bonds but rather create other type of bonds through linking of the terminal residues of the peptide, or the side chains of residues in the peptide, are also available, and are known to those of skill in the art (see Methods of cyclization are described by Bulaj G and Olivera B M, 2008, Antioxid Redox Signal, 10(1):141-55, and Amit M et al, 2009. Biochemistry, 48 (15):3288-3303). However, none of these methods describe the actual cyclization of stereoisomer peptides, with D-amino acids, and in the retroinverso or inverso configuration. Hence, there is the need to make modifications to create ands describe procedures that include the stereoisomer peptides of this invention.

To be able to effectively deliver drugs inside tissues or cells, a variety of polymers such as PLGA, PCL, HPMA, PEG, have been used because they produce tailored surface properties with specific physical, chemical, and biological properties that are suitable for medical applications. However, the selective delivery of therapeutic agents by polymers to disease tissue or cells in vivo remains a major challenge since it depends on the particular physicochemical properties of the polymer and the drug (see Zhang, Y and Chu C C. 2002, J. Biomater. Appl. 16: 305-325, and Liu J et al., 2004, J. Pharm. Sci. 93: 132-143) and the biological pathway for delivery (see Qaddoumi M G et al. 2003. Mol. Vis., 9: 559-568). In spite of this complexity, polymers have been used in a variety of medical and biotechnological applications for controlled delivery of small molecules (mainly cytotoxic) and large biomolecules (proteins and antibodies) inside tissues or cells (see Jeong B et al. 1997, Nature 388: 860-862; Bae Y H et al. 1997. Ann. N.Y. Acad. Sci. 831: 47-56, and Zhao et al. 2003, Adv. Drug Deliv. Rev., 55:483-499). These methods, however, have never been used to carry a plurality of different stereoisomer peptides, and none of them have described the conjugation or encapsulation of a plurality of stereoisomer peptides in their retroinverso and cyclic configuration. In this invention, for the first time such techniques with modifications are applied to create the novel therapeutic compounds of this invention.

The synthesis of low and high molecular weight oligomeric forms of polymers such as lactide and glycolide and their applications as carriers for drug delivery was carried out several decades ago (see Lewis D H. 1990. Controlled release of bioactive agents from lactide-glycolide polymers. In: Chasin M, Langer R, editors. Biodegradable polymers as drug delivery systems. New York: Marcel Dekker, p: 1-41, and Wu X S. 1995. Synthesis and properties of biodegradable lactic/glycolic acid polymers. In: Wise et al. Eds. Encyclopedic Handbook of Biomaterials and Bioengineering. New York: Marcel Dekker, p:1015-10541). These polymers are FDA approved and have wide acceptance in surgical procedures due to their biocompatibility and biodegradation through cleavage of its backbone ester linkages (see Tice T R and Cowsar D R. 1984. Pharm Technol, 11:26-35). However, none of these methods have described the conjugation or encapsulation of a plurality of stereoisomer peptides in their retroinverso and cyclic configuration with polymer PLGA. This invention presents the creation of such novel PLGA based therapeutic compounds.

Methods for encapsulation of drugs using a variety of size particles or carriers have also been described. The encapsulation of drugs entails the formation of polymer particles of a variety of sizes including nanoparticles, microparticles, miliparticles, nanocapsules, microcapsules, milicapsules, nanoemulsions, microemulsions, nanospheres, microspheres, and those made of a variety of substances to obtain liposomes, oleosomes, vesicles, micelles, surfactants, phospholipids, sponges, and those made with cyclodextrines. Thus, particulated polymers such as microspheres, microcapsules, and nanoparticles, are very useful because they can be administered by different routes in vivo (see Jain R A, 2002, Biomaterials, 21: 2475-2490; and Berkland C et al., 2002, J. Control Release, 82: 137-147). Polymer nanoparticles are used to encapsulate the novel polymer conjugates created in this invention.

Drugs of any size, regardless of molecular weight and solubility, can be loaded in the biodegradable microparticles using different manufacturing techniques. They include emulsion polymerization, interfacial polymerization, solvent evaporation, salting out, coacervation, combination of sonication and layer by layer technology, and solvent displacement/solvent diffusion mong others. Each method of drug encapsulation requires its own specific condition for stability, solubilization, and control releases immune-elimination (see Rajiv A J. 2000, Biomaterials, 21: 2475-490, and Sinha V R and Trehan A. 2003. J. Control. Release, 90:261-280). The method of encapsulation, therefore, is entirely based on the physicochemical activity of the type of drug and its intended application. Here specific modification and combination of methods are used to create the nanoparticles loaded with the composition of matter of this invention.

Another polymer amply used in biomedical applications is HPMA due to its biocompatibility and high solubility in water. HPMA has been conjugated mainly to low molecular weight drugs to increase their therapeutic effect and reduce their toxicity (e.g., toxic cancer drugs); these conjugates have also been labeled with fluorescent or radiolabeled tags to analyze the biodistribution of the drug-HPMA conjugate in tissues and cells. The selection of HPMA for biomedical applications relies on its extensive research, well-known chemical and structural properties, and their suitability as carriers for drug delivery, especially of toxic anti-cancer molecules, in many clinical applications (see U.S. Pat. No. 5,037,883; Kopecek, et al, Eur. J. Pharm. Biopharm., 2000, 50: 61-81; Vicent M J et al. 2008. Expert Opin Drug Deliv. 5(5): 593-614; Greco F and Vicent M J. 2008. Front Biosci. 2008 13:2744-56). Methods to synthesize HPMA to produce HPMA copolymers, the characterization of their properties, and the preparation of conjugates are standard and well established in the art (see Europ. Polym. J. 9, 7, 1973; Europ. Polym. J. 10 405, 1974), but none of these methods have ever been used to create the novel compounds of this invention.

In sum, the methods described above for peptide synthesis, their modification, and their conjugation to polymers or encapsulation have never been used to create the novel ligand-targeted multi-stereoisomer peptide-polymer conjugate compounds of this invention. Therefore, this invention for the first time uses such approaches with variations to create the novel therapeutic compounds described in this specification together with the examples, their representation in the figures and the claims describing the particular characteristics of the novel compounds. These compounds also provide targeted specificity to treat a particular disease and ideal biopharmaceutical properties that make them highly stable and suitable for any route of administration.

In view of the forgoing, it is appreciated that these novel and unique ligand-targeted multi-stereoisomer peptide-polymer conjugate compounds for a variety of therapeutic interventions, constitute a significant advancement in the art, and a new approach to treat human diseases.

SUMMARY

This disclosure features novel ligand-targeted multi-stereoisomer peptide-polymer conjugate compounds represented by the formula [sP]n-(L)-Pol-$P_L$, comprising a plurality of different stereoisomer peptides and a peptide-ligand conjugated directly or via a linker to a biocompatible polymer, wherein: sP represents a plurality of synthetic stereoisomer peptides comprising D-amino acids, or D- and unnatural amino acids, or D-, L- and unnatural amino acids, having retro-inverso or inverso configuration, and said configuration is a cyclic or a linear structure; the linear structure is alpha-helix or beta-sheet; each stereoisomer peptide sequence is selected independently from a group of peptides targeting functional domains of disease causing proteins or proteins that positively or negatively inhibit a disease protein; n is an integer of 2 to 5 stereoisomer peptides; L is a cleavable or a non-cleavable linker having 2 to 5 amino acid residues; or is absent; the amino acid residues of linker L are independently selected from the group comprising D-Lys, D-Gly, D-Phe, D-Leu, D-Ser D-Tyr, D-Glu, D-Gln, and D-Asn; Pol is a biocompatible polymer, and $P_L$ is a stereoisomer peptide-ligand that guides the delivery of said multi-stereoisomer peptide-polymer conjugate compound to a tissue or a cell in the body of a mammal. The cyclic compact structure of the stereoisomer peptide is created by head-to-tail linking of the terminal residues or by linking the side chain amino acids of the stereoisomer peptide, and wherein the sequences of two or more said stereoisomer peptides are selected independently from a group of ninety eight (98) peptides disclosed in the Sequence Listing entitled "Sequence_Listing_ST25.txt, and listed in the specification and from the group of peptides provided in the descriptions of the different target proteins.

Accordingly, in one aspect, stereoisomer peptides with D-amino acids in linear or cyclic configuration and their analogs; i.e., retro-inverso and inverso configuration, are ideal for therapeutic applications because they have increased stability and resist enzyme degradation allowing longer circulation in the blood. Furthermore, the function of the peptide-ligand, which is also a stereoisomer peptide in their retro-inverso or inverso configuration and linear or cyclic structure, is to guide the polymer carrying the different stereoisomer peptides to the target sites including tissues, cells, or subcellular locations (e.g., cytoplasm) in the body of a mammal, resulting in effective delivery and internalization of the therapeutic stereoisomer peptides.

In another aspect, the invention further refers to the use of ligand-targeted multi-stereoisomer peptide-polymer compounds as useful therapeutics to treat a variety of mammalian diseases mainly resulting from abnormal angiogenesis and inflammation which are the hall mark of most human diseases, which are caused by overexpression of disease causing proteins and the proteins of pathogenic microorganisms. Diseases include vascular growth, pathological conditions of the eye, cancer, metastasis, solid tumors, inflammation, arthritis, psoriasis, diabetes, and cardiovascular disorders; Alzheimer's, Parkinson's and neurological diseases, brain diseases such as bipolar disease, neurodegenerative diseases, diseases caused by aging, and diseases caused by pathogen agents including but not limited to HIV, malaria, and bacterial infections caused by MRSA, *Salmonella*, and the tuberculosis bacteria.

In one more aspect, the group of ninety eight (98) peptides with SEQ ID NOs 1-98 disclosed in the Sequence Listing entitled "Sequence_Listing_ST25.txt) and in the description, comprise peptides between 4 to 17 amino acids and constitute composition of matter of this invention. These peptides and the group of peptides listed in the descriptions of the target proteins, mimic short functional domains of natural proteins that are over-expressed, down regulated, or negatively interacting with other proteins causing a variety of human diseases, or positively inhibiting disease causing proteins. Peptides selected from any group of peptides disclosed or listed in the specification are artificial sequences and not natural peptides in their L-configuration. These peptides are synthetic peptides with D-amino acids in their retro-inverso or inverso configuration and chemically modified to obtain linear or cyclic compact structures. These structural characteristics provide unique and novel synthetic peptides that are highly stable, resistant to degradation by enzymes, and have extended shelf life, and enhanced biological properties.

In an additional aspect, a plurality of different synthetic stereoisomer peptides in their inverso or retro-inverso configuration with linear or cyclic structure are conjugated to a polymer directly or via a cleavable or non-cleavable linker depending on the polymer selected, and then coated or encapsulated in polymer particles of different size that can range between 1 to 100 µm in diameter further enhancing the physicochemical properties of the stereoisomer peptides, and creating ligand-targeted multi-stereoisomer-peptide polymer compounds, which constitute the composition of matter of this invention. Their enhanced properties not only provide ideal biopharmaceutical properties but allow these compounds to be used in different medical applications and be administered by different routes including but not limited to oral, parenteral, pulmonary, topical, mucosa, and transdermal.

In yet another aspect, this invention relates to the disclosed group of peptides which in addition of being synthesized with D-amino acids, in retro-inverso configuration and with linear or constrained cyclic structures, the constrained cyclic structure is created by a variety of methods that include head-to-tail linking of the terminal amino acids of the peptide creating an amide bond; linking the amino acids present in the side chains of the peptide creating a cyclic amide with a lactam bond, which can have a variable number of carbon atoms depending of the size of the D-peptide, or linking a terminal residue of the peptide with the terminal residue of a serine residue to create a thioether bond.

In another aspect, a linear peptide with alpha-helix configuration is stabilized by modification of amino acid residues adjacent to a motif or group of amino acids of interest. The addition of Cys residues to create a disulfide bond (—S═S—) or the addition of residues such as Lys or Glu to create a lactam bridge can be used to obtain a stable cyclic construct. For peptides with long helices, linking of the terminal residues creates a cyclopeptide with a stabilized alpha-helix.

In one additional aspect, this invention relates to the conjugation of stereoisomer peptides in their inverso or retro-inverso, and linear or cyclic configuration, to a functional group of a separate branch of a polymer such as PLGA, PLA, PCL, HPMA or PEG directly or via a linker that can be cleavable or non-cleavable. The stereoisomer peptides can also be directly conjugated to a polymer and then encapsulated in polymer particles of a desired size (e.g., nanoparticles) that have been conjugated to a ligand to create unique and novel ligand-targeted nanoparticles loaded with multi stereoisomer peptide-polymer conjugate compounds.

In yet another aspect, the peptide-ligand, also containing D-amino acids in retro-inverso or inverso configuration and linear or cyclic structures, but preferably cyclic structure, is conjugated directly to a branch of the polymer or on the surface of polymer particles loaded with different stereoisomer peptides that have been directly conjugated with the selected polymer. The function of the peptide-ligand is to guide the delivery of the polymer carrying a plurality of different linear or cyclic stereoisomer peptides in their retro-inverso or inverso configuration directly to the target site which is a tissue, cell, or a subcellular compartment (e.g., cytoplasm) in the body of a mammal.

In one more aspect, the peptide-ligand include but is no limited to high affinity receptor peptides, transport peptides, transduction domain peptides, chemotactic peptides, and cell penetrating peptides which in this invention are also synthetic stereoisomer peptides.

In another aspect, polymers used to create compounds to deliver drugs inside tissues or cells and cell compartments are selected from preferred polymers that include poly lactic-co-glycolic acid (PLGA), polylactic acid (PLA), Poly ϵ-caprolactone, N-(2-Hydroxypropyl)methacrylamide) (HPMA), and HPMA co-monomers, and polyethylene Glycol (PEG). A linker can be attached to the polymer and used to conjugate a stereoisomer peptide. The linker can be cleavable or non cleavable and may comprise two to five amino acid residues by addition or substitution preferably selected from the residues D-Phe, D-Leu, D-Lys, D-Gly, D-Ser, D-Tyr, D-Gln, D-Glu, D-Trp and D-Asn. In the case of stabilizing alpha-helix D-peptides small cycles can be created by adding D-Cys, D-Lys or D-Glu residues to the adjacent amino acids containing a motif of interest or by adding a D-Cys residue at each end of the peptide to create a disulfide bond. This bond can also be created by linking the ends of the terminal amino acids of the stereoisomer peptide to create a peptide bond. See examples of bonds created by cyclization of peptides in FIG. 1.

In one more aspect, the stereoisomer peptides can be conjugated to a polymer or encapsulated in a polymer particle of a determined size. Conjugation of peptides is achieved by using the available functional groups in the polymer's backbone. In the case of polymers without a functional group in their backbone, amino acid residues such as lysine are incorporated in the polymer chain during copolymerization to provide a functional group. This functional group can then be used to conjugate the peptide. Encapsulation of peptides in a polymer particle or composite particle formation is an important process for the controlled release of drugs. Polymer particles can have a variety of sizes including nanoparticles, microparticles, miliparticles, nanocapsules, microcapsules, milicapsules, nanoemulsions, microemulsions, nanospheres, microspheres, and those made of a variety of substances to obtain liposomes, oleosomes, vesicles, micelles, surfactants, phospholipids, sponges, and those made with cyclodextrines. The preferred polymer particles are nanoparticles.

In yet another aspect, this invention relates to using the polymer as specific intracellular carrier for the delivery of multi-targeted stereoisomer-peptide polymer conjugate compounds to cells via the endocytic pathway. This well characterized cell pathway allows the internalization of polymers such as PLGA, PCL, LA, PLA, HPMA, or PEG with its cargo mainly via clathrin- and caveolin-1-independent pathways. The D-peptides inside the cells are released from the polymer in the cell cytoplasm where the target proteins are found. This is achieved by enzymatic cleavage of the linkers and by the gradual release of the conjugated stereoisomer peptides located inside the polymer nanoparticles. The specific stereoisomer peptide-ligand conjugated in the surface of nanoparticles guides the polymer with its cargo into the tissues or cells for targeted delivery. Direct conjugation of peptides to a polymer and/or their encapsulation in nanoparticles, has sustained release capabilities at the target site (e.g., tumor) or in the intracellular lysosomal compartment where the nanoparticles are normally located after endocytosis.

This invention further refers to stereoisomer peptides that target physiologically and structurally relevant functional domains of proteins of interest. Domains include substrate specific and receptor sites, protein-protein interaction sites, docking sites for proteins or receptors interaction, protein specific folding loops, divalent metal ions sites, glycosilation and phosphorylation sites, and cell membrane and transmembrane domains. The desired effect of each stereoisomer peptide is to prevent, inhibit, or block the binding of a protein or a receptor, or a specific substrate or an organic or inorganic molecule to the target protein. The peptide may disrupt protein-protein interactions, protein loop folding, ionic interactions, or the binding of substrates, or the phosphorylation and glycosilation of proteins, or the interaction with the cell membrane. Therefore, the peptides are suppressing, eliminating, preventing, abolishing, blocking, or disrupting the physiological activity and/or the conformational structure of the target protein in a mammalian (e.g., animal or human) cell, or a protein important for the function and survival of an infectious microorganism. Thus, their function is to act as peptide antagonists. In the case of stereoisomer peptides targeting proteins that positively inhibit a disease protein their function is to act as an agonist.

The invention further provides novel pharmaceutical compositions comprising formulated ligand-targeted multi-stereoisomer peptide-polymer conjugate compounds comprising a plurality of stereoisomer peptides in the retro-inverso or inverso, configuration and with linear or cyclic constrained structures, but preferably retroinverso configuration and cyclic structure. Pharmaceutical compositions of these compounds are prepared for administration by the oral, parenteral (i.v., s.c., i.p., and i.c.), topical, transmucosal, transdermal, vaginal, anal, and pulmonary routes, and formulated in dosage configurations appropriate for each route of administration using pharmaceutically acceptable excipients. These pharmaceutical compositions are for the potential treatment of a variety of mammalian diseases (e.g., animals and humans) described in the anti-disease strategies provided in this invention.

BRIEF DESCRIPTION OF FIGURES

Features of the invention will be apparent from the following description of the different embodiments thereof and from the claims, taken in conjunction with the accompanying drawings, in which:

FIG. 5 illustrates a novel ligand-targeted HPMA-GFLG-D-Peptide-1-GFLG-D-Peptide-2-GFLG-D-Peptide-3-GG-Peptide-Ligand-conjugate compound created by radical polymerization of a mixture of three different co-monomers of stereoisomer peptides and a synthetic co-monomer of peptide-ligand in the presence of excess of N-2(Hydroxypropyl) methacrylamide (HPMA).

DETAILED DESCRIPTION

Figure 1:
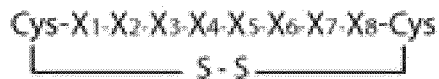
FIG. 1 provides examples of covalent bonds that are used to create cyclic stereoisomer peptides with compact structures and enhanced properties, and to stabilize stereoisomer peptides, especially those with alpha-helix structure. Formation of covalent bonds depends on the amino acid residues and their position in the stereoisomer peptide. The process of cyclization creates disulfide bonds, amide bonds (peptide bonds), lactam bonds and thioether bonds; however, cyclization is not limited to such examples since alternative methods can be used.
Figure 1:
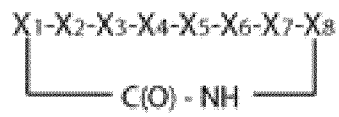
Figure 1:
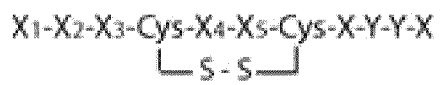
Figure 1:
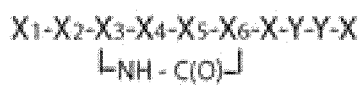
Figure 2:
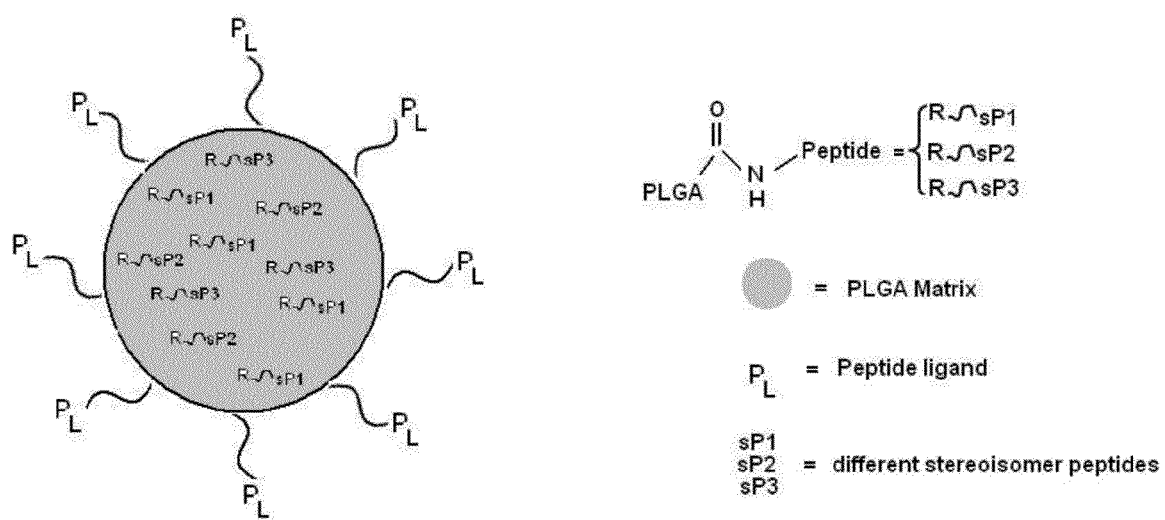
FIG. 2 is a diagram representing a novel ligand-targeted multi-stereoisomer peptide-polymer conjugate compound for targeted delivery, comprising a plurality of different stereoisomer peptides (sP1, sP2, and sP3) conjugated to PLGA, and encapsulated in PLGA nanoparticles that have been coated on the surface with a peptide-ligand ($P_L$) by conjugation.

While the invention is described in conjunction with the embodiments, it is understood that the invention is not limited to those embodiments. On the contrary, the invention is intended to cover all alternatives, modifications, and equivalents that may be included within the scope of the present invention as defined by the claims.

The practice of the invention disclosed herein employs conventional methods of chemistry, peptide synthesis, polymer science, molecular biology, microbiology, and cell biology and their content and complexity are within the level of skill in the art.

DEFINITIONS

As used in this description including the appended claims, the singular forms 'a', 'an', and 'the' include plural references, unless the content clearly dictates otherwise, and are used interchangeably with 'at least one' and 'one or more.' Thus, reference to 'a stereoisomer peptide' includes a plurality of stereoisomer peptides; and the like.

As used herein, the term 'about' represents an insignificant modification or variation of the numerical values such that the basic function of the item to which the numerical value relates is unchanged.

As used herein, the term 'comprise', 'comprises', 'comprising', 'includes', 'including', 'contains, 'containing', and any variations thereof, are intended to cover a non-exclusive inclusion, such that a process, method, or composition of matter, that comprises, includes or contains an element or list of elements does not include only those elements but may include other elements not expressly listed or inherent to such composition of matter, process, or method.

The amino acid residues comprising the sequences of the peptides disclosed in the Sequence Listing and specification are abbreviated using a three-letter code. The full names, three letter and single letter abbreviations are as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G.

As used herein, the term 'peptide' refers to a polymer of amino acid residues, but preferably refers to amino acids that are alpha amino acids joined together through amide bond. Peptides are organic compounds or short polymers created from the linking of two or more α-amino acids in a defined order, and in which the amine of one is reacted with the carboxylic acid of the next to form an amide bond or a peptide bond and refer to peptides up to 100 amino acids in length.

The term 'stereoisomer peptide' refers to peptides comprising amino acids that have two chiral configurations that are the mirror image of each other. In this invention, the peptides may comprise a mixture of D-L-amino, and unnatural amino acids or all D-amino acids. D amino acids have two different topologies: in one topology, D-amino acids are the mirror image of the naturally occurring (L-amino acid) forms, but do not have the same topology when aligned together; the second topology refers to D-peptides which have similar sequence to that of the natural L-peptides but have the positions of the carboxy- and amino-terminal residues reversed. These D-peptides are also termed retro-all-D-peptides or retro-inverso D-peptides. Most amino acids (except for glycine) are stereoisomers with L- and D-amino acids. Most naturally occurring amino acids are 'L' amino acids. The terms 'D amino acid' and 'L amino acid' are used to refer to absolute configuration of the amino acid, rather than a particular direction of rotation of plane-polarized light. The usage herein is consistent with standard usage by those of skill in the art.

The term 'retro-inverso' refers to a D-retro-stereoisomer peptide, consisting of D-amino acids in the reversed sequence.

The term 'amphipathic helix' refers to a protein with an alpha-helix producing a segregation of a polar and nonpolar faces with the positively charged residues residing at the polar-nonpolar interface and the negatively charged residues residing at the center of the polar face.

The term 'cyclic constrained structure' refers to a D-peptide in their inverso or retro-inverso configuration that have been cyclized by head-to-tail linking the terminal amino acids of the peptide creating an amide bond, or by linking the terminal Cys residues of the peptide creating a disulfide bond, or by linking the amino acids present in the side chains of terminal residues or core residues in the peptide creating a lactam bond, or by linking a Cys residue and a Ser residue creating a thioether bond.

The term 'amide bond' also known as peptide bond, refers to the covalent chemical bond formed between two molecules (e.g., amino acids) where the carboxyl group of one molecule reacts with the amino group of the other molecule, causing the release of a molecule of water.

The term "lactam bond' refers to an amide bond created between the side-chain of the residue lysine with the side-chain of the residues glutamate or aspartate. This structural feature is applied to cyclize peptides, stabilize alpha helices, or substitute for the less-stable disulfide bonds.

The term 'hydrophilic polymer' refers to a synthetic water-soluble polymer that alters the bio-distribution of a molecule attached to the polymer. Examples of such polymers include, but are not limited to N-(2-Hydroxypropyl) methacrylamide) (HPMA), poly(ethylene glycol) (PEG), poly(vinyl alcohol) (PVA), polyvinyl acetate, dextran, hydroxyethyl starch, gelatin, PVP, PHPMA, poly[N(2-hydroxyethyl)-DL-aspartamide (PHEA), and polysuccinamide (PSI). These polymers can be single monomers, co-monomers, a polymer chain, or a polymer with multiple branches.

The Term 'biodegradable polymer' refers to polymers (e.i., chains, branched or co-monomers) that break down to monomers losing their initial structural integrity. Biodegradable polymers are used in medical applications as drug carriers to gradually release a drug in the target tissue or cell. Examples of biodegradable polymers include but are not limited to PL, PGA, PLA, PCL, and PLGA.

The term 'polymer conjugate' refers to a synthetic substance consisting of chemical molecules formed from polymerization (polymer) that have conjugated a molecule such as antibody, protein, polypeptide, peptide, epitope, DNA, RNA, or a small chemical, fluorescent, or radioactive molecules directly or via a linker or spacer. The polymer is a co-monomer (two or more monomers), or a single polymer chain, or a polymer with multiple branches.

The term 'linker' also known as a 'spacer' or 'cross-linker' refers to a group of atoms (e.g., amino acids) that connect two adjacent chains of atoms in a large molecule such as a polymer with a peptide or a polymer with a protein creating a covalent bond. Linkers include oligopeptides, amide, ester, peptidyl, malonate, aminomalonate, carbamate, and Schiff base. In this invention, the linker is an oligopeptide, (e.g., di-, tri-, tetra-, penta-, hexa-residues).

The term 'oligopeptide' refers to small peptides between 2 and 20 amino acids and are named according to the number of amino acids in the chain like dipeptides, tripeptides, tetrapeptides, pentapeptides, etc.

The term 'peptide-ligand' refers to a peptide that binds specifically to a specific site on a viral or cellular surface protein and forms a complex. In this invention, the peptide-ligand is a stereoisomer peptide-ligand. The targeted peptide-ligand is conjugated to the polymer using a non-degradable linker or can be conjugated directly with a polymer and encapsulated in polymers of a particular size. Examples of peptide-ligands that provide suitable enhancing of cell targeting include but are not limited to high affinity peptides that interact with growth factors and their receptors; transport peptides that cross the blood barrier in brain, retina, and other tissues; and transduction domain, and cell penetrating peptides which cross the cell membrane.

The term 'conjugate compound' refers to a composition comprising a polymer with a linker and two or more molecules bound thereto. The polymer is poly lactic-co-glycolic acid (PLGA), poly lactic acid (PLA), Poly ε-caprolactone (PCL), N-(2-Hydroxypropyl) methacrylamide) (HPMA), and the HPMA co-polymer, and polyethylene Glycol (PEG). The linker is a di-tri-tetra-penta- or larger oligopeptide and the molecule bound to the linker or directly to the polymer is a stereoisomer peptide or a stereoisomer peptide-ligand, in retroinverso or inverso configuration with alpha-helix, or beta-sheet, or cyclic structure.

The term 'carrier' refers to a polymer (hydrophilic or hydrophobic) to which a composition, according to this invention, can be coupled. The carrier increases the molecular size of the compositions providing added selectivity and/or stability. The target molecules or polymer cargo (e.g., stereoisomer peptides) are delivered to tissues, cells, and sub-cellular locations. This delivery can be further enhanced by the specificity of the target molecules and the targeted ligand conjugated to the polymer.

The term 'particle' refers to a portion of matter of different sizes ranging from coarse particles sized between 10,000 to 2,500 nanometers, and fine particles sized between 2,500 and 100 nanometers.

The term 'nanoparticle' refers to ultrafine particles sized between 1 and 100 nanometers.

The term 'coating' or 'decorating' refers to covering that is applied to the surface of a polymer to improve its surface properties. In this invention, the improved surface property is a specific peptide-ligand conjugated on the surface area of the polymer for targeted delivery.

The term 'encapsulation' refers to a process in which molecules (e.g., stereoisomer peptides) are surrounded by a polymer coating to create a sphere or capsule with a uniform wall around it. The material inside the sphere or capsule is the fill (i.e., stereoisomer peptides), whereas the polymer wall is the shell or coating. The spheres have different diameters between as few millimeters to nanometers. The encapsulation process depends on the physical and chemical properties of the material to be encapsulated. In this invention, the sphere or capsule is made of polymer nanoparticles loaded with a plurality of different polymer-stereoisomer peptide conjugates.

The term 'pathogen agent' refers to microorganisms or parasites capable of causing disease, and it is usually restricted to living agents, which include viruses, bacteria, fungi, yeasts, protozoa, and helminthes. Pathogenicity is the ability of an organism to enter a host and cause disease. The degree of pathogenicity, known as virulence, depends on the organism's to cause disease under certain conditions. This ability depends upon the properties of the organism and the ability of the host to raise and immune response.

The term 'formulation agent' refers to both a usually inactive substance used in association with an active substance especially for aiding in the application of the active substance, capable to reach the intended target. Inactive substances include diluents, adjuvants, excipients, or vehicle, which can be sterile liquids, and vegetable or synthetic origin oils. Water or aqueous saline solutions, and aqueous dextrose and glycerol solutions, are preferably employed for injectable solutions.

The term 'pharmaceutically acceptable' refers to molecular entities and compositions that are 'regarded as safe', i.e., that are physiologically tolerable and do not typically produce an allergic, toxic or adverse reaction when administered to a human. Preferably, as used herein, the term 'pharmaceutically acceptable' means being approved by a regulatory agency of the Federal or a state government or listed in the U.S. Pharmacopeia or other generally recognized pharmacopeia for use in animals, and more particularly in humans.

The term 'therapeutic agent' refers to a compound that is used in the treatment of a mammalian disease, and may natural, or synthetic. Therapeutic agents generally promote or inhibit any biological process implicated in one or several human disease pathways. A therapeutic agent may be, for example, peptide agonists and antagonists, and inhibitors or anti- or pro-apoptotic agents, or modulators.

The term 'treating' refers to administering a pharmaceutical composition for therapeutic and/or prophylactic purposes to treat or prevent a mammalian disease.

The term 'treatment of a disease' refers to treating a patient already suffering from a disease to ameliorate the disease and improve the patient's condition. The term 'prevention of a disease' refers to prophylactic treatment of a patient who is not ill. Thus, in the claims and embodiments, treating is the administration of the pharmaceutical composition to an animal or a human either for therapeutic or prophylactic purposes.

Compounds of the formula $[sP]n-(L)-Pol-P_L$.

This invention, seeks the protection of novel ligand-targeted multi-stereoisomer peptide-polymer conjugate compounds represented by the formula $[sP]n-(L)-Pol-P_L$, comprising a plurality of different stereoisomer peptides and a peptide-ligand conjugated directly or via a linker to a biocompatible polymer, wherein: sP represents a plurality of synthetic stereoisomer peptides comprising D-amino acids, or D- and unnatural amino acids, or D-, L- and unnatural amino acids, having retro-inverso or inverso configuration, and said configuration is a cyclic or a linear structure; the linear structure is alpha-helix or beta-sheet; each stereoisomer peptide sequence is selected independently from a group of peptides targeting functional domains of disease causing proteins or proteins that positively or negatively inhibit a disease protein; n is an integer of 2 to 100 stereoisomer peptides; L is a cleavable or a non-cleavable linker having 2 to 5 amino acid residues; or is absent; the amino acid residues of linker L are independently selected from the group comprising D-Lys, D-Gly, D-Phe, D-Leu, D-Ser D-Tyr, D-Glu, D-Gln, and D-Asn; Pol is a biocompatible polymer that is a co-monomer, a chain, or has multiple branched chains, and $P_L$ is a stereoisomer peptide-ligand that guides the delivery of said multi-stereoisomer peptide-polymer conjugate compound to a tissue or a cell in the body of a mammal. The cyclic compact structure of the stereoisomer peptide is created by head-to-tail linking of the terminal residues or by linking the side chain amino acids of the stereoisomer peptide, and wherein the sequences of two or more said stereoisomer peptides are selected independently from a group of two hundred and fifty seven (257) peptides disclosed in "SEQ_LISTING_Jan_17_2014_ST25.txt," and listed in the specification in the descriptions of the different target proteins.

In another embodiment, the peptides selected are not natural peptides (L-peptide) but rather synthesized and chemically modified peptides to create synthetic stereoisomer peptides in their inverso or retro-inverso configuration with linear or cyclic structures, and conjugated to a polymer and/or encapsulated with polymer nanoparticles to create novel and unique ligand-targeted multi-stereoisomer peptide polymer conjugate compounds. These compounds are useful therapeutics for the anti-disease strategies outlined in this invention.

Peptides of the Invention and Proteins Involved in Human Disease.

In one embodiment, this invention discloses a group of two hundred and fifty seven (257) peptides. labeled SEQ ID NOs: 1-257, between 4 to 17 amino acids in length. The peptides are provided in the sequence listing entitled 'Sequence_Listing_ST25.txt.' and in the specification. Peptides selected from the group disclosed, and from the peptides listed in the description of the target proteins, refer to synthetic peptides that are chemically modified to create stereoisomer peptides with D-amino acids in retro-inverso or inverso configuration with linear or cyclic compact structures.

In another embodiment, the disclosed peptides in the "Sequence_Listing_ST25.txt" and replace with "Sequence_Listing_Jan__17__2014_ST25.txt" file are a useful group of peptides to create compounds against diseases caused by abnormal angiogenesis and inflammation which are the hall mark for diseases such as cancer, metastasis, ocular pathologies, neurological and brain diseases, vascular diseases and infectious diseases.

In one more embodiment, the peptides targeting diseases caused by a particular protein are listed in the Sequence Listing file and include peptides targeting abnormal angiogenesis, cancer, ocular pathologies, inflammation, neurological disorders, infectious caused by pathogens and some are pro-angiogenic.

In another embodiment, a group peptides with the majority between 8 to 15 amino acids in length are listed in the descriptions of the different proteins involved in human diseases. Peptides selected from the disclosed group or from the descriptions refer to synthetic, chemically modified stereoisomer peptides with D-amino acids, with retro-inverso or inverso configuration and linear or cyclic compact structure.

In yet another embodiment, the peptides disclosed and those listed with the target proteins mimic short key protein domains of functional importance and target specific regions of proteins that cause or exacerbate a disease, or have a positive effect to modulate or prevent a disease; or cause an abnormal physiological condition; or inhibit a protein of a pathogenic microorganism. Such domains are important for the proper folding and function of a particular protein and include but are not limited to folding loops, disulfide bridges, alpha-helix and cyclic structures, protein-protein interaction sites, substrate, receptor, and ion binding sites, and phosphorylation and glycosilation sites. The function of the peptides is, therefore, to inhibit or block the activity of the target protein. Some of the peptides are also intended to induce the activity of a protein that will subsequently inactivate a pathway to inhibit a diseases causing protein. The result of these activities provides peptides that function as competitive antagonists or agonists.

In an additional embodiment, the target proteins include growth factor VEGF, the receptors EGFR, VEGFR, PDGFR mTOR and NgR; the heat shock proteins HSP90, HSP70, HSP72, and HSC70, kinases such as p13K, TAK-1, GSK3; the chemokine proteins CCL5, CCR3, and CXCR6; the integrins avβ3, avB5, a5B1 and the proteins neuroepithelin, proepithelin, and p53; and collagen IV and XVIII containing anti-angiogenic domains such as tumnstatin, endostatin, and angiostatin, and the proteins somatostatin and thrombospondin (TSP-1) with anti-tumor activities. Other proteins of interest include a variety of short integrin, endothelial, and tumor derived sequence motifs, the brain derived angiogenesis inhibitor (BDAI) from human, and eight major HIV proteins including gp120, gp41, p24, tat, protease, integrase, reverse transcriptase, and Vif.

In yet another embodiment, additional proteins from infectious pathogens include the Prion protein PRNP, and proteins from infectious microorganisms such as Calcium-dependent protein kinase-1 (PfCDPK1), UIS3, and dihydrofolate reductase-thymidylate synthase (DHFR-TS) of the parasite paramecium; Mersacidin from *Bacillus*, Pep5, and Epicidin from *Staphylococcus aureus*; peptide-2 LEAP-2 from *salmonella*, and Acyl Carrier Protein Synthase (Acps) and pantothenate synthetase from *Mycobacterium tuberculosis*. Human Cystatin C and defensin with inhibitory sequences against pathogenic bacteria are also proteins of interest.

In still another embodiment, the stereoisomer peptides with constrained cyclic structures are functional, stable, and protease resistant stereoisomer peptides. These stable peptides are synthesized in the preferred retro-inverso and cyclic configurations. In cases where an alpha-helix is present in the sequence of the D-peptide, the cyclization process estabilizes the alpha-helix. These peptides are not used in free form but rather conjugated to the preferred polymers (e.g., PLGA, PLA, Poly ε-caprolactone, HPMA or PEG) which can be a co-monomer, a chain, or has multiple branched chains, to create unique and novel ligand-targeted multi-stereoisomer peptide-polymer conjugate compounds, which constitute the subject matter of this invention.

In one more embodiment, a plurality of stereoisomer peptides of the invention target the proteins by each contacting a particular protein with a particular composition that directs such activity in the cells. The stereoisomer peptides exert their effects by inhibiting, competing, blocking, and/or disrupting a folding structure, an activity, or a functional site of the target protein. Endocytosis of the composition in the cells allow entering the stereoisomer peptides inside the cell cytoplasm affecting, binding, blocking, competing or interacting with other molecules for the binding sites of the target proteins. This is particular effective with peptides that contain sequences mimicking the binding site of a receptor or a particular motif that binds to specific cells.

Epidermal Growth Factor Receptor (EGFR)

EGFR, a cysteine rich protein, is the cell membrane receptor for epidermal growth factor. Over-expression of EGFR and dysregulation or increased activity of EGFR signaling pathways promote the growth of malignant tumors. As a result, EGFR is an important target for therapeutic intervention.

In one embodiment, preferred representative peptides mimicking specific domains of protein EGFR involved in receptor binding, glycosilation, phosphorylation, and endocytosis include the sequences: SEQ ID NOs: 1, 35, 36, and 99-123

In another embodiment, these peptides contain terminal Cys residues that form disulfide bonds creating constrained cyclic structures, which are important for protein stabilization. Cyclic structures are also created by removing the Cys residues and using the terminal residues at each end of the peptide by head-to-tail cyclization. The last peptide in the table has alpha-helix structure, and targets the substrate active site of EGFR located in the catalytic domain of the receptor. This structure can be stabilized by cyclizing the peptide. Peptides from this and other related groups are selected independently to create novel ligand-targeted multi-stereoisomer peptide-polymer conjugate compounds for the potential treatment of small cell lung cancer, colo-rectal carcinoma, glioblastoma, and breast, head, neck, colon, ovarian, pancreatic, glioblastoma and bladder cancers.

Vascular Endothelial Growth Factor A (VEGFA)

VEGF-A is the predominant stimulator of angiogenesis and controls tissue vasculature under normal physiologic conditions through a regulated mechanism of expression. Under pathologic conditions, however, VEGF acts on endothelial cells of existing blood vessels to promote new blood vessel formation, and in the majority of cancers, VEGF is secreted by tumor cells. VEGF initiates the angiogenic process by activating endothelial cells and promoting their migration inducing the angiogenic switch, which is critical to the growth and malignant dissemination (metastases) of solid tumors. Free VEGF binds the receptors VEGFR1 (Flt-1), and VEGFR2 (Flk-1 or KDR), and its expression is driven by oncogene expression and hypoxia, and mediates the effects of other angiogenic molecules playing a central role in the control of tumor angiogenesis. VEGF is, therefore, the key mediator of vasculogenesis, angiogenic remodeling, and angiogenic sprouting. Given the role of VEGF in cancer and in angiogenesis related diseases, VEGF is the favorite target to develop therapeutics capable of inhibiting its activity under abnormal physiological conditions.

In one embodiment, preferred representative peptides mimicking specific functional domains of VEGF including the binding site for heparin and receptor, and the site for dimerization and function of VEGF, have the sequences: SEQ ID NOs: 7, 17, 20, 22, 25, 28, 82, and 124-128.

In another embodiment, these peptides have alpha-helix structure or terminal Cys that form constrained cyclic structures upon oxidation of their SH groups. Some peptides may have more than one disulfide bond and the peptides with alpha-helix can be further compacted and the helix stabilized by head-to-tail cyclization. Peptides from this and other related groups are selected independently to create novel ligand-targeted multi-stereoisomer peptide-polymer conjugate compounds for the potential treatment of non small cell lung cancer, renal cancer, colon cancer, head and neck squamous cell carcinomas, ovarian cancer, cervical cancer, multiple myeloma, leukemia, lymphoma, malignant glioma, vascular and tumor growth, and many pathological conditions of the eye including age related macular degeneration, choroidal neovascularization, diabetic retinopathy, and macular edema.

Heat Shock Proteins (HSP90, HSP70, HSP72, and HSC70)

Heat shock proteins are a group of highly conserved molecular chaperones, which respond to cellular stresses. Heat-shock protein 90 (Hsp90) is an essential chaperon for function and integrity of a wide range of oncogenic client proteins like hypoxia-inducible-factor-1 alpha (HIF-1a), signal transducer and activator of transcription-3 (STAT3), intracellular kinases (Akt, Erk), epidermal growth factor receptor (EGFR), and insulin-like growth factor receptor (IGFR). HSP90 is constitutively expressed at high levels in many cancers, (gastric, liver, Hodgkin lymphoma). Inhibition or blockade of Hsp90 would improve anti-tumoral and anti-angiogenic effects of drugs such as rapamycin and potentially blocking oncogenic signaling molecules. Hsp90 is involved in a variety of regulatory functions including regulation of phosphorylation of SGK-1, which contributes to malignant epithelial cell proliferation. Hsp90 interacts with raptor and regulates mTOR signaling upon T cell activation; regulates Jak-STAT signaling in cells, and modulates the redox status of cytosol in resting and apoptotic cells by reducing Cytochrome C.

In one embodiment, preferred representative linear peptides with alpha-helix structure mimicking domains important for ATP substrate interaction and binding to Hsp90, and the terminal domain have the sequences: SEQ ID NOs: 10, 73, and 129-132. These peptides are further stabilized by cyclization using a variety of methods.

In another embodiment, HSP70 family contains at least eight distinct members, including HSC70, HSP70-8 or HSP73 in the cytoplasm and nucleus; and HSP72 (HSP70, HSP70-1A or HSP70-1B) in the cytoplasm/nucleus/lysosome. Their functions include nascent protein folding; preventing formation of protein aggregates; assisting re-folding of denatured proteins; facilitating their degradation when proteins cannot be repaired; modulating the assembly/disassembly of protein complexes; aiding the translocation of proteins across cellular membranes, and inhibiting cell death. Sometimes these functions are undesirable if the protein being stabilized by the heat shock protein is a disease protein. HSP70 levels are abnormally high in a wide variety of tumor cell types and contribute to tumorigenesis and resistance to chemotherapy. HSP70 iso-configurations, HSP72 and HSC70 are induced in colon and ovarian cancer cell lines exposed to HSP90 inhibitors; and HSC70 modulates HCV infectivity. Important domains of these proteins include ATPase and substrate binding and the interaction with the HSP-organizing protein. Based on the antiapoptotic function of HSP70 iso-configurations and their essential role in the substrate-loading phase of the HSP90 chaperone cycle, it is important to find inhibitors to silence the activities of both HSP72 and HSC70 and to indirectly inhibit HSP90 chaperone function which may potentially lead to a greater apoptotic effect than that observed with pharmacologic HSP90 inhibitors. The substrate binding sites of heat shock proteins and their interactions with proteins are of functional importance since substrates bind with high affinity and specificity to the C-termini of HSP70, HSP72, and HSC70.

In yet another embodiment, preferred peptides mimicking domains of Hsp90 and the C-termini of the protein include the sequences: SEQ ID NOs: 74 and 133-144. Stabilization of these sequences, including the alpha-helix peptides, is achieved by cyclization of the terminal Cys residues creating a disulfide bond or by head-to-tail cyclization of the terminal residues at each end of the stereoisomer peptide.

In one additional embodiment, these heat shock related peptides and peptides of other groups are selected independently to create novel ligand-targeted multi-stereoisomer peptide-polymer conjugate compounds for the potential treatment of diseases caused by a variety of cancers and eye pathologies including but not limited to age related macular degeneration, choroidal neovascularization, diabetic retinopathy, and macular edema.

P13K/Atk and p13K/mTOR

Phosphoinositide kinases (PIKs) phosphorylate the inositol ring of phosphoinositides, therefore, acting as signal transducers. Depending on the phosphorylation site on the carbohydrate, PIKs include phosphoinositide 3-kinases (PI3Ks), phosphoinositide 4-kinases (PIP4Ks) and phosphoinositide 5-kinases (PIP5Ks). PI3Ks are further grouped in three classes depending on their subunit structure, their regulation, and their substrate selectivity, and each class contains various iso-configurations. The PI3K pathway is linked to cancer development and is activated by several growth cofactors and oncogenes. Class I PI3K is a tyrosine kinase that mediates, through its p110a subunit enzymatic activity, the mitogenic signal transduction pathway. P13K is also an effector molecule that interacts with the cytoplasmic domains of growth factor receptors through adaptor subunits containing SH2 domains. P13K/Atk pathway is activated in multiple myeloma and p13K/mTOR is activated in pancreatic cancer.

Malignant gliomas commonly over express the oncogenes EGFR and PDGFR, which contain mutations and deletions of the tumor suppressor genes PTEN and TP53, leading to activation of the PI3K/Akt and Ras/MAPK pathways. Gonadotropin FSH acts via its receptor stimulating the PI3K-AKT pathway. Activation of this pathway occurs in solid tumors, including ovarian epithelial tumors, through mutation of the PI3K subunit genes or inactivation of the tumor suppressor, PTEN. Peptides In one embodiment, preferred peptides mimicking regions of PI3-kinase p110 subunit alpha including the catalytic domain, the ATP binding site, and phosphorylation sites of this protein have the sequences: SEQ ID NOs: 26, 145-149. These peptides are further stabilized by cyclization using different approaches.

In another embodiment, peptides from this and other related groups are selected independently to create novel ligand-targeted multi-stereoisomer peptide-polymer conjugate compounds for the treatment of acute gliomas, myeloma, and pancreatic and ovarian cancers.

Transforming-Growth-Factor-Beta-Activated Kinase-1 (TAK-1)

TAK-1 is a member of the MAPK kinase and a key regulator in the pro-inflammatory signaling pathway that can be activated by TGF-Beta, IL-1Beta, TNF alpha, and toll-like receptor ligands. In cells, TAK-1 can exist as the catalytic component of two different complexes TAK-1-TAB1-TAB2 or TAK-1-TAB1-TAB3. TAK-1-binding protein-1 is required for TAK-1 activity. TAB2 and TAB3 are adapter proteins containing ubiquitin binding domains which are required for the activation of TAK-1; once activated, it activates the NF-kappa B pathway by interacting with the TNF-alpha receptor-associated factor (TRAF) and phosphorylating the NF-kappa B inducing kinase. TAK-1 phosphorylation also correlates with phosphorylation at Thr-187, and activation of the p38a and JNK pathways via phosphorylation of MAP kinase (MKK) 3/6 and MKK4/7, respectively. Signaling pathways downstream of TNF-alpha are also severely impaired in TAK-1 deficient cells, hence the importance of TAK-1 in the pro-inflammatory signaling pathways. The activation of NF-kappa B is linked to the development and progression of human cancers such as hepatocellular, prostate, and breast carcinoma, and to the conversion of TGF-beta from a suppressor to a promoter of mammary tumorigenesis. The inhibition of important domains of TAK-1 protein provides targets for the development of therapeutics to treat a variety of cancers.

In another embodiment, preferred alpha-helix peptides mimicking the catalytic domain, the ATP binding site and phosphorylation sites of TAK-1 include the sequences: SEQ ID NOs: 150-152. Further cyclization of these peptides enhances their stability.

In one more embodiment, peptides from this and other related groups are independently selected to create novel ligand-targeted multi-stereoisomer peptide-polymer conjugate compounds for the potential treatment of pancreatic, liver, prostate, and breast cancers.

Mammalian Target of Rapamycin (mTOR)

Mammalian target of rapamycin (mTOR) is a large multi-domain serine/threonine protein kinase which plays a central role in the regulation of cell growth, cell proliferation, cell motility, cell survival, protein synthesis, and transcription. This protein is present in cells as mTORC1 and mTORC2, which contain a known binding partner mLST8/GbL, but differ in that the third protein component of mTORC1 is raptor and of mTORC2 is rictor; mTORC2 is involved in regulating the assembly of the actin cytoskeleton in cells and is a key activator of the protein kinase Akt, an essential component of the insulin/PI3K signaling pathway. Akt indirectly activates mTORC1 via phosphorylation-induced inhibition of the complex formed by the tuberous sclerosis proteins TSC1 and TSC2, which acts as a negative regulator of mTORC1 activity; mTORC1 is a downstream effector of mTORC2. Thus, mTOR is an essential target of survival signals in many types of human cancer cells, and its activity is modulated by leucine, rapamycin, and phosphatidic acid; the last two bind to the FRB domain of mTOR.

In one embodiment, many conditions that shift cells from states of nutrient utilization and growth to states of cell maintenance and repair extend lifespan. Inhibition of the nutrient sensor target of rapamycin mTOR increases lifespan. Although rapamycin is used extensively for treating cancers and is extremely selective for mTOR, this drug has very low bioavailability, and can potentially activate pathways that could maintain mTOR active, therefore leading to treatment failure. Thus, the development of selective mTOR kinase inhibitors with higher stability, resistance, and bioavailability is an important unmet medical need.

In another embodiment, preferred linear peptides mimicking functional domains of mTOR including the ATP binding site and FRB domain, which is the site for binding rapamycin, phospatydic acid and leucine include the sequences: SEQ ID NOs: 153-164. Cyclization of these peptides using a variety of approaches will further enhance their stability.

In an additional embodiment, peptides from this and other related groups are selected independently to create novel ligand-targeted multi-stereoisomer peptide-polymer conjugate compounds for the potential treatment of renal, ovarian prostate and liver cancers, and as an anti-aging.

Vascular Endothelial Growth Factor Receptor 2 (VEGFR2)

The dependence of cancerous tumors on nutrients and oxygen for growth via angiogenesis (new vessels formation) is facilitated by VEGF, which is secreted by tumors inducing a mitogenic response through its binding to one of three-tyrosine kinase receptors (VEGFR-1, -2 and -3) on nearby endothelial cells. VEGFR1 is a positive regulator of macrophage migration and regulates VEGFR2 signaling by acting as a decoy receptor; VEGFR2 mediates the major growth effects and permeability associated with VEGF, whereas VEGFR3 is essential for lymphatic vessel formation. Thus, inhibition of this signaling pathway should block angiogenesis and subsequent tumor growth. Endothelial expression of VEGFR2 closely parallels VEGF expression in angiogenic responses. Suppression of the VEGF/VEGFR2 signaling pathway interferes with new blood vessel formation, and thus they are targets for therapeutics. VEGFR-2 also plays a pivotal role in choroidal neovascularization (CNV) development; it is detected on retinal progenitor cells, and is generally considered to promote new vessels.

In one embodiment, preferred peptides mimicking VEGFR2's catalytic domain, the ATP and substrate binding sites, the activation loop, and the amino acids that directly interact or bind inhibitors include the sequences: SEQ ID NOs: 31 and 165 169. Cyclization of these peptides using various approaches further enhances their stability.

In another embodiment, peptides from this and other related groups are selected independently to create novel ligand-targeted multi-stereoisomer peptide-polymer conjugate compounds for the potential treatment of pathological conditions of the eye like age related macular degeneration, choroidal neovascularization, diabetic retinopathy, and macular edema, malignant brain tumors, thyroid carcinomas, and breast and cervical cancers.

Platelet Derived Growth Factor Receptor-Alpha and -Beta (PDGFRa and PDGFR-b)

The platelet-derived growth factor (PDGF) family, a potent mitogen for a wide variety of cell types of mesenchymal origin, is a target of interest. The PDGF family consists of four members (PDGF-A, PDGF-B, PDGF-C and PDGF-D), which exert their biological effects by binding as homo- or heterodimers to two receptor tyrosine kinases (PDGFRa and PDGFRb). PDGF-AA, PDGF-AB, PDGF-BB and PDGF-CC dimers bind to PDGFRa with high affinity, whereas PDGF-BB and PDGF-DD dimers preferentially bind PDGFR-b. PDGF signaling is critical for embryonic development, whereas in the adult, it is important in wound healing and in the control of interstitial fluid pressure. PDGF is an important factor in regulating angiogenesis and tumor cells. Glioblastomas, fibrosarcomas and osteosarcomas often coexpress PDGF ligands and their cognate receptors leading to autocrine stimulation of tumor cell growth. Both PDGFRa and PDGFRb signaling seems to be involved in the regulation of various angiogenic pathways and stromal cell functions. Thus, combined inhibition of PDGFRa and PDGFR-b results in markedly decreased tumor growth in vivo because of impaired recruitment of peri-endothelial cells. PDGFRa is implicated in the growth of gliomas, uterine sarcomas, renal cell carcinoma, and non-small cell lung cancer and PDGFR beta is implicated in chronic myelomonocytic leukemia, renal and non-small cell lung cancer, gastric and esophageal cancers.

In one embodiment, preferred peptides mimicking short sequences of the catalytic domain, and the substrate, ATP and phosphorylation binding sites, important for the overall activity of PDGFRa and PDGFRb include the sequences: SEQ ID NOs: 170-176. These short peptides are further stabilized by cyclization.

In another embodiment, peptides from this and other related groups are selected independently to create novel ligand-targeted multi-stereoisomer peptide-polymer conjugate compounds for the potential treatment of gliomas, uterine sarcomas, renal cell carcinoma and non-small cell lung cancer; chronic myelomonocytic leukemia, and gastric and esophageal cancers.

PC Cell-Derived Growth Factor (PCDGF) or Proepithelin (PEPI)

PC cell-derived growth factor (PCDGF), known as proepithelin (PEPI), granulin-epithelin precursor, GP88, progranulin and acrogranin, plays a critical role in development, cell cycle progression, cell motility, and tumorigenesis. This 90 KDa protein comprise 6-KDa fragments, named granulin A, B, C, D, E, F, and G that correspond to individual domains that have been isolated from a variety of human tissues. The PCDGF gene plays a critical role in tumorigenesis and in several breast cancer cells and its expression correlates with an aggressive phenotype. Over-expression of PCDGF plays a significant role in adipocytic teratoma, glioblastomas, multiple myeloma, and renal cell, gastric and ovarian carcinomas. It also promotes migration, wound healing, and invasion of bladder cancer cells, supporting the evidence that PCDGF or proepithelin play as well a critical role in bladder and prostate cancers, and stimulates invasive behavior. Mutations in the PCDGF gene cause front-temporal dementia leading to neuro-degeneration; hence its critical function in regulating survival of neuronal cells. Inhibiting PCDGF impedes the proliferation of breast cancer cells; MDCK renotubular epithelium; ovarian carcinoma; the proliferation of human glioblastomas in culture, all of which are cells from tumor types associated with elevated PCGDF gene expression. PCDGF is therefore, an interesting therapeutic target for the treatment of cancer.

In one embodiment, preferred peptides mimicking the sequence domains of three different epithelin modules (epithelin A, D and F) located within the PCGDF protein sequence include the sequences: SEQ ID NOs: 177-191

In another embodiment, these cys rich peptides form 2 to 6 disulfide bonds via oxidation of SH groups allowing the formation of constrained cyclic structures. Peptides from this and other related groups are selected independently to create novel ligand-targeted multi-stereoisomer peptide-polymer conjugate compounds for the potential treatment of glioblastomas, anaplastic astrocytomas, oligodendrogliomas; uterine sarcomas, renal cell carcinoma, non-small cell lung cancer; chronic myelomonocytic leukemia, and renal, prostate, breast, gastric and esophageal cancers, and laryngeal squamous cell carcinoma.

Neuropilin-2 (NRP-2) and p53.

Neuropilin-1 and 2 (NRP-1and NRP-2), non-tyrosine kinase transmembrane glycoproteins that share 44% sequence homology, are overexpresed in most cancers. Expression of neuropilins is found in neurons, on inflammatory cells, vascular smooth muscle cells, endothelial cells and tumor cells. Neuropilins are not kinases and can signal via their short intracellular domain directly by recruiting synectin to the cell membrane. NRP expression on tumor cells is correlated with a malignant phenotype in melanoma, prostate, pancreatic cancers, and the formation of tumor-associated lymphatics in lung metastasis. In colorectal cancer, NRP regulates tumor growth. In pancreatic ductal adenocarcinoma (PDAC), NRP-2 shows greater expression than in nonmalignant ductal epithelium. NRP-2 in colorectal carcinoma plays a role in several critical aspects of the malignant; NPR-2 in PDAC is involved in survival signaling, migration, invasion, and anchorage-independent growth in vitro. In vivo, cells deficient in NRP-2 had decreased tumor growth, also associated with a decrease in Jagged-1 expression, a member of the Notch family of ligands and receptors, in the tumor cells. Thus, the reduction of tumor growth may be due to the secondary effect on angiogenesis since there is a decrease in functional vasculature within the tumor. This molecule is therefore a potential therapeutic target.

In one embodiment, preferred peptides mimicking sequences in the a domain of Neuropilin-2 (NRP-2) with ala2 structures important for the binding of Sema3A to neuropilin; and sequences in the b domain with b1b2 structures important for the binding of VEGF-165 to neuropilin, include the sequences: SEQ ID NOs: 12, 17, 20, 37, and 192-196.

In another embodiment, these peptides have terminal cys residues that form disulfide bonds via oxidation of SH groups creating compact cyclic structures. Peptides from this and other related groups are selected to create novel ligand-targeted multi-stereoisomer peptide-polymer conjugate compounds for the potential treatment of breast, prostate, colorectal, and pancreatic cancers, melanoma, lung metastasis and pancreatic ductal adenocarcinoma.

In one additional embodiment, P53 protein, known as the guardian of the genome, and master regulator of apoptosis and other forms of cell death, is a tumor suppressor protein encoded by the TP53 gene. This protein is crucial in multicellular organisms. It regulates the cell cycle and is involved in the prevention of cancer by maintaining the stability of the genome preventing mutations that lead to cancer. A common polymorphism of TP53 gene, involves the substitution of an arginine residue for a proline residue at codon position 72.

This mutation has been linked to a variety of cancers like pancreatic, breast, renal and lung cancers among others, and more than 50% of human tumors contain a mutation or deletions of the TP53 gene. There is ample evidence of the association of p53 with MDM2 protein (Murine Double Minute 2) and tumorigenesis in a variety of human cancers. Accumulation of mutated p53 in the cancer cell, allows p53 to gain new oncogenic functions contributing to transformation and metastasis. While current studies find that the Akt signaling pathway phosphorylates MDM2 leading to the nuclear translocation and degradation of the tumor suppressor p53 protein, it is also observed that MDM2 activates the Akt signaling pathway through an interaction with REST (repressor element 1 silencing transcription) factor conferring survival advantage to cancer cells independently of p53 status. Thus, it is important not only to target the interaction between p53 and MDM2 with novel drugs which will inhibit MDM2 and indirectly Akt kinase (see Pk13/Atk addressed above) to prevent its activation and the inhibition of wild type oncogene suppressor p53.

In one more embodiment, preferred peptides sequences to target MDM2 to prevent p53-MDM2 interaction include the sequences: SEQ ID NOs: 14-16, 21, 37, and 251-253. Cyclization of these peptides further enhances their stability. Since MDM2 is found in most cancers down-regulating p53, peptides from this and other related groups are selected to create novel ligand-targeted multi-stereoisomer peptide-polymer conjugate compounds for the potential treatment of a variety of cancers.

Integrins Alpha-vβeta3 (αvβ3) and Alpha-vβeta1 (α5β1)

The integrins αvβ3- and α5β1, receptors for a variety of extracellular matrix proteins like vitronectin or fibronectin, play a major role in cancer. The interaction of integrin α5β1 with its main ligand in the extracellular matrix, fibronectin, is known to influence the survival of tumor cells and to favor their proliferation by modulating apoptosis through the upregulation of antiapoptotic proteins or the suppression of apoptotic mediators. Furthermore, this activity is enhanced by the presence of both the RGD motif and the peptide PHSRN for interaction with fibronectin; integrin α5β1 is also involved in the development of choroidal neovascularization (CNV) and other cancers. Thus, inhibition of α5β1 may provide an alternative to the current standard for cancer and CNV theraphies which involves inhibition of VEGF, which is not effective in the majority of cases. Integrin αvβ3 is also involved in cancer; it has been reported to be strongly expressed on activated endothelial cells and cancer cells. It is over expressed in melanoma, glioblastoma, ovarian, and breast cancer; therefore, αvβ3 is also an attractive protein target for cancer therapy. High-affinity αvβ3 and α5β1 integrin ligands block these integrins and inhibit angiogenesis, induce endothelial apoptosis, decrease tumor growth, and reduce invasiveness and spread of metastasis. Both αvβ3 and α5β1 are therefore protein targets for cancer therapy.

In one embodiment, preferred peptides mimicking sequences of Alpha-vβeta integrins or targeting αvβ3 and α5β1 include the sequences: SEQ ID NOs: 8, 9, 38, 41, 43, 50, 96, and 97, 197-202 and 254-255.

In another embodiment, these peptides, mostly with cys residues, target key domains important for the interaction of calcium and the amino acid residues that bind with the tripeptide motive found in a variety of growth factors such as IGF-I, extracellular matrix proteins, and receptor ligands (integrins). The peptides form disulfide bonds via oxidation of SH groups creating compact cyclic structures. These residues can be exchanged for non Cys residues to form amide bonds. Peptides from this and other related groups are selected independently to create novel ligand-targeted multi-stereoisomer peptide-polymer conjugate compounds for the potential treatment of breast, prostate, colorectal, and pancreatic cancers; tumor growth and metastasis; rheumatoid arthritis, psoriasis, restenosis, and eye diseases including age related macular degeneration, choroidal neovascularization, diabetic retinopathy, and macular edema Chemokines CCL5, CCR3 and CXCR6

Chemokines, small proinflammatory chemoattractant cytokines that bind to G-protein coupled seven-span transmembrane receptors, are major regulators of cellular trafficking. Chemokines induce direct migration of leukocytes along a chemical gradient of ligand(s), and their production is stimulated by proinflammatory cytokines, growth factors and, in general, by pathogenic stimuli arising in inflammatory tissues. In diseased tissues, different tumor cell types trigger a complex chemokine network that influences the quality and quantity of immune-cell infiltration and, consequently, malignant cell proliferation, survival, spread, and angiogenic response. CCL is as a product of activated T cells and an inflammatory chemokine. CCL5 mediates chemotactic activity in T cells, monocytes, dendritic cells, natural killer cells, eosinophils, and basophiles; it is also associated with chronic inflammatory diseases such as rheumatoid arthritis, and inflammatory bowel disease. CCL5 expression levels are associated with melanoma, lung, prostate, pancreatic cancers and breast cancer, and correlate with disease progression; it also modulates cell migration and invasion in several cancer cells. Interaction of CCL5 with its specific receptor CCR on the surface of cancer cells induces cancer invasion. CCL5 and receptor CCR5 increases the migration and expression of matrix metalloproteinases (MMPs), found in human oral cancer cells.

In one embodiment, the implications of CCL5 with inflammatory diseases and cancer, the protein is a target of interest to develop novel therapeutics. Human eosinophils also respond to a variety of CC chemokines like eotaxin, eotaxin-2, eotaxin-3, which are regulated by T cell expressed and secreted RANTES, monocyte chemoattractant protein (MCP)-2, MCP-3, and MCP-4 through binding to the CC chemokine receptor-3 (CCR3). CCR3, a seven transmembrane domain G coupled receptor, is expressed in eosinophils, Th2 T cells and mast cells. Because of its action on eosinophils and on many cell types that are crucial for induction of an allergic response, eotaxin and the CCR3 receptor are targets of interest for therapeutic intervention.

In another embodiment, preferred peptides mimicking important functional domains of CCL5 and putative receptor-binding sites of CCR1, CCR3, CCR4, or CCR5 include the sequences: SEQ ID NOs: 203-205.

In one additional embodiment, these peptides have terminal Cys residues that form disulfide bonds via oxidation of SH groups creating constrained cyclic peptides. The last peptide mimics a short sequence of the eosinophil eotaxin receptor of CCR3. Peptides from this and other related groups are selected independently to create novel ligand-targeted multi-stereoisomer peptide-polymer conjugate compounds for the potential treatment of diseases caused by inflammatory responses and cancers.

In one more embodiment, multiple pairs of chemokines and their receptors play critical roles in cancer progression. CXCL16, a ligand for CXCR6 are expressed in a variety of tissues and cells including activated endothelial cells, Hodgkin's disease-derived tumor cells, and tumor-associated macrophages (rectal cancer). CXCL16 also functions as a potent and direct activator of nuclear factor-nB and induces nB-dependent proinflammatory gene transcription through heterotrimeric G proteins, PI3K, PDK-1, Akt, and InB kinase. It also plays a role in the development and progression of atherosclerotic vascular disease. Proangiogenic CXCL16 is also a transmembrane molecule transported to the cell surface. The receptor, CXCL16R constitutively expresses in bone marrow and in prostate tissues via CXCR6. The CXCR6/AKT/mTOR pathway plays a central role in the development of prostate cancer (PCa), and alterations of CXCR6 over-expression are associated with invasive growth and angiogenic activities of PCa cells. Thus, blocking the CXCR6/AKT/mTOR signaling pathway is likely to have an antimetastatic effect.

In yet another embodiment, preferred peptides mimicking functional domain located within a loop created by a disulfide bond domain of CXCR6 include the sequences: SEQ ID NOs: 39, 40, 206-208.

In still another embodiment, peptides from this and other related groups are selected independently to create novel ligand-targeted multi-stereoisomer peptide-polymer conjugate compounds for the potential treatment of prostate cancer. Proteins as Inhibitors of Angiogenesis: HIV Tat, Collagen, Thrombospondin (TSP-1), Collagen IV and XVIII, and Anti-Angiogenesis Brain Inhibitor (ABI)

HIV proteins like gp120, gp41, Tat, Vif, protease, integrase, and reverse transciptase contain important amino acid motifs that interact with integrins, which in turn mediate binding of virus surface protein to CD4 cells. Tat, a potent transactivator of viral transcription, binds to cellular factors and mediates their phosphorylation, resulting in increased transcription of all virus genes providing a positive feedback cycle. PCDGF (Granulin E region) binds to HIV Tat protein suppressing transactivation by HIV-1 Tat, a key progression factor of Kaposi's sarcoma (KS) due to the presence of amino acid motifs that bind $\alpha v \beta 3$ integrin promoting its angiogenic activity in vivo. Thus, inhibition of Tat production or prevention of its activity could be a way to inhibit the development and progression of KS in AIDS patients. Tat Cys-rich and basic domains have positive modulatory effect by inhibiting a variety of growth factors, receptors, and cellular activities. HIV Tat inhibit VEGF165 by binding to KDR and neuropilin-1 (NP-1) receptors in endothelial cells. Tat inhibits VEGF induced ERK activation and mitogenesis in endothelial cells; it also inhibits angiogenesis in vitro; inhibit ERK activation induced by basic fibroblast growth factor, and induce cell apoptosis. These properties of HIV-1 Tat protein and its fragments indicate that their major effect in endothelial cells is apoptosis independent of specific inhibition of VEGF receptor activation.

In one embodiment, preferred peptides mimicking domains of HIV tat, protease, vif, reverse transcriptase, and gp120 sequences important for binding to integrins potentially inhibiting cellular processes or pathways related to angiogenesis, and viral infection include the sequences: SEQ ID NOs: 19, 24, 30, 32, 33, 54-58, 90, 91, 98, and 209-211.

In another embodiment, the peptides are modified to include terminal Cys residues that form disulfide bonds via oxidation of SH groups creating constrained cyclic structures. Peptides from this and other related groups are selected independently to create novel ligand-targeted multi-stereoisomer peptide-polymer conjugate compounds for the potential treatment of abnormal angiogenesis induced by the overexpresion of growth factors such as VEGF-165, neuropilin, KDR receptor, integrin and to inhibit HIV.

In one additional embodiment, Type IV and XVIII collagen, have positive effects by inhibiting endothelial cell proliferation, migration, and tube formation. They contain endogenous domains with antiangiogenic activity. For example Type IV Collagen has a domain, tumstatin with antiangiogenic activity mediated by $a 1\beta 1$ integrin. Type XVII collagen has a domain, endostatin, with antiangiogenic activity. Both collagen gen types suppress VEGF, and have anti-tumor activity. The protein inhibits phosphorylation of focal adhesion kinase via binding to $\alpha 5\beta 1$ integrin; it is implicated in several signaling pathways, including down regulation of c-myc and RhoA activity, blockage of VEGF signaling, inhibition of the wnt-signaling pathway, and inactivation of metalloproteinases. The association of XVIII collagen with laminin and heparin indicates that different regions of the protein carry out different biological functions, and the disulfide bonds are important for the stability and activity of the protein.

In one more embodiment, a peptide located near to the C-termini of the alpha 1 type XVIII collagen isoconfiguration-3 precursor, has sequence SEQ ID NO: 4-6, 11, 49, 69, and 212. The cys residues form a disulfide bond via oxidation of SH groups creating a constrained cyclic peptide.

In other embodiment, this peptide together with peptides of related groups are selected independently to create a novel ligand-targeted multi-stereoisomer peptide-polymer conjugate compound for the potential treatment of abnormal angiogenesis, pathological conditions of the eye including age-related macular degeneration, choroidal neovascularization, diabetic retinopathy, and macular edema, and cancer.

In one more embodiment, Thrombospondin-1 (TSP-1) and brain specific angiogenesis inhibitor (BSAI) are naturally occurring inhibitor of angiogenesis. TSP-1 is a large multi-functional glycoprotein secreted by most epithelial cells and is involved in the organization of the perivascular matrix. TSP-1 blocks all the functions of activated endothelial cells and strongly mitigates tumor growth and metastases, while its absence enhances these effects. Expression of TSP-1 correlates inversely with malignant progression in melanoma, lung, and breast carcinoma. The antiangiogenic effect of TSP-1 has potential as therapeutic for cancer but the many biological activities of TSP-1 make its use very difficult as a cancer therapeutic. TSP-1 has domains that bind to receptors such as two proteoglycan/sulfatide receptors, the integrin $\alpha v\beta 3$, CD36 and integrin associated protein (IAP). Given the recognition of these domains by various receptor proteins, they are targets of interest to develop potential therapeutic compounds with antiangiogenic activities. Brain specific angiogenesis inhibitor (BSAI), like TSP-1 also contains similar recognition domains for integrins.

In one additional embodiment, preferred peptides mimicking domains of TSP-1 and BSAI with terminal Cys residues forming disulfide bonds via oxidation of SH groups creating constrained cyclic structures include the sequences: SEQ ID NOs: 2, 3, 13, 23, 42, 89, 92, 93, and 213-215.

In yet another embodiment, peptides from this and other related groups are selected independently to create novel ligand-targeted multi-stereoisomer peptide-polymer conjugate compounds for the potential treatment of abnormal angiogenesis, cancer, and pathological conditions of the eye including age related macular degeneration, choroidal neovascularization, diabetic retinopathy, and macular edema. Glycogen Synthase Kinase-3 Beta Isoconfiguration-1 (GSK3 Beta)

The knowledge that lithium is used to treat mood and manic-depressive illness, as well as acute brain injuries like ischemia, and chronic neurodegeneration, which are attributed to decreased expression of neurotrophins like BDNF and VEGF is advantageous. However, its beneficial effects which include mood stabilization, behavioral amelioration, and neurogenesis are indirect; the drug inhibits glycogen synthase kinase-3β (GSK-3β), a serine/threonine protein kinase, which also promotes β-catenin-dependent transcriptional events. Furthermore, other antidepressants up-regulate expression of IGF-I which in turn up-regulates brain-derived neurotrophic factor (BDNF), its receptor TrkB, and GSK-3, which controls cell membrane signal-to-gene transcription/protein translation, cytoskeletal organization, neuronal polarity, and cell survival/apoptosis. Thus, the role of lithium on GSK-3 inhibition is complex since GSK-3β has many pleiotropic roles.

GSK-3 is regulated by different signaling pathways via phosphorylation, subcellular translocation, and interaction with other proteins and is enriched in the nervous system. In addition, GSK-3β is constitutively active in nonstimulated cells under the basal quiescent state, it continuously phosphorylates signaling molecules like glycogen synthase, transcription factors like β-catenin, translational initiation factor eIF2B, and structural proteins like tau, thereby keeping these GSK-3 substrates in an inactive state or promoting their degradation. Stimulation of a variety of receptor tyrosine kinases phosphorylate GSK-3α/3β; this phosphorylation event inhibits the catalytic activity of GSK-3α/3β, thereby turning on signaling pathways otherwise constitutively suppressed by GSK-3α/3β in nonstimulated quiescent cells. Thus, GSK-3β is of interest because its dysregulated hyperactivity is associated with insulin resistance, diabetes mellitus, tumorigenesis, inflammation, and neuropsychiatric and neurodegenerative diseases. β-Catenin is phosphorylated by GSK-3β, leading to its proteasomal degradation; lithium prevents GSK-3β-catalyzed phosphorylation of β-catenin, enabling β-catenin to accumulate and translocate to the nucleus, where it facilitates gene transcription.

It is clear, that GSK-3β/β-catenin pathway is the convergent therapeutic target of lithium and various classical neuropsychiatric drugs, ameliorating behavior, mood, anxiety, cognition, and neurogenesis. Although lithium inhibits GSK3, however, it is not effective for all psychiatry disorders. Controlled studies with this drug for the treatment of mania and bipolar depression, unipolar depression, schizophrenia, and schizoaffective disorder revealed that this drug is most effective in bipolar disorder, with minimal or no therapeutic effects in other neuropsychiatric disorders. However, there is no conclusive neurochemical data that this is the case. Therefore, given the pleiotropic roles of GSK3β, and the lack of full understanding on how lithium works including the pathophysiology of bipolar disorder, GSK-3β is a target to develop newer treatments for this disorder, and other neurodegenerative diseases of the brain like Alzheimer's disease. Drugs for Alzheimer's disease have not shown significant likelihood of success; hence the opportunity to develop innovative drugs for this unmet medical need.

In one embodiment, preferred peptides mimicking functional domains of GSK-3β including phosphorylation, substrate binding pocket, and ATP binding sites, which are essential for GSK-3 β function include the sequences: SEQ ID NOs: 63, 65-68, 70-72, 75-81, and 216-219.

In another embodiment, peptides from this and other related groups are selected to create novel ligand-targeted multi-stereoisomer peptide-polymer conjugate compounds for the potential treatment of neurodegeneration, Alzheimer's disease, and bipolar disease.

Prion and Alpha-Synuclein

Infectious agents called prions, the cause of fatal neurodegenerative disorders of mammals characterized by a pathological process mediated by an abnormal configuration of a physiological protein called prion, are important target for therapeutic intervention. Under certain circumstances, prion protein in nervous tissue assumes a formation rendering the protein resistant to normal physiological turnover processes. The abnormal prion accumulates in nervous tissue resulting in the typical spongiform changes. A prion is therefore a fatal infectious agent composed primarily of protein that affects the structure of the brain or other neural tissue. Prion has alpha-helical formation and resides on the surface of cell membranes; when it misfolds, acquires high beta-sheet content and assembles into rods that coalesce aggregating extracellularly within the central nervous system to configuration amyloid plaques, which disrupt the normal tissue structure. Diseases caused by prions in humans include Creutzfeldt-Jakob disease and Alzheimer's disease among others. PRNP, the gene for the normal protein, show mutations in all inherited cases of prion disease. The mutations change the normal protein into the abnormal configuration.

Parkinson's disease (PD), an age-related neurodegenerative disease, and characterized by a loss of dopamine neurons in the substantia nigra pars compacta coupled with proteinaceous inclusions in nerve cells and terminals, known as Lewy bodies and Lewy neurites, respectively, is an important target for drug intervention. PD pathology affects nondopamine neurons in the upper and lower brainstem, olfactory system, cerebral hemisphere, spinal cord, and autonomic nervous system. The cause of cell death in PD is unknown, but proteolytic stress with the accumulation of misfolded proteins is implicated. Lewy bodies are the hallmark of PD and are composed of aggregated proteins that include alpha-synuclein (NACP). Similar to prion, alpha-synuclein acquires a largely alpha-helical formation when it binds to cell membranes. When alpha-synuclein misfolds, it acquires high beta-sheet content and polymerizes into fibrils that are associated with the formation of Lewy bodies. Over-expression of alpha-synuclein alone can induce PD syndrome in animals and humans. Alpha-synuclein behaves like a prion, and thus PD seems to be a prion disorder. Since both prion and alpha-synuclein lead to a prion disorder, both proteins are target molecules of interest.

In one embodiment, preferred peptides mimicking domains of PrP, Alpha-synuclein blocking phosphorylation, and KTK repeats of NACP protein include the sequences: SEQ ID NOs: 34, 45-48, 64, 83-88, and 220-224.

In another embodiment, the peptides are designed with motives similar to the kringle domain repeats of plasminogen, to bind prion protein. Peptides from this and other related group are selected independently to create novel ligand-targeted multi-stereoisomer peptide-polymer conjugate compounds for the potential treatment of CJD, PD, Alzheimer's, and neurodegeneration.

NOGO Receptor (NgR), and Somatostatin

The knowledge that CNS neurons normally do not regenerate after damage due to inhibitors of axon regeneration in CNS myelin, since different proteins expressed on mature oligodendrocytes cause axonal growth cones to collapse and thus arrest further growth, is of high interest for therapeutic intervention. Neurotrophic factors and growth-associated proteins, which are expressed in injured peripheral nerves, are often absent in the adult CNS. Furthermore, proteoglycan-rich glial scar at the lesion site configurations a physical and molecular barrier to re-growth. Thus, a major goal in the search for therapies for spinal cord injuries (SCIs) is to develop drugs that promote both the regeneration of damaged axons and the restoration of synaptic contacts with their appropriate targets. The axon regeneration inhibitor Nogo is a myelin-associated neurite outgrowth inhibitor. Nogo, myelin associated glycoprotein, and oligodendrocyte myelin glycoprotein, are interesting targets to develop spinal cord injury therapeutics. Activation of NgR results in a decrease in cellular cAMP. Another protein of interest with a role in the hypothalamous region of the brain is somatostatin, a peptide hormone that regulates the endocrine system and affects neurotransmission and cell proliferation via interaction with G protein-coupled somatostatin receptors. Somatostatin is produced by neuroendocrine neurons of the periventricular nucleus of the hypothalamus, and exerts antiangiogenic activity against primary tumors and metastasis.

In one embodiment, preferred peptides mimicking a structural domain of NOGO receptor where two prominent clusters, the acidic and hydrophobic cavities are located include the sequences: SEQ ID NOs: 27, 94, 225-228, 256, and 257. The cyclo peptides are obtained by cyclization of the terminal Cys residues forming a disulfide bond.

In another embodiment, the sequence of these peptides are important for protein-protein interactions and with extensive well-packed receptor-ligand binding interfaces with polar residues linked in complementary electrostatic interactions, and thus this region offers unique structures for the binding of substrates and potential inhibitors. These peptides have terminal cys residues that form disulfide bonds via oxidation of SH groups creating compacted cyclic structures. One of the peptides (S3) mimics a domain of the C-termini region of the PrP protein. Peptides from this group and other related groups are selected to create novel ligand-targeted multi-stereoisomer peptide-polymer conjugate compounds for the potential treatment of spinal cord injury (SCI) and central nervous system (CNS) injury where axon regeneration and/or neurite outgrowth is required for functional recovery, and in the case of somatostain peptides, as anti-cancer agents.

HIV-1 gp120, gp41, p24, Protease, Reverse Transcriptase, Integrase, and Vif

HIV, an infectious pathogen, is a global health problem of unprecedented dimensions. The identification of effective inhibitors or a vaccine is an unmet medical need. The envelope glycoprotein gp120, integrase, reverse transcriptase, vif, and protease have sequences of interest that can be used to develop an inhibitor or a therapeutic-prophylactic.

In one embodiment, preferred peptides mimicking domains of the proteins gp120, gp41, p24, protease, integrase, reverse transcriptase, and Vif (derived from HIV Subtype B strain HXB2) include the sequences: SEQ ID NOs: 59-63, and 229-232.

In another embodiment, peptides from this and other related groups are selected to create novel ligand-targeted multi-stereoisomer peptide-polymer conjugate compound for the treatment of HIV/AIDS.

In one more embodiment, a selected group of additional peptides that can be used to create compounds targeting HIV proteins are listed in U.S. Provisional Application Nos. 61/213,345, and 61/213,548, and U.S. application Ser. No. 12/836,187. Each of these applications is incorporated herein by reference in its entirety.

Calcium-Dependent Protein Kinase-1 (PfCDPK1), UIS3 and Dihydrofolate Reductase-Thymidylate Synthase (DHFR-TS)

Malaria, caused by *Plasmodium falciparum* infections, is a global health problem affecting 500 million people worldwide annually resulting in about one million deaths per year. Thus, the need to develop an effective anti-malaria therapeutic vaccine is an unmet medical need.

In one embodiment, peptides mimicking short domains of calcium-dependent protein kinase-1 (PfCDPK1), a protein essential for parasite survival, and a domain of UIS3 protein, include the sequences: SEQ ID NOs: 44, and 233-235.

In another embodiment, the domains include ATP binding site, substrate-binding pocket and the calcium-binding site. UIS3 protein plays a central role in fatty acid/lipid import during the rapid parasite growth in hepatocytes. This protein has an alpha-helical structure that binds to one molecule of the lipid phosphatidylethanolamine. The parasite relies on host fatty acids for synthesis of its membranes.

In one additional embodiment, Dihydrofolate reductase-thymidylate synthase (DHFR-TS) occurs as a bifunctional protein in malaria. The two proteins fuse together to configuration a single polypeptide. DHFR-TS is an essential enzyme in folate biosynthesis and therefore a drug target of interest to identify peptide sequences that could be used to develop a therapeutic to prevent the conversion of dihydrofolate to tetrahydrofolate by DHFR.

In one more embodiment, preferred peptides mimicking the NADP and folate binding sites of DHFR, respectively, include the sequences: SEQ ID NOs: 236-239.

In yet another embodiment, peptides from this and other related groups are selected to create novel ligand-targeted multi-stereoisomer peptide-polymer conjugate compounds for the potential treatment of the malaria parasite.

Mersacidin, Cystatin C, and Pep5

*Staphylococcus aureus*, a gram-positive bacteria enclosed in a thick cell wall and associated with significant morbidity and mortality, is a pathogen responsible for diseases including pneumonia, endocarditis, and bacteremia. Methicillin-resistant *Staphylococcus aureus* (MRSA) is the most common cause of nosocomial infections. Thus NRSA is of medical relevance since methicillin resistance has originated in strains not associated with nosocomial environments and/or antibiotic exposure. *S. aureus* is limited by a single membrane that comprises negatively charged phospholipids. The bacterium is surrounded by a thick cell wall of peptidoglycan. The membrane provides a barrier of selective permeability and the cell wall protects the bacteria from environmental factors. Both structures are essential for cell survival and hence the opportunity to identify therapeutics that target the bacteria cell wall and membrane. Several proteins of interest include Mersacidin from *Bacillus* sp, Cystatin C from human, and Pep5 from *Staphylococcus epidermidis*. Mersacidin inhibits the transglycosylation of peptidoglycan biosynthesis of the cell wall and has a propeptide modified to the mature lantibiotic during biosynthesis. The sequence contains Abu (2-aminobutyric) residues that are replaced with Cys residues to maintain the ring structure, which confers chemical stability and proteolysis resistance of the peptide.

In one embodiment, preferred peptides mimicking domains of proteins in the cell wall of gram-positive bacteria, include the sequences: SEQ ID NOs: 52, and 240-243.

In another embodiment, peptide S1 mimics a domain of the antibacterial activity of human Cystatin C, a cysteine protease inhibitor of bacteria containing this protease. Peptide S2 mimics the antibiotic peptide Pep5 derived from *Staphylococcus epidermidis*. The bactericidal activity of Pep5 is towards gram + bacteria such as MRSA, and consists of depolarization of energized bacterial cytoplasmic membranes, initiated by the formation of aqueous transmembrane pores. This peptide in its natural configuration contains lanthionine-amino acids that form thioether bonds with Cys residues to form a cyclic structure. The lanthionine amino acids were replaced by Cys residues, which form disulfide bonds via oxidation of SH groups, which maintain the ring structure of the peptide further enhancing its stability and resistance to degradation. Peptide S3 forms a ring structure via thioether bonds with Cys residues. The lantibiotic amino acids were replaced with Cys residues to maintain the cyclic structure via disulfide bonds. Peptide S4 forms three site-specific disulfide bonds via oxidation of Cys residues. These peptides and peptides from related groups are selected to create novel ligand-targeted multi-stereoisomer peptide-polymer conjugate compounds for the potential treatment of MRSA, the bacteria responsible for nosocomial infections.

Peptide-2 LEAP-2 and Defensin

Salmonella typhimurium, a pathogenic Gram-negative bacteria predominately found in the intestinal lumen, is a target of interest. Its toxicity is due to an outer membrane consisting largely of lipopolysaccharides (LPS) which protect the bacteria from the environment. The LPS is a polysaccharide core, and lipid A, which is made up of two phosphorylated glucosamines, which are attached to fatty acids. These phosphate groups determine bacterial toxicity, and the antigen being on the outermost part of the LPS complex is responsible for the host immune response. S. typhimurium undergo conformational changes by acetylation of its antigen, making it difficult for antibodies to bind. S. typhimurium infects by coming in direct contact with nonphagocytic cells. This contact induces the formation of appendages on the bacterial cell surface causing host cytoskeleton to rearrange and allowing the bacteria to enter the cell causing gastroenteritis that lead to diarrhea.

In one embodiment, preferred peptides mimicking short domains of peptide-2 LEAP-2 and defensins with potential inhibitory effect against Gram + and − bacteria, yeast, virus and fungi, include the sequences: SEQ ID NOs: 18, 51, 53, and 244-246.

In another embodiment, these peptides may be useful to target the cell membrane through pore formation enhancing permeation and therefore damaging the membrane and killing the pathogens. Peptides from this and other related group are selected to create novel ligand-targeted multi-stereoisomer peptide-polymer conjugate compounds for the potential treatment of Salmonella.

Acyl Carrier Protein Synthase (Acps)

Tuberculosis (TB) is caused by Mycobacterium tuberculosis (Mtb) claiming the lives of millions of people each year, and with about one third of the world's population already infected with Mtb. Fatty acid synthesis and their elongation to mycolic acids, the hallmark of mycobacterial cell wall, is an essential process for bacteria survival. The acyl carrier protein synthase (AcpS) is a protein comprised of three asymmetric monomers. This protein activates two distinct acyl carrier proteins (ACP-1 domain and the mycobacterial AC-II protein) that are present in fatty acid synthase systems FAS-I and FAS-II, respectively. AcsP binds to ACP-1 and ACPM through different amino acid residues and interactions. The structural characteristics of Mtb AscP protein and the mode of interaction with ACPM and FAS-I are essential for Mtb viability; thus, the protein is a target for the development of drugs. The de novo biosynthetic pathway to pantothenate is present in many bacteria, fungi, and plants and comprises four enzymes, encoded by panB, panE, panD, and panC. This protein and the pantothenate pathway are therefore attractive target for inhibitors that could provide lead compounds for novel anti-TB drugs. Since no panF homologues have been identified in Mtb, TB cannot acquire pantothenate from the environment. The absence of these enzymes in mammals further suggests that inhibitors could be selective with a reduced risk of side effects.

In one embodiment, preferred peptides mimicking functional domains of ACp for CoA binding, and the catalytic site of substrates and products important for pantothenate synthetase enzyme catalytic mechanism, include the sequences: SEQ ID NOs: 247-250.

In one more embodiment, peptide S1 mimics the site for CoA binding, and the site for salt bridge formation, as well as the binding interaction sites of ACP-II and ACPM proteins. The remaining peptides mimic the catalytic site of substrates and products important for pantothenate synthetase enzyme catalytic mechanism. These peptides are cyclized to enhance their stability and resistance to degradation. Peptides from this and other related groups are selected to create novel ligand-targeted multi-stereoisomer peptide-polymer conjugate compounds for the potential treatment of Mtb infections, the causal agent of tuberculosis.

In one additional embodiment, all the peptide sequences disclosed in this specification illustrate the advantages of the present invention and are not intended in any way otherwise to limit the scope of the peptides of this invention since any important functional domain of any protein involved directly or indirectly in any disease can be used to select mimicking peptides or motifs of interest to target the protein directly or allosterically and create the multi-targeted compound of this invention. In any case, the function of the plurality of the stereoisomer peptides in the novel compound is to block, interfere, or inhibit simultaneously and independently the function of the target protein (antagonism) or to positively enhance a protein that initiates a response when interacts with another protein (e.g., receptor) inhibiting the target protein (agonism).

Properties of the Peptides of the Invention

In one embodiment, any peptide selected as target for a particular target protein, is not a natural peptide (L-peptide) but rather a peptide that is synthesized in its stereoisomer form with D-amino acids, D- and rare or unnatural amino acids or D-, L- and rare or unnatural amino acids, with retro-inverso and inverso configuration, and with linear or cyclic compact structure giving rise to alternative stereo-chemistries, which will be readily appreciated by those of skill in the art.

In other embodiment, is worth nothing that natural L-peptides in spite of playing a central role in every cell in the body, and being effective drugs to target extracellular receptors, and have been used to modulate intracellular processes; they are inherently unstable within the body, are rapidly broken down into inactive fragments by protease enzymes, lack the ability to enter cells, and are filtered from the blood stream by the kidneys within minutes. Therefore, L-peptides therapeutic potential is hampered by their rapid degradation in the body, and the reason they are not developed as therapeutics. On the other hand, the stabilization of peptide analogs such as the stereoisomer peptides and compounds comprising the composition of matter of this invention can be carried out by means of targeted chemical modifications to confer enzymatic-resistance to a peptide. Modifications include N-terminal acetylation, C-terminal amidation, alkylation of the peptide bond nitrogen, cyclization, residue side-chain modifications, change in chirality, and replacement of the peptide bond by other chemical groups. Thus, peptides containing D- and L-; D-, L-, and rare or unnatural amino acids or only D-amino acids including changes in their orientation (i.e., inverso and retro-inverso) and with compact cyclic configuration strongly resist enzyme degradation, have extended shelf-life, and lead to higher potency and longer circulation in the body. In addition, their changes in chirality do not affect their biological activity. Their stability can be further enhanced by coating or encapsulating a plurality of these peptides with hydrophilic or hydrophobic polymers. The addition of unnatural or rare amino acids (raa) further enhances the stability of the peptides.

In one more embodiment, the stereoisomer peptides containing D- and L-; D-, L-, and rare or unnatural amino acids or only D-amino acids including all their analogs with different orientations differ in their spatial arrangement of the atoms in their molecule. Peptides with D-amino acids are the mirror image of their counterparts with L-amino acids. Only peptides with D-amino acids or combined with unnatural anibo acids are assembled in both inverso and retro-inverso orientations to obtain inverso D-peptides, and retro-inverso D-peptides. These enantiomer or stereoisomer peptides can be linear or cyclic and the cyclic stereoisomer peptide may have bridges created by head-to-tail cyclization, by disulfide bonds with two terminal cysteine residues, a lactam bridge (amide bond formation) between the γ-carboxyl group (COOH) of the side chain of a terminal amino acid, and the ε-amino ($NH_2$) group of a side chain of a terminal lysine, and thioether bonds formed between a cysteine side chain and the side chain of a serine or a threonine. Thus, cyclic peptides have S—S, C=ONH, RC=ONR$_2$ or R—S—R bonds. In this invention, any stereoisomer peptide may have a combination of D-amino acids and rare amino acids, or only D-amino acids; and the cyclic structure may have any type of bond that has been created by linking terminal residues, terminal and core residues, or only core residues of the peptide.

In other embodiment, rare or unnatural amino acids are selected from the group consisting of Sar, Nle, Ile, Nvl, NMe-Val, NMe-Leu, NMe-Nle, Cpg, Chg, Hyp, Oic, Igl, Aib, Aic, Pip, BhTic, BhPro, Tiq, Nip, Thz, Thi, 4GuaPr, 4Pip, Idc, Bip, me-Tyr, I-Tyr, Igl, BhTic, BhPhe, AMeF, BPhe, Phg, Anc, Atc, NMe-Phe, NMe-Lys N, hPhe, BhTrp, pI-Phe, Aic, NMe-Lys Orn Dpr 2 Dbu N-eMe-K, N-eEt-K, N-eIPr-K, bhomoK, Acm, Ahx, K(NPeg11), K(NPeg27), Cit, hArg, hCit, or NMe-Arg. They are readily available commercially and can be incorporated during synthesis of the stereoisomer peptides.

In one additional embodiment, stereoisomer peptides comprising D-amino acids in their retro-inverso configuration with cyclic compact structures and their analogs and derivatives have very high stability. This property makes the stereoisomer peptides useful therapeutics for medical applications. Furthermore, if a plurality of different specific stereoisomer peptides are conjugated to a biocompatible polymer and further encapsulated inside polymer particles (e.g., nanoparticles), they are not only held together within the particulated carrier, but become even more stable. In addition, conjugation of a stereoisomer peptide-ligand to a surface of a particulated polymer carrier further enhances the specific delivery of the encapsulated plurality of different stereoisomer peptides to specific tissues, cells, or cell compartments.

In one more embodiment, it is emphasized that both chiral changes and end terminal protection or peptide cyclization creates stereoisomer peptides that are resistant to proteolysis and can readily be conveniently administered by several routes including the oral, parenteral, topical, transdermal or mucosa. Furthermore, peptide chirality is not necessarily required for biological activity or for peptide-peptide interactions within the membrane environment. Thus, they exert their biological activity like their natural counterparts (L-configurations) do. In addition, since peptides with D-amino acids are not degraded by proteases (i.e., resistant to hydrolysis), further provides potential for oral bioavailability, since they have extended persistence in circulation, long shelf life, and can be used in harsh mucosal environments, including the stomach or as a topical therapeutic.

In one additional embodiment, is worth nothing that the body has many peptidases. Thus, natural and synthetic peptides with L-amino acids completely lack the stereoisomer peptide's properties in vivo. In fact, peptidases break peptide bond in L-peptides by inserting a water molecule across the bond degrading the L-peptides in a manner of a few minutes or less in the body, and some peptidases are specific for certain types of L-peptides, making their degradation even faster. Thus, if an L-peptide is used as a therapeutic agent, its activity is quickly reduced as the L-peptide degrades in the body by the action of peptidases rendering the L-peptide useless.

In a preferred embodiment, stereoisomer peptides have D-amino acids in their retro-inverso configuration with cyclic compact structures. Their enhanced physicochemical and biological properties make them highly suitable to develop unique and novel stable drugs for therapeutic use. In this invention, the novel and unique stable therapeutic is a ligand-targeted multi-stereoisomer peptide-polymer conjugate compound.

Protecting Carboxy- and Amino-Terminal Groups

In one embodiment, this invention provides linear stereoisomer peptides with modified N- and C-terminal group using standard chemistries. Chemically synthesized peptides carry free amino and carboxy terminal groups, being electrically charged in general. In order to remove this electric charge to prevent interactions with other peptides and/or proteins, especially in vivo, peptide ends are modified by N-terminal acetylation using an acetyl group, and/or C-terminal amidation using an amide group. These modifications mimic a peptide bond at the end of the peptide, further increasing their stability to proteases and further yielding enhanced pharmaceutical properties. The N-terminal group, however, is deprotected after synthesis when the peptide is conjugated to a linker that in turn is conjugated to an activated group of a polymer. Furthermore, both C- and N-terminal groups are not protected when the stereoisomer peptide is cyclized. One can also modify the amino and carboxy terminal residues of the stereoisomer peptides to produce derivatives. A wide number of other protecting groups are suitable for this purpose. Particularly preferred carboxyl protecting groups include amides, carboxyamidase, amidase esters, and ether-forming protecting groups. Amino protecting groups include acetic acid or halogenated to obtain a derivative thereof.

In another embodiment, peptides can also be modified to obtain a derivative thereof such as alpha-chloroacetic acid, alpha-bromoacetic acid, or alpha-iodoacetic acid, or by phosphorylation. Those of skill in the art will recognize that a variety of techniques are available for constructing compounds with the same or similar biological activity but with favorable characteristics in regard to their solubility, stability, and susceptibility to hydrolysis and proteolysis.

In other embodiment, an acetyl group is used to protect the amino terminus and an amide group is used to protect the carboxyl terminus during synthesis. Preferably, acetylation is accomplished during the synthesis when the peptide is on the resin using acetic anhydride. These blocking groups also enhance the alpha-helix-forming of the peptides that have this particular structure. In this invention, the stereoisomer peptides are synthesized with protected side chains and protected terminal ends if they are used in their free forms. Stereoisomer peptides that are conjugated to a polymer via a linker, however, have their amino group unprotected after synthesis to allow for coupling of the amino group of the stereoisomer peptide to the activated ONp (paranitrophenyl group) of a linker attached to a polymer, or the activated carboxyl group of a polymer.

Stereoisomer Peptides

In one embodiment, the stereoisomer peptides of the invention refer to an artificial sequence that is synthesized with L-, D-, and unnatural amino acids, D- and unnatural amino acids, or with all D-amino acids. This gives rise to alternative stereochemistries, which will be readily appreciated by those skilled in the art. These stereoisomer peptides have two topological configurations represented by inverso D-peptides which are the mirror image of L-peptides and therefore they do not overlap, and by retro-inverso D-peptides which retain the original spatial orientation of all side chains as in the L-peptides. Retroinverso peptides overlap with their L-counterparts and are synthesized in the reverse order.

In other embodiment, the characterisitics of the compounds provide adequate physichochemical properties given their high stability and resistance to degradation by proteases present in human fluids (blood and serum), extended persistence in blood, and longer shelf life. These physichochemical properties further provide ideal biopharmaceutical properties such as reduction or elimination of immunogenicity; administration by the oral or mucosal routes, and enhanced biological activity given the high degree of stability.

Peptide-Ligands

In one embodiment, preferred peptide-ligands for use with conjugates of the invention are specific peptides that bind with high affinity to receptors, hormones, cytokines, enzyme substrates, viruses, proteins and a variety of other macromolecules. The peptide-ligand and their analogs, may also antagonize or modulate the physiological action of the natural ligands of the macromolecule (i.e., proteins) directly (competitive) or indirectly (allosteric). Thus, they are useful to guide the delivery of drugs to targeted sites. The peptide-ligand is a transduction domain peptide (e.g., Tat TD), a cell penetrating peptide (e.g., penetratin), a permeation peptide that cross the blood brain or retina barrier, a transport peptide (e.g., transportan), or a chemotactic peptide. Peptides of this type are found in receptors, hormones, cytokines, growth factors, kinases, and many enzyme substrates and other proteins like chaperons. The antagonistic effect of these peptides may include inhibitory activities. Suitable peptide-ligands have inhibitory, modulatory and activating functions and include but are not limited to Tat TD, transportan, penetratin, tyrosine kinase antagonists, angiogenesis inhibitors; apoptosis regulators; bFGF inhibitor; cartilage derived inhibitor; kinase inhibitors, IGF-1 receptor inhibitor, interferons and their agonists, interleukins, VEGF ligand, lytic peptides, MMP inhibitors, signal transduction inhibitors, signal transduction modulators, somatomedin binding proteins, splenopentin, spongistatin, squalamine, urokinase, GnRH I and II, somatostatin, transferring, melanotropin, ApoE, Willbrand's factor, EGF, RGD and CCK peptides, heparin, plasmin inhibitor, platelet factor-4, beta-amyloid peptides, delta-opioid antagonists, opiod peptides, neuropeptides, brain derived peptides, chemotactic peptides, chemokine peptides, antimicrobial peptides, TSP-1 receptor, pituitary adenylyl cyclase type I, bombesin, KISS peptides, heparin, urotensin II peptides, octreotide, depreotide, vapreotide, vasoactive intestinal peptide (VIP), cholecystokinin (CCK), RGD-containing peptides, melanocyte-stimulating hormone (MSH) peptide, neurotensin, calcitonin, peptides from complementarily determining regions of an antitumor antibody, glutathione, YIGSR (leukocyte-avid peptides, e.g., P483H, which contain the heparin-binding region of platelet factor-4 (PF-4) and a lysine-rich sequence), atrial natriuretic peptide (ANP) and platelet factor-4, beta-amyloid peptides, delta-opioid antagonists (e.g., [$^{125}$I]TTIPP(psi) [H-Tyr(3'I)-Ticpsi[CH2NH]Phe-Phe-OH]; annexin-V, endothelin, interleuking (IL)-1, IL-1ra, IL-2, and IL-8, leukotriene B4 (LTB4), chemotactic peptides (e.g., N-formyl-methionyl-leucyl-phenylalanine-lysine (fMLFK)), bitistalin, pituitary adenylyl cyclase type I receptor (PAC1), fibrin α-chain, chemotactic peptides, GP IIb/IIIa receptor antagonists (e.g., DMP444), epidermal growth factor, human neutrophil elastase inhibitor (e.g., EPI-HNE-2 and EPI-HNE-4), plasmin inhibitor, antimicrobial peptides, apticide (e.g., P280 and P274), thrombospondin receptor and TP-1300 analogs, pituitary adenylyl cyclase type I and those derived from phage display libraries and their substitutions. The peptide-ligand of this invention is also a stereoisomer peptide.

Peptide Synthesis

In one embodiment, the peptides of the invention may be prepared by classical chemical synthesis methods. Solid phase synthesis is typically commenced from the C-terminal end of the peptide using an alpha-amino protected resin. After initial coupling, the alpha-amino protecting group is removed using trifluoroacetic acid (TFA) or hydrochloric acid (HCl) solutions in organic solvents at room temperature. Thereafter, alpha-amino protected amino acids are successively coupled to a growing support-bound peptide chain. The alpha-amino protecting groups, including protection of side chains, are those known to be useful in stepwise synthesis of peptides, and include a variety of protecting groups well known in the art. After the desired amino acid sequence has been completed, the desired peptide is decoupled from the resin support by treatment with a reagent, such as trifluoroacetic acid (TFA) or hydrogen fluoride (HF), which not only cleaves the peptide from the resin, but also cleaves all remaining side chain protecting groups.

In another embodiment, the chemical synthesis of peptides with D-amino acids is similar to the synthesis of peptides with L-amino acids. The purification process is carried out using standard HPLC, or by dialysis. D-amino acids with L- and/or unnatural amino acids or only D-amino acids are incorporated at one or more positions in the peptide simply by using a D-configuration or an unnatural derivatized amino acid residue in the chemical synthesis. D-amino acid residues and unnatural amino acids for solid phase peptide synthesis are commercially available from a number of suppliers. The D- and unnatural amino acids, or only D-amino acids are incorporated at any position in the peptide to obtain the desired stereoisomer peptide.

Retro-Inverso D-Peptides Stability and Synthesis

In a preferred embodiment, retro-inverso peptides contain only D-amino acids assembled in the reverse order of their parent L-sequences. These peptides have the properties of retaining the protein bioactivity, are long-lasting proteolitically, and share the antigenic mimicry of their L-counterparts. Essentially, retroinverso peptides are a structural mimic of the parent peptide, and are immune to proteolytic attack since the peptide is entirely stable in human plasma, serum, and tissue.

In another preferred embodiment, retroinverso peptides are synthesized using the same methods to synthesize their L-counterparts; however, there are many variations, and the variation in the method depend on the type of modifications, group protection, and/or the addition of unnatural amino acids in the sequence of the D-peptide and its orientation. For example, one synthesis approach is to create a malonate derivative using tert-butoxycarbonyl (Boc) chemistry on a p-methylbenzhydralamine resin. Assembling of the protective peptide chain can be carried out at the 100-mmolscale using a neutralization protocol. The R,S)-2-isobutylmalonic acid monobenzyl ester is incorporated in the peptide chain as a recemate generating a pair of diastereoisomers. The peptide is cleaved from the resin with HF (anhydrous hydrogen fluoride) in the presence of anisole and 1,2-ethanedithiol. The HF is removed in vacuo; the crude peptide is eluted from the resin, lyophilized and purified by preparative HPLC and identified according to the retention time. The purity of the retro-inverso peptides (>85%) is assessed by analytical HPLC using a TFA gradient in acetonitrile and its identity is determined by MALDI-MS (matrix-assisted laser desorption ionization mass spectrometry). Amino acid analysis is carried out to determine the content of the synthetic peptide.

In one embodiment, retroinverso peptides can be synthesized employing isocyanates of Na-Fmoc-amino acids/peptide acids catalyzed by DMAP. In a typical reaction Fmoc-amino acid azides are prepared by generating a mixed anhydride of Fmoc-amino acid and then reacted with $NaN_3$. The resulting azide is then dissolved in toluene and subjected to Curtius rearrangement. After evaporation of toluene under reduced pressure, the azide is dissolved in DCM and a mixture of Boc-/Z-/Bsmocamino acid and a catalytic amount of DMAP are added at 0° C. with a 30 min stirring followed by stirring for additional 2 hours at RT. The product is then isolated by recrystallization generating high yields (70-92%). This method can also be applied to Fmoc-peptide acids and the entire course of the reaction can be completed in about 4 hours. The retro-inverso peptides are isolated by recrystallization and then characterized by mass spectroscopic measurements and other techniques like 1H NMR, 13C NMR, and amino acid analysis.

In a preferred embodiment, the synthesis of retro-inverso peptides is carried out using standard solid-phase synthesis methods but with D-isomers and/or unnatural aminoacids. At the N-terminus, a lysine may be added for later use (i.e., conjugation to a polymer) and the epsilon amine group is protected by acetylation. Once peptide synthesis is complete, the N-terminal Fmoc group is removed to uncover the N-terminal amine and the protected peptide containing a C-terminal carboxyl is cleaved from the Cl-trt resin (see Example 1).

In another preferred embodiment, the peptide fragments containing the free N-terminal amine and C-terminal carboxyl are cyclized head-to-tail to obtain the constrained cyclic structure of the peptide The cyclo peptide is then cleaved from the resin and purified using preparative HPLC columns. Fractions that meet purity requirements are lyophilized and stored at −80° C. Amino acid analysis is utilized to determine the net amount of the peptide, and the purified peptide is converted to the acetate salt, lyophilization, and storage until used (see Example 1).

Stereoisomer Peptides with Linear Structure

In one embodiment, some of the amino acid sequences selected have linear structure forming a combination of H-helix, beta-sheet, and C-coil structure, which negative or positive charge, and with only a few hydrophobic residues. In this case, the short sequence may specifically target a substrate site or the binding pocket of a substrate, and the Cys residues, when present may not necessarily form disulfide bonds. Peptides with alpha-helix have a net positive charge, and a percentage of the hydrophobic residues located on one side of the chain, with both hydrophobic and hydrophilic amino acids forming an amphipathic-helix. Proteins with helices usually have a modulating activity like human cathelicidin and bacterial Gramicidin A.

In a preferred embodiment, the peptides with amino acids arranged in the alpha-helix configuration have the property to bind and permeate the negatively charged membranes and therefore are useful as therapeutics, since they readily penetrate cell membranes. Peptides with similar configuration but containing stereoisomer amino acids are designed from the protein of interest to enhance their therapeutic properties. Although these peptides are linear, only those with alpha-helix require maintaining the original linear structure in order to retain their biological activity. However, peptides with both alpha-helix and beta-sheet can be cyclized to stabilize the chains, specially the alpha-helix, increasing their stability and without losing their biological activity. This approach makes these peptides even more valuable for pharmaceutical and therapeutic purposes.

Stereoisomer Peptides with Cyclic Structures

In one embodiment, disulfide bridges are an important subject matter of this invention since the stereoisomer peptides may contain one, two, or three intramolecular disulfide bonds that are formed by oxidation of the Cys residues by pairing the desired Cys residues through the SH groups present in the sequence of a particular synthetic stereoisomer peptide. The control of Cys bond formation is exercised by choosing an oxidizing agent of the type and concentration effective to optimize formation of the desired disulfide bond, especially when the peptide has more than 2 Cys residues. In general oxidation is carried out chemically using a catalyst (see Example 2).

In another embodiment, cyclization by disulfide bond of highly purified stereoisomer peptides whose purification has been validated by HPLC and ESI-MS or MALDI-TOF, can be carried out using either ferricyanide assisted cyclization or glutathione assisted oxidation reactions.

In one additional embodiment, the rigidity of the cyclic peptide depends upon the number of disulfide bonds, which is determined by the number of Cys residues present in the peptide chain (2, 4, or 6) creating single, double or triple intra-molecular disulfide bonds via oxidation of their SH groups, to obtain cyclic constrained structures. The higher the number of Cys residues in the peptide, the more compact is the structure. This property makes the cyclo peptides highly stable and therefore potentially affecting, the function, folding, or interaction of the target protein with high affinities.

Cyclization of Stereoisomer Peptides by Amide Bond Formation

In one embodiment, other non-disulfide peptide cyclization strategies are employed, especially when cyclization is carried out with residues that are not Cys residues. The cyclization of peptides is achieved by the covalent chemical bond formed between the terminal amino acids of the peptide, where the carboxyl group termini of one amino acid reacts with the amino group termini of the other amino acid causing the release of a molecule of water and creating an amide bond. This linking is also known as head-to-tail linking of the terminal amino acids creating the amide bond; also known as peptide bond. It is advantageous also to incorporate a Lys residue to the cyclized peptide to conjugate the preferred polymer to the available ϵ-group of the Lys residue.

In another embodiment cyclization of peptides can also be carried out by lactam bond formation which is also an amide bond. This bond is created between the side-chain of the amino acid lysine with the side-chain of the amino acids glutamate or aspartate. The amide and lactam bonds are important structural features to cyclize peptides, to stabilize alpha helices, or to substitute for the less-stable disulfide bonds. Cyclo peptides created in this manner also have the molecular rigidity necessary to enhance their physicochemical and pharmaceutical properties.

In one additional embodiment, the peptides may have in their core sequence Cys residues that are cyclized by replacing one Cys residue with lysine and the second Cys residue with glutamic acid. Thereafter a cyclic peptide may be formed through an amide bond (i.e., lactam bond) between the side chains of these two residues. Alternatively, a peptide may be synthesized wherein one Cys of the core sequence is replaced with lysine, or serine. A cyclic peptide may then be formed through a thio-ether linkage between the side chains of the lysine (or serine) residue, and the second Cys residue of the core sequence. As such, in addition to disulfide cyclization strategies, amide and thio-ether cyclization strategies can be readily used to cyclize the stereoisomer peptides. Alternatively, the amino-terminus of the stereoisomer peptide can be capped with an alpha-substituted acetic acid, wherein the α-substituent is a cleaving group, such as an alpha-haloacetic acid, for example, alpha-chloroacetic acid, alpha-bromoacetic acid, or alpha-iodoacetic acid.

In one more embodiment, cyclization of helical peptides is done directly by head-to-tail or by creating small cycles adjacent to amino acids of interest. For example, if the residues form an alpha-helix, the helical structure can be stabilized by creating a cyclic peptide by linking the N-group of one terminal residue with the C-group of the other terminal residue creating a peptide bond. If the peptide has a small motif with alpha-helix structure, this chain can be stabilized by cyclizing the side chains of adjacent amino acids (near the motif of interest) creating a lactam bond. In both cases an amide bond is created. Another method to stabilize helices in peptide chains is to incorporate a short ethylene-glycol based linker [e.g., N-(Fmoc-8-amino-3,6-dioxaoctyl) succinamic acid] that results in a conformational change of the peptide from random coil to an alpha-helix.

Linkers Coupled to Peptides for Conjugation with a Polymer

In one embodiment, cyclic or linear stereoisomer peptides may be coupled to a linker during synthesis or the linker may be coupled to a single polymer chain or to a branch of a polymer via conjugation. A linker conjugated to an activated group of a single polymer chain or a branch of a polymer is useful to determine the cellular transport, clearance, cleavage or release of the linked stereoisomer peptide in the target tissue, cell or sub-cellular location and can serve as initiation site that enables binding to one or more other molecular moieties. The addition of linkers is achieved by synthesis methods well established in the art. The linker may contain two or more amino acids preferably selected from D-Lys, D-Gly, D-Phe, D-Leu, D-Ser, D-Tyr, D-Glu, D-Gln, and D-Asn. The selected residues are preferably D-amino acids and have groups suitable for attachment to the target functional groups of a polymer, either pre-activated or in the presence of a suitable coupling reagent. The linker may contain between 2 to 5 amino acids and the functional group of a terminal amino acid may be reacted with the target single branch or multiple branches of the pre-activated polymer. In the case of Lys the functional ε-amino group reacts with the pre-activated polymer to attach the linker which is subsequently used to attach a linear or a cyclic peptide by covalent bond creating an amide link.

Polymers

In one embodiment, polymers are used to create compounds to deliver drugs to tissues, cells, or cellular compartments (i.e., cytosol). The polymer is selected from a group consisting of polylactide, polyglycolic acid (PGA), polylactic acid (PLA), polyhydroxy acids (PHAs), poly lactic-co-glycolic acid (PLGA), polyethylene Glycol (PEG), and branched PEG, polyvinyl acetate, polyvinyl alcohol, α, β, poly(N-hydroxyetheyl)-DL-aspartamide (PHEA), α, β, poly (N-hydroxypropyl)-DL-aspartamide (PHPA), poly-N-(2-Hydroxypropyl) methacrylamide (HPMA), and HPMA copolymers, polyethylenimine (PEI), polylysine, poly(aspartic acid, poly(L-lysine), poly(L-glutamic acid), L-Phenylalanine-based poly(ester amide)s, Tyrosine-derived polycarbonate, L-Tyrosine-polyphosphate, Poly(L-lactide-b-g-benzyl glutamate), Poly(ester-imide)s incorporating L-alanine, Poly (amide-imide)s using L-lysine, L-methionine based poly(ester amide)s, L-Arginine based poly(ester amide)s, L-Phenylalanine based poly(ester amide)s, L-Alanine based poly (ester amide)s, L-Valine based poly(ester amide)s, L-Leucine based poly(ester amide)s, L-Isoleucine based poly(ester amide)s, L-Norleucine based poly(ester amide)s, D-,L-methionine based poly(ester amide)s, Poly(butylenes adipate), a-Hydroxy acids derived from amino acids and combined with glycolic acid, lactic acid, and 6-hydroxyhexanoic acid, Copoly(amino acid)s based on 6-aminocaproic acid and L-proline, poly(ether ester amide)s, 4-hydroxyproline; Z-Lys, 8-(benzyloxycarbonyl)-L-lysine; L-Glu(OBzl), γ-benzyl-L-glutamic acid; β-benzyloxycarbonyl-L-cysteine; γ-benzyl-L-aspartic acid; β-methoxybenzyl-L-cysteine; O-benzyl-L-serine; PLAL, poly(LLA-co-Lys); poly(N-isopropylacrylamide), poly-R,β-[N-(2-hydroxyethyl)-L-aspartamide]; poly(DLLA-co-4-hydroxyl-L-proline); poly(ester amide); poly(ether ester amide); poly(ester amide) with unsaturated backbone; poly(ester-co-urethane); (poly(ε-caprolactone), poly(alkyl cyanoacrylates), poly(isobutylcyanoacrylate, ethyl cellulose, cellulose acetate phthalate, polyvinyl alcohol, Poly(styrene), Poly(vinylpyridine), Poly(β-hydroxybutyrate), poly(butylcyanoacrylate), Poly(alkyl methacrylate), poly(fumaric anhydre)/poly(lactide-co-glycolide), sodium alginate, double coated nanoparticles: tween 80 and PEG 20000 poly(butylcyanoacrylate), Pluronic polymeric micelles, and the natural polymers albumin, casein gelatin, alginate, collagen, chitosan, and derivatives thereof. PLGA, PLA, and Poly ε-caprolactone are FDA approved polymers.

In another embodiment, polylactide and poly lactic-co-glycolic acid (PLGA) are typically used to provide sustained drug delivery for a determined period of time. Poly(lactic acid) and polyethylene glycol are suitable for controlled parenteral drug delivery system. Other delivery systems that are used may include liposome based-drug delivery carriers, nano-particles based on di-stearoyl phosphatidyl choline (DSPC), cholesterol, dioleoyl phosphatidyl ethanolamine (DOPE), and di-stearoyl phosphatidyl ethanolamine (DSPE)-mPEG2000 conjugated to the target molecule.

In a preferred embodiment, the polymers to create the compounds of this invention are poly lactic-co-glycolic acid (PLGA), polylactic acid (PLA), Poly ε-caprolactone, N-(2-Hydroxypropyl) methacrylamide) (HPMA), HPMA co-monomers, Pluronic polymeric micelles (PPM), and polyethylene Glycol (PEG). Each different stereoisomer peptide from a plurality of stereoisomer peptides and a peptide-ligand are independently and separately conjugated to a functional group of a single polymer chain or to a separate branch of the polymer either directly or via cleavable or no-cleavable linkers, respectively, depending on the polymer, and then conjugated all together by polymerization or by encapsulation in the polymer to create novel ligand targeted multi-stereoisomer peptide polymer-conjugate compounds. These compounds, created for the first time, can be formulated for different administration routes and used in the anti-diseases strategies described here.

Polymers as Carrier for Drugs

In one embodiment, this specification provides for the first time novel therapeutic compounds for treating a variety of diseases utilizing specific ligand-targeted multi-stereoisomer peptide polymer conjugate compounds. Thus, any disease state amenable to treatment with the compounds is addressed by providing novel therapeutic compounds as shown in this specification.

In another embodiment, a biodegradable polymer (i.e., PLGA) is capable of being cleaved into biocompatible byproducts through chemical or enzyme-catalyzed hydrolysis in the body. This biodegradable property is what makes possible to use them conjugated to stereoisomer peptides since they do not accumulate in the body. If the polymer is not biodegradable (i.e., HPMA), it can be excreted via the urine, as long as their molecular weight does not exceed the glomerular size to allow their body excretion from the kidney to the urine and out from the body. Another advantage is that stereoisomer peptides conjugated to hydrophilic or hydrophobic and degradable and/or biocompatible polymers can be released in a controlled manner; i.e., the stereoisomer peptide concentration in the target site (tissues or cells) is maintained within the therapeutic window. The release rates of the stereoisomer peptides from polymers can be controlled by a number of factors, such as biodegradation, degradation of linkers in the case of non-biodegradable polymers, the kinetic of the polymers. In this particular invention, the high stability of the stereoisomer peptides, allow longer retention time of the stereoisomer peptides in the body.

Polymer Based Compounds of the Formula ([sP]n(L)-[Pol]-$P_L$).

In one embodiment, compounds of the formula ([sP]n(L)-[Pol]-$P_L$), named ligand targeted multi-stereoisomer peptide-polymer conjugates compounds, for potential use as therapeutics for the treatment of a variety of human diseases are polymer based compounds. The polymer is selected from the group comprising poly lactic-co-glycolic acid (PLGA), poly-lactide Acid (PLA), Poly ϵ-caprolactone (PLC), poly-N-(2-Hydroxypropyl) methacrylamide (HPMA), HPMA co-monomers, Pluronic polymeric micelles (PPM), and polyethylene glycol (PEG). In this invention, the preparation of such conjugates including their encapsulation in nanoparticles of a polymer carrying a peptide-ligand conjugated on the surface of the polymer nanoparticles for targeted delivery is exemplified with the polymers PLGA and HPMA, as described in the proceeding sections of this specification.

PLGA Polymer

In one embodiment, to illustrate this invention, poly(lactic-co-glycolic acid) (PLGA), a biodegradable and biocompatible FDA approved polymer (e.i., co-monomer), is used to create a PLGA conjugate compound. PLGA is synthesized by random ring-opening co-polymerization of the monomers glycolic acid and lactic acid to create PLGA. This polymer is readily dissolved compared to their monomers by a wide range of common solvents, including acetone, ethyl acetate, chlorinated solvents and tetrahydrofuran.

In other embodiment, degradation of PLGA occurs by hydrolysis of its ester linkages in the presence of water, and depends on the monomers' ratio used in production. The higher the content of glycolide units, the lower the time required for degradation. A PLGA copolymer with 50:50 monomers' ratio has the faster degradation time of about two months. The polymer degradation time can also be tailored by altering the ratio of lactic acid and glycolic acid during synthesis. This is important for the manufacturing nanoparticles. PLGA polymers that are end-capped with esters (as opposed to the free carboxylic acid) have longer degradation half-lives. In this invention, the carboxylic group is activated to conjugate the stereoisomer peptide forming an amide bond; hence its degradation is not altered since there is no free carboxylic group available.

In one more embodiment, PLGA degrades in vivo by hydrolysis into alpha-hydroxy acids (i.e., the original monomers: lactic acid, and glycolic acid). Since the human body effectively degrades the monomers, there is minimal to none systemic toxicity associated with using PLGA polymers. Under normal physiological conditions, these two monomers are by-products of various metabolic pathways in the body (e.g., TCA cycle); hence PLGA was approved by the FDA in 1976, and has been used since then to deliver drugs, for example, against prostate cancer.

PLGA Nanoparticles Loaded with Stereoisomer Peptides in Free Form

In one embodiment, solvent evaporation and solvent extraction processes are carried out by a single emulsion process, or by double multiple emulsion process. The single emulsion process consists in a process where oil-in-water (o/w) is used for the emulsification. PLGA is dissolved in water immiscible and volatile dichloromethane (DCM) followed by addition of the drug to produce a solution or dispersion of the drug particles. This polymer-solvent-drug-solution-dispersion is emulsified by stirring at an appropriate temperature in a large volume of water containing poly vinyl alcohol (PVA) to yield the oil-water emulsion. This emulsion is then subjected to solvent removal to harden the oil droplets. Solvent removal is carried out by evaporation with reduced pressure or at atmospheric pressure with reduced stir rate and slowly to prevent the formation of porous particles, or by extraction by transferring the emulsion into a large volume of water with or w/o surfactant or a quenching medium, into which the solvent in the oil droplets is diffused out. The later is simpler and faster and do not form porous particles. The solid microspheres are then washed and collected by filtration, sieving, or centrifugation, and dried under appropriate conditions or lyophilized to obtain the final free microsphere product. Unfortunately this method yields poor encapsulation efficiencies since hydrophilic drugs (i.e., peptides) diffuses out or partitions from the dispersed oil phase into the aqueous phase and the drug gets dispersed in the surface of the polymer matrix causing a rapid release of the peptide (burst effect); hence this method is more appropriate to encapsulate steroids rather than hydrophilic drugs.

In another embodiment, the oil-in-oil emulsification method consists essentially in solubilizing PLGA and the drug in acetonitrile. This solution is then dispersed in light mineral oil in the presence of surfactant (e.g., Span) to obtain the oil-in-oil emulsion also known as water-in-oil. The microspheres are then obtained by evaporation or extraction of the organic solvent and the oil is washed off with n-hexane. This method is preferred for insoluble drugs.

In one more embodiment, the method of phase separation known also as coacervation is also used to encapsulate peptides. It consists of decreasing the solubility of the encapsulating polymer by addition of a third component to the polymer solution in an organic solution; the process yields two liquid phases: the polymer containing coacervate phase and the supernatant phase depleted in polymer. The peptide which is dispersed or dissolved in the polymer solution is coated by the coacervate, which essentially includes three defined steps which are the phase separation of the coating polymer solution; adsorption of the coacervate around the drug particles, and solidification of the microspheres. The polymer is dissolved in an organic solution and the stereoisomer peptide is dissolved in water and dispersed in the polymer solution (water-oil emulsion). An organic nonsolvent is then added to the polymer-stereoisomer peptide-solvent system with stifling which gradually extracts the polymer solvent. The polymer is subjected to phase separation and it forms very soft coacervate droplets which entrap the stereoisomer peptide. The particle size is controlled by stirring. This system is then transferred to a large quantity of a nonsolvent organic to harden the micro droplets and form the final microspheres which are collected by washing, sieving, filtration, or centrifugation, and dried.

In a preferred embodiment, the double emulsion process water-in-oil-in-water (w/o/w) is used. Briefly, the stereoisomer peptide and a solution of PLGA is mixed and stirred to form the microemulsion in which water containing PVP is added to obtain the emulsion (see Example 5).

In other preferred embodiment, the spray drying method is used given its speed, convenience, easiness to scale-up, under mild conditions, and does not depend on the solubility parameter of the drug and the polymer. This process requires a double-nozzle spray-drying technique in the presence of an anti-adherent. This method produces microspheres with high yield and encapsulation ratio compared to those prepared with the double-emulsion method (see Example 5).

In one more preferred embodiment, low-temperature spraying method for preparing PLGA is used to increase the efficiency of encapsulation and drug retention. This process increases the microspheres encapsulation efficiencies above 95% (see Example 5).

In other embodiment, the PLGA polymer particles loaded with a plurality of different stereoisomer peptides are prepared using a variation of the mulsion method. Briefly, the different stereoisomer peptides are dissolved in a 1% aqueous solution and added to a 2% solution of PLGA in DM ($Cl_2CH_2$) by fast vortexing to obtain an emulsion, which is then mixed with the aqueous phase of PF-68 at 1%; the emulsion is sonicated at 140 w and 20 kHz for 2 minutes to create the nanoparticles. The organic solvent is evaporated overnight with continuous stifling and the nanoparticles rinsed at least four times in DI water by ultracentifugation at 40,000 rpm for one hour at 4° C. followed by lyophilization in a solution of 5% sucrose using a condenser at low temperature (−55° C.) under low pressure (<1 millibar).

Alternatively, the emulsion can be prepared with peptides and PLGA 504H (1:2.3) mixed in DM at RT with a stirrer. The organic phase is injected with a syringe into 75 mL of an aqueous polyvinyl alcohol (PVA) but preferably PVP (reduce burst effect) solution and homogenized at 24K rpm for 5 minutes. The emulsion is sonicated (2 minutes at 30 W). The resulting nanoemulsion is maintained under gentle mixing for 4 hours to evaporate off the organic solvent. The nanoparticles are collected by centrifugation at 20K rpm/20 min, washed 3 times with DI water, and the nanoparticle dispersion is freeze-dried (−40° C.) for 48 hours to obtain a fine powder.

In one more embodiment, oil and water or oil/oil is used. In the oil/water emulsion 20 mg of phospholipid lecithin is added to the water phase followed by the nanoparticles preparation as described above; in the oil/oil emulsion the peptide and PLGA (1:5) are added to acetonitrile which is added into viscous liquid paraffin containing Span 80 under continuous stifling to obtain a finely dispersed drug suspension. The suspension is heated to 55° C. and stirred for 2 hours to ensure complete evaporation of acetonitrile. The collection, washing, and nanoparticle freeze-dried procedures are carried out as described above.

In a preferred embodiment, appropriate characterization of the encapsulated nanoparticles loaded with different stereoisomer peptides or the stereoisomer peptide-ligand includes (i) particle size determination using a particle size analyzer, (ii) encapsulation efficiency by centrifugation and UV readings; and (iii) drug release in vitro studies in PBS at 37° C. with continuous stirring followed by the analysis of aliquots taken at a predetermined interval to measure the amount of released peptide by UV spectrometry using standard control curves.

Preparation of Nanoparticles

In a preferred embodiment, the encapsulation of stereoisomer peptides entails the formation of nanoparticles, the preferred particle size of this invention. Since there is need to direct the drug to target tissues via systemic circulation or across the mucosa, it is necessary, therefore, to administer particles less than 500 nm to be able to cross the cell membrane. Nanoparticles (nanospheres and nanocapsules) can thus be prepared by the same methods but adjusting the manufacturing parameters to obtain nanometer-size droplets.

Preparation of PLGA-Stereoisomer Peptide Conjugates

Figure 3:
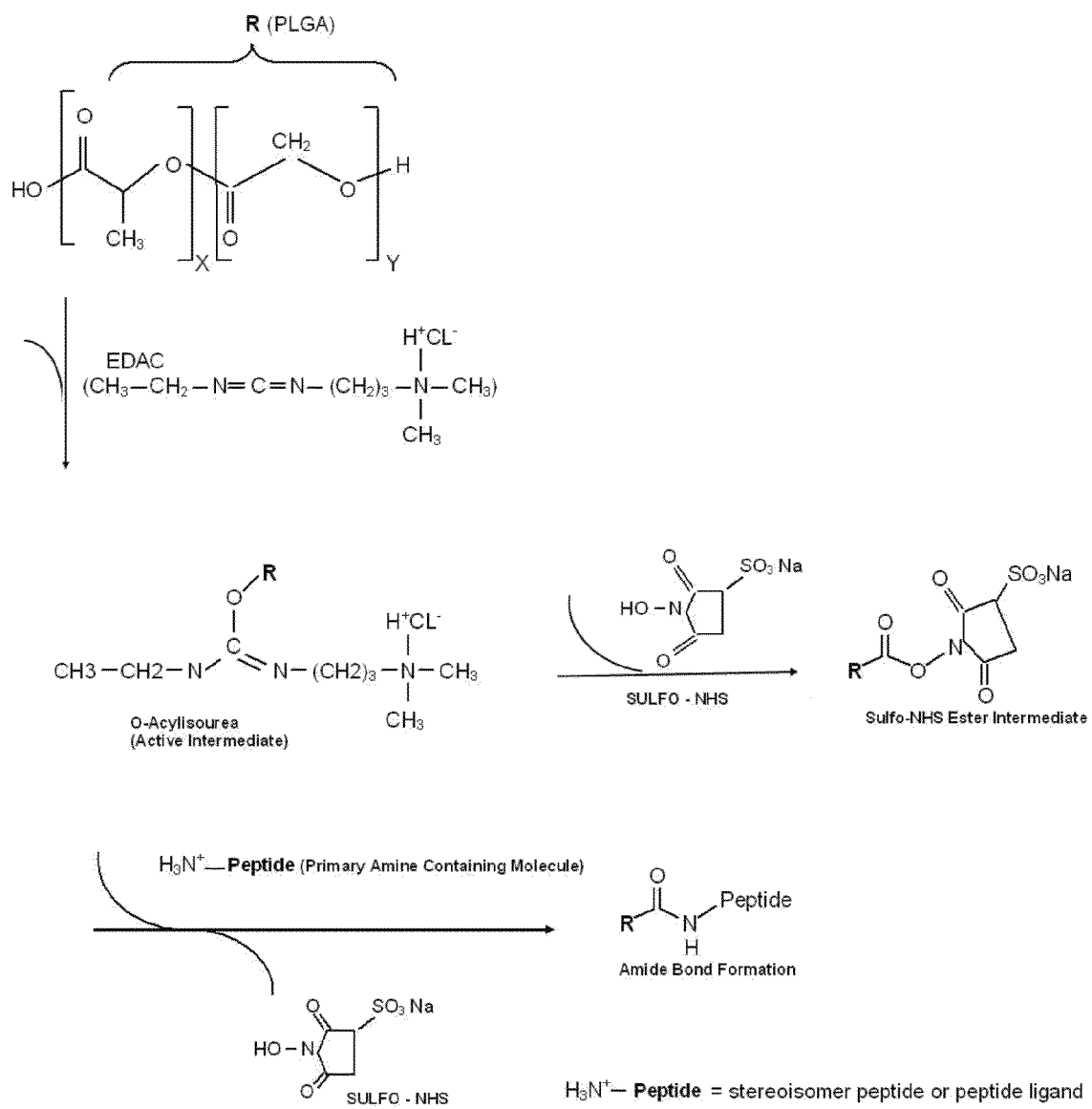
FIG. 3 illustrates the chemical activation and conjugation of PLGA with a stereoisomer-peptide. The primary amine containing molecule is a stereoisomer peptide or a stereoisomer peptide-ligand. The final product is PLGA conjugated with a specific stereoisomer peptide or PLGA conjugated with a stereoisomer peptide-ligand for targeted delivery. The later is conjugated on the surface of polymer nanoparticles loaded with a plurality of different PLGA conjugated with a stereoisomer peptide creating a novel ligand-targeted multi-stereoisomer peptide-polymer conjugate compound.
Figure 4:
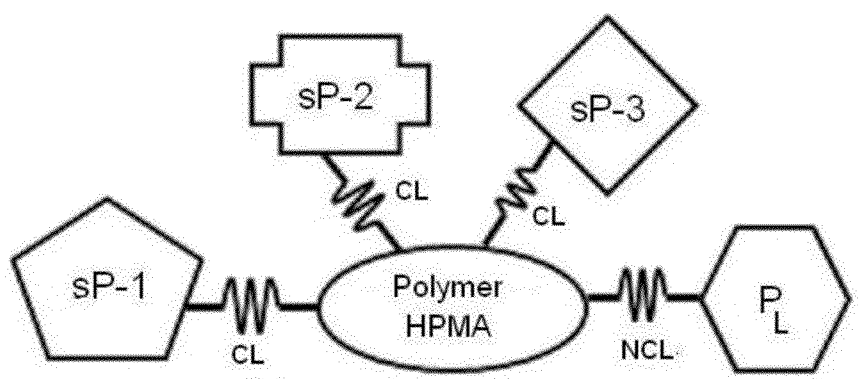
FIG. 4 is a diagram of a novel ligand-targeted multi-stereoisomer peptide-polymer conjugate compound, where sP-1, sP-2, and sP-3 represent three different stereoisomer peptides, CL represents a cleavable linker, NCL represents a non-cleavable linker, $P_L$ represents a stereoisomer peptide-ligand, and the polymer is represented by HPMA.

In other preferred embodiment, each different stereoisomer peptide (sP) and the peptide ligand ($P_L$), are directly conjugated to activated PLGA (co-monomer) in separate reactions. Activated PLGA is reacted with the free amino group present in the linear stereoisomer peptide or with the deprotected 8-amino group of the Lys residue for cyclic stereoisomer peptides. This reaction is shown in detail in FIG. 3 and Example 3. This procedure allows the conjugation of each different stereoisomer peptide and the peptide-ligand with PLGA allowing firm holding and extended release of the stereoisomer peptide rather than encapsulating a plurality of different stereoisomer peptides in free form.

In one more preferred embodiment, the resulting products are PLGA monomers conjugated with stereoisomer peptide, and PLGA monomers conjugated with stereoisomer peptide-ligand. The former creates a plurality of different PLGA-stereoisomer peptide conjugates; the latter creates a single specific PLGA-peptide-ligand conjugate. This specific PLGA-peptide-ligand conjugate is then used to encapsulate the plurality of PLGA-stereoisomer peptide conjugates with polymer nanoparticles (see below). Thus, the peptides are not in free from but conjugated with PLGA, and this plurality of conjugates are inside PLGA nanoparticles (see FIG. 2, 3 and Example 5). This allows longer retention times, elimination of the burst effect, and better encapsulation efficiency.

Preparation of PLGA Nanoparticles Loaded with PLGA-Stereoisomer Peptide Conjugates In other preferred embodiment, the encapsulation of stereoisomer peptides conjugated with PLGA is carried out with a plurality of different stereoisomer peptides that have been conjugated each separately with PLGA following the methods described in the preceding pages and Example 5. This approach has the purpose of creating PLGA nanoparticles loaded with PLGA conjugated with stereoisomer peptides with the purpose of increasing the stability and better retention of the peptide in the particles, allowing longer periods of time for the peptides to be released in the target site, and obtaining a higher efficiency of encapsulation. In this invention, the preferred method is the double emulsion process: water-in-oil-in-water (w/o/w) with the low-temperature spraying method to prepare the loaded PLGA nanoparticles since this method best fit the stereoisomer peptides of this invention. The final product is a novel multi-stereoisomer peptide-PLGA conjugate compound.

Preparation of PLGA Nanoparticles Carrying Stereoisomer Peptide-Ligand Conjugated on the Surface of the Polymer and Loaded with PLGA-Stereoisomer Peptide Conjugates In another preferred embodiment, the encapsulation of PLGA nanoparticles carrying on their surface a peptide-ligand and loaded with a plurality of different PLGA-stereoisomer peptide conjugates are also prepared following the preferred method of double emulsion process: water-in-oil-in-water (w/o/w) with the low-temperature spraying method. The final product is a novel specific ligand-targeted multi-stereoisomer peptide-PLGA conjugate compound, and this is the first time that PLGA is used to create the compounds of the invention.

HPMA Polymer and Stereoisomer-Peptide-HPMA Conjugates

In one embodiment, water soluble polymer HPMA is used as a carrier for the stereoisomer peptides to create stereoisomer peptide-polymer conjugate compounds. The polymer selectivity is due to the manner polymer-containing compositions enter cells, which is through receptor mediated endocytosis. The polymer body distribution delivers drugs passively due to the enhanced permeability and retention (EPR) effect.

In other embodiment, attachment of stereoisomer peptides to HPMA provides ideal pharmaceutical properties for the peptides since HPMA (N-(2-Hydroxypropyl) methacrylamide) is a hydrophilic and biocompatible polymer, and their copolymers are of great value as platform for delivery of such peptides. Conjugation of any of the stereoisomer peptides disclosed in this invention to HPMA, in their synthetically and chemically modified forms, will result in novel HPMA polymer conjugates carrying a specific stereoisomer peptides and a peptide-ligand for targeted delivery. Furthermore, conjugation of a plurality of stereoisomer peptides to the polymer allows the creation of novel ligand targeted multi-stereoisomer peptide-HPMA conjugate compounds. Since the peptides have sequences that target specific domains of disease proteins or anti-nagiogenic proteins, the novel compounds created here are also quite suitable for any of the anti-disease strategies disclosed in this invention.

In one more embodiment, poly HPMA (i.e., with multiple branches) with terminal $NH_2$ groups is synthesized by polymerization using 2,2'-azobisisobutyronitrile as the initiator in the presence of DMSO and gas argon. HPMA copolymer is purified to obtain a polymer of the desired molecular weight. This polymer with functional $NH_2$ groups is then used to conjugate the target molecules via a linker.

In one additional embodiment, the polymer N-(2-Hydroxypropyl) methacrylamide (HPMA), is a biocompatible linear scaffold polymer carrier with separate branches where individual molecules, e.g., stereoisomer peptides, can be conjugated to functional groups of a polymer branch. The function of the HPMA polymer is to deliver the stereoisomer peptides to targeted tissues, cells, and sub-cellular locations. The polymer conjugate compounds may contain two or more different synthetic linear or cyclic stereoisomer peptides that may be independently and in separate reactions attached to a functional group of a separate branch of a polymer scaffold via a linker to create novel linear and cyclic multi-targeted stereoisomer peptide polymer conjugate compounds.

In still another embodiment, HPMA property of being inert, safe, non-toxic, non-immunogenic, water soluble, and biocompatible, make it suitable for conjugation to a variety of macromolecules (e.g., immunoglobulin, antibodies, antibiotics, natural proteins, natural peptides), and for the first time to a plurality of different stereoisomer peptides in retroinverso configuration and cyclic structures. HPMA physicochemical properties allow the compounds of this invention to extend their half-life in vivo, and reduce significantly their immunogenicity, and antigenicity; and eliminating toxicity (if any). HPMA also enhances the stereoisomer peptides' biological activity, blood circulation time, aqueous solubility, and resistance to protease digestion. This is the first time that HPMA is used to conjugate a plurality of different specific stereoisomer peptides in retro-inverso configuration and cyclic structures, to create the compounds of this invention.

N-(2-Hydroxypropyl)methacrylamide

In one embodiment, the invention employs standard techniques for the synthesis and manipulation of polymer copolymers and monomers with appropriate modifications specific to the compounds of this invention. As used herein, the term HPMA refers to N-2-hydroxypropyl methacrylamide, a hydrophilic (water soluble) polymer represented in general as HPMA homopolymer (e.i., several monomers). Synthesis of HPMA, the basic unit of the polymer, is carried out in a solution of 1-amino-2-propanol (65.6 ml 0.84 mol) in 250 ml of acetonitrile, in which freshly distilled methacryloyl chloride (MACL) (41 ml, 0.42 mol) in 20 ml acetonitrile is added drop wise under vigorous stifling and cooling to −5° C. A small amount of inhibitor, tertiary octyl pyrocatechine is added to control polymerization. The reaction mixture is stirred for 30 min at room temperature. 1-amino-2-propanyl hydrochloride formed as a byproduct is precipitated and filtered off. The filtrate is cooled at −70° C. in a dry-ice acetone bath to precipitate HPMA. After equilibrating to room temperature the product is filtered off and washed with pre-cooled acetonitrile. The pure product is isolated by re-crystallization from acetone.

Co-Monomers Containing GFLG Spacer/Linker

In one embodiment, the synthesis of MA-GFLG-ONp is carried out in two steps. First MA-Gly-Phe-OH and Leu-Gly-OMe.HCl are synthesized separately. Subsequently the two dipeptides are coupled to yield MA-GFLG-OMe. The methyl group is removed with base (NAOH) yielding MA-GFLG-OH, and to this compound the reactive group p-nitrophenol is attached by esterification.

In another embodiment, MA-Gly-Phe-OH is synthesized by dissolving 5.0 g, 22.5 mmol Gly-Phe in 5.6 ml NaOH, 4N (22.5 mmol) and cooled to 0° C. Freshly distilled Methacryloyl Chloride (MACL) (3.5 g, 34 mmol) in 10 ml of dichloromethane is added drop wise. A small amount of inhibitor (1-octyl pyrocatechine) is added to prevent polymerization of the monomers into high molecular weight oligomers. After a slight delay 8.4 ml (34 mmol) of 4N NaOH is added drop wise to the mixture. After addition of MACl and NAOH, the reaction mixture is brought to room temperature and allowed to react for 1 hour at pH between 6 and 7. The dichloromethane layer is separated from the water layer, washed with 2 ml of water, and discarded. The aqueous layer together with the washings was mixed with 40 ml of EtOAc. HCl is then added slowly under vigorous stirring and cooling until pH 2-3 is reached. The organic layer is separated and the aqueous layer is extracted three times (3×20 ml), and then dried overnight over anhydrous sodium sulfate. The dried solution is filtered and washed with EtOAc. The EtOAc was, removed by rotary-evaporation to obtain a white powder product, which is then re-crystallized from EtOAc. Synthesis of MA-Gly-Gly-OH is carried out with the same method except that Gly is used instead of Phe residue.

In one more embodiment, Leu-Gly-OMe.HCl is synthesized by dissolving Leu-Gly (4 g. 21 mmol) in 35 ml of methanol and cooled at −5° C., followed by drop wise addition of 2 ml of SOCl2 (26 mmol) under stirring. After equilibration at RT the mixture is refluxed for three hours. The solvent is evaporated to dryness and the residue dissolved in methanol and evaporated to remove HCL and SOCl2. The residues is dissolved in benzene and evaporated to obtain a while amorphous solid and used in subsequent synthesis steps.

Monomer MA-GFLG-OMe

In one embodiment synthesis of MA-GFLG-OMe is carried out by coupling MA-Gly-Phe and Leu-Gly-OMe.HCl in 80 ml of Me-OH and cooled to 0° C.; excess of 1N NaOH is added (18 nmol) drop wise under stirring. After addition of small amount of inhibitor (1-octyl pyrocatechine) the reaction mixture is stirred for 1½ hr at 0° C., and then for 2 hours at room temperature. Methanol is removed by concentration under vacuum. 160 ml distilled water is added and the mixture is acidified to pH 2. The free acid is extracted in EtOAc (4×200 ml), washed with saturated brine, and dried over anhydrous sodium sulfate overnight. Solvent is evaporated under vacuum and the tetrapeptide product is re-crystallized from EtOAc. Synthesis of MA-GG-OMe is carried out with the same method except that GG oligopeptide is used instead of the GF and LG oligopeptides.

Monomer MA-GFLG-OH

In one embodiment, synthesis of MA-GFLG-OH is carried out by adding MA-GFLG-OMe (6.9 g, 14.5 mmol) to 80 ml methanol and cooled to 0° C.; excess 1N NAOH (18 ml, 18 mmol) is added drop wise under stirring. A small amount of inhibitor, tertiary-octyl pyrocatechine is added to prevent polymerization, and the reaction is stirred for 1½ hours and then two hours at RT. The reaction mixture is concentrated under vacuum to evaporate methanol; 160 ml water are added and the mixture is acidified with concentrated citric acid to pH 2.0. The free acid is extracted with EtOAc (4×200 ml), washed with a salt saturated solution, and dried over anhydrous sodium sulfate overnight. After evaporation of the solvent under vacuum the product is re-crystallized from EtOAc. Synthesis of MA-GG-OH is carried out with the same methods except that MA-GG-OMe is used.

Preactivated Monomer MA-GFLG-ONp

In one embodiment, synthesis of MA-GFLG-ONp is carried out by adding to a solution of MA-GFLG-OH (4.7 g, 10 mmol) in 80 ml of DMF, a solution of 1.67 g of p-nitrophenol (12 mmol) in 20 ml of DMF under stirring and cooling to −10° C., followed by a solution of 2.5 g of DCC (12 mmol) in 8 ml of DMF. The reaction mixture is stirred for six hours at −10° C., and then overnight at 4° C. The precipitated byproduct DCU is filtered off and the DMF removed by rotary evaporation. The residue is dissolved in EtOAc and the remaining byproduct is filtered off. EtOAc is evaporated to dryness. The final product is soaked in ether to remove excess p-nitrophenol. This procedure is repeated several times and the purity of MA-GFLG-ONp is checked by calculating the extinction coefficient in DMSO. MA-GFLG-ONp content is assessed by release of p-nitrophenol (ONp) from the polymer in 1.0 N NaOH by UV spectrophotometry (400 nm). Synthesis of MA-GG-ONp is carried out with the same method except that MA-GG-OH is used.

Polymer Precursors HPMA-MA-GFLG-ONp and HPMA-MA-GG-ONp

In one embodiment, synthesis of polymer precursor HPMA-MA-GFLG-ONp and HPMA-MA-GG-ONp is carried out separately by radical polymerization of the corresponding monomers HPMA and MA-GFLG-ONp, and HPMA and MA-GG-ONp, respectively. These copolymers are analyzed by size-exclusion chromatography. The content of ONp groups is determined by UV/vis spectrophotometry. Briefly, polymerization is carried out using a mixture of HPMA, MA-GFLG-ONp and MA-GG-ONp at various molar ratios using the initiator 2,2'-azobisisobutironitrile (AIBN). The solution containing the monomers in desired molar ratios dissolved in acetone and mixed with the initiator is transferred to an ampoule and bubbled with nitrogen for 5 min, sealed and placed in an oil bath at 50° C. for 24 hours under stirring. After 24 hours the copolymers would precipitate out of solution and the ampoules are cooled to room temperature and placed in the freezer for 20 minutes to increase the yield of the precipitated polymer further. The copolymers are filtered off, dissolved in methanol, and precipitated in ether. After filtration and washing with ether the copolymers are dried under vacuum. The copolymers are analyzed by size exclusion chromatography. These two polymer precursors can also be obtained as pre-activated para-nitrophenol ester directly from the supplier.

For detail of the synthesis of the stereoisomer peptides and stereoisomer peptide-ligand to HPMA monomer and co-monomers, and the creation of the final product, a ligand-targeted multi-stereoisomer peptide-HPMA conjugate compound see Examples 7, 8, 9 and 10.

In another embodiment, the pre-activated copolymer HPMA-GFLG-ONp is also commercially available, allowing the reduction of several synthesis steps. The direct coupling of the amine group of a stereoisomer peptide to the pre-activated copolymer HPMA-GFLG-ONp in separate reactions for each different stereoisomer peptide, followed by copolymerization (all together) with the monomer MA-GG-PL, the ligand-targeted multi-stereoisomer peptide-HPMA conjugate of the form HPMA-[GFLG-D-peptide]×3-GG-$P_L$ is created. Detail of this method is provided in Example 11 and FIG. 5.

In one additional embodiment, the molecular weight of the branched polymer precursor and the polymer conjugate is approximately 30 to 50 KDa with about 30 KDa for the precursor and about 45 KDa for the conjugate. The term "about" indicates that in preparations of hydrophilic HPMA, some molecules will weigh more, some less, than the stated molecular weight. The final molecular weight will depend on the polymerization reaction that determines the number of branches desired in the polymer, the size of the peptide-ligand, and the target specific stereoisomer peptides conjugated to HPMA copolymer pre-activated precursor, which can be determined by gel-filtration chromatography, and the peptide content in the conjugate can be determined by amino acid analysis.

In one more embodiment, the synthesis of ligand-targeted polymer conjugates carrying each a single stereoisomer peptide and the targeted stereoisomer peptide-ligand ($P_L$) (with or without a linker) are referred in this invention as stereoisomer peptide-HPMA conjugate compounds and constitute a subject matter of this invention. These conjugate compounds can be evaluated using in vitro and in vivo assays to determine the ability of each specific stereoisomer peptide to compete, bind, block, or inhibit a functional group of the corresponding target protein.

In still another embodiment, the synthesis of ligand-targeted polymer conjugates carrying each more than one different stereoisomer peptide and the targeted stereoisomer peptide-ligand ($P_L$) (with or without a linker) are referred in this invention as multi-stereoisomer peptide-HPMA conjugate compounds and constitute also the subject matter of this invention. These multi-peptide polymer conjugates can be synthesized by mixing more than one stereoisomer peptide and the stereoisomer peptide-ligand ($P_L$) in the reaction mixture to generate polymer conjugates containing randomly distributed stereoisomer peptides with different sequences and the stereoisomer peptide-ligand $P_L$. However, this approach may provide heterogeneous amounts of the different stereoisomer peptides; therefore to generate multi-stereoisomer peptide polymer conjugates with homogeneous amount of each peptide, the monomers carrying the stereoisomer peptides and the stereoisomer peptide-ligand are preferably synthesized separately, and then polymerized (radical polymerization) to create the final targeted polymer with different stereoisomer peptides and the peptide-ligand $P_L$.

In one additional embodiment, it is also desirable to synthesize separately, for example, three different polymer conjugates; two carrying each a different stereoisomer peptide and one carrying the stereoisomer peptide-ligand. These individual conjugates are purified and then mixed in equivalent molar ratios. These mixtures of polymer conjugates carrying different stereoisomer peptides and peptide ligand are also referred in this invention as multi-stereoisomer peptide- HPMA conjugate compounds since the mixture comprises different stereoisomer peptides.

Uses of Synthetic Stereoisomer Peptides of the Present Invention

In one embodiment, the peptides in the form of stereoisomer peptides in retroinverso and/or inverso and linear or cyclic configurations, but preferably with retroinverso and cyclic configurations, are useful in assays in vitro to determine their inhibitory activities ($IC_{50}$) in different human endothelial and cancer cell lines and other human cells and in strains of a desired target pathogen. In the preferred practice of the present invention, two or more different synthetic stereoisomer peptides are conjugated to a polymer system such as PLGA or HPMA. This stereoisomer peptide-polymer combination system creates novel synthetic ligand-targeted multi stereoisomer peptide-polymer conjugate compounds. These polymer conjugates are compounds that provide benefits over non-conjugated polymers, such as improved solubility and in vivo stability. These conjugates can be used to determine the polymer's transport properties, efficiency of internalization, permeability, and retention and biodistribution in vitro in certain human cells or in vivo in a particular disease animal model, or its binding or internalization in different viral, or bacterial cells. The stereoisomer peptides conjugated to the polymer have the potential to block or inhibit functional domains of corresponding target proteins. By labeling such compounds with $^{99m}Tc$ or $^{90}Y$ or by using fluorescent molecules such as Cy5 and Eu, one can identify cells having the compounds on their surfaces or in subcellular locations using fluorescent imaging. In addition, the stereoisomer peptides and the conjugates can be used in Western blotting, ELISA (enzyme-linked immunosorbent assay), FACS analysis based on their ability to bind specifically to the target proteins or cells; the stereoisomer peptides may also be used in purifying cells expressing a particular microorganism protein on the cell surface or inside the cells.

In other embodiment, the specific inhibitory activities of the stereoisomer peptides in free form or conjugated to a polymer as described in this specification can be further tested against the corresponding target proteins using appropriate in vitro assays and in vivo, animal models. A variety of commercially available disease models can also be used to experimentally studying the compounds against a particular target protein in vivo. For example, animal models include but are not limited to mouse models for macular degeneration, for breast, pancreatic, melanoma and a variety of other cancers, for multiple sclerosis, and neuropathies to name a few. Finally, the description provides a large group of peptides from which peptides of interest can be selected to synthesize the stereoisomr peptides, prepare the compounds of the invention and test them in vivo for their inhibitory activities against a specific target protein.

In another embodiment, the stereoisomer peptides in free from are useful as commercial reagents for various research and diagnostic applications including the preparation of antibodies, or antigen-antibody binding and complexes formation using commercially available pathogen or proteins antibodies. They could also be used as blocking reagents in random peptide screening aimed to find new antigens that target a specific causing disease protein or an uncommon microorganism strain, or to raise antibodies specific for a particular protein of human or microorganisms.

Pharmaceutical Compositions

In one embodiment, the invention further provides pharmaceutical compositions comprising formulated linear and cyclic stereoisomer peptide compounds and ligand-targeted multi-stereoisomer peptide-polymer conjugate compounds.

The compounds may be prepared for administration by oral, ocular, transmucosal (nasal, vaginal, rectal, or sublingual), parenteral [intramuscular (i.m), intraperitoneal (i.p.), intravenous (i.v.), intra cardiac (i.c.) and subcutaneous (s.c.)], topical, transdermal (passively) and pulmonary routes, and may be formulated in dosage configurations appropriate for each route of administration using pharmaceutically acceptable excipients. Procedures to prepare pharmaceutical compositions and their solid dosage configurations are well known in the art (see Martin E W, 1990, Remington's Pharmaceutical Sciences. 8th Ed. Mack Publishing Co., Easton, Pa. 18042; and Marshall K, 1979, In Modern Pharmaceutics, Edited by G. S. Banker and C. T. Rhodes Chapter 10, 197), herein incorporated by reference.

In other embodiment, the pharmaceutical compositions comprise effective amounts of a stereoisomer peptide, a mixture of stereoisomer peptides or stereoisomer peptide-polymer conjugates, together with pharmaceutically acceptable diluents, solubilizers, emulsifiers, preservatives, adjuvants and/or carriers. Such compositions may include diluents of various buffer content, pH, and ionic strength; additives such as detergents and solubilizing agents, anti-oxidants, preservatives and bulking substances, and the compositions may be prepared in liquid configuration or in dried powder configuration.

Oral Delivery

In preferred embodiments, the compounds of this invention are synthetic stereoisomer peptides, which unlike typical peptide formulations with L-peptides, have the advantage of being stable and not being degraded by proteases, which are pharmaceutical properties for oral bioavailability or for administration in harsh environments via the mucosa. Natural peptides with L do not allow such routes of administration due to fast degradation. In particular, cyclic stereoisomer peptides containing only D-amino acids are effective therapeutics due to enhanced stability. Thus, they can be orally administered to a mammal, and be readily taken up and delivered to the serum. These modifications facilitate their uptake in the blood stream from the digestive/intestine system. In preferred embodiments, linear and cyclic stereoisomer peptides are conjugated to a biocompatible polymer further enhancing their bioavailability and therefore can be administered orally, without protection against proteolysis by stomach acid. The peptides, comprising the active material, are stable at low pH and resistant to degradation by enzymes. Generally, the chemical modification contemplated here permits stability of the components and inhibition of proteolysis by enzymes of the digestive tract, and increased overall circulation time in the body.

In other embodiment, the formulation will include inert ingredients, which allow for further protection against the digestive system environment, and release of the biologically active material in the intestine, and blood stream. Also contemplated for use herein are liquid dosage forms for oral administration, including emulsions, solutions, suspensions, and syrups, which may contain other components. A coating impermeable to acid pH may be considered to ensure full gastric resistance. Examples of inert ingredients used as enteric coatings are polyvinyl acetate phthalate, and their derivatives. Capsules may consist of a hard shell for delivery of dry therapeutic (i.e. powder), for liquid forms, a soft gelatin shell may be used. Colorants and/or flavoring agents, and diluents may also be included. Certain inorganic salts may be used as fillers. Disintegrants may be included in the formulation as well as binders to hold the compounds together to form a tablet and may include starch and gelatin. The unique properties of the compounds of this invention, allows flexibility in the mode of administration in addition to their potential for oral bioavailability.

Mucosal Delivery: Nasal, Vaginal, and Rectal Administration

In one embodiment, compositions for nasal, rectal, and vaginal delivery of the compounds of this invention are also contemplated. A therapeutic drug must be formulated to effectively penetrate the mucosa via these routes and target the earliest events of a disease or a pathogenic infection. Nasal delivery, for example, allows the passage of compounds to the blood stream directly after administering the therapeutic product to the nose, without the necessity for deposition of the product in the lung. Formulations for nasal delivery include those with dextran or cyclodextran and excipients well known in the art. Compositions for rectal or vaginal administration are preferably suppositories, which may contain, in addition to the active substance, excipients such as cocoa butter or wax, and may include lubricants made of wax or oil. Since the compounds of this invention resist degradation by enzymes found in human blood, serum, and body secretions, flexibility in the mode of administration as a topical for harsh mucosal environments is possible.

Topical Drug Delivery

In one embodiment, formulations for topical drug delivery include ointments and creams. Ointments are semisolid preparations, based on petrolatum or other petroleum derivatives. Creams containing the active ingredient include viscous liquid or semisolid emulsions. Cream bases are typically water-washable, and contain an oil phase, an emulsifier, and an aqueous phase. The oil phase is generally comprised of petrolatum and a fatty alcohol such; the aqueous phase generally contains a humectant. The emulsifier in a cream formulation is generally a nonionic, anionic, cationic, or amphoteric surfactant. The specific ointment or cream base to be used as will be appreciated by those skilled in the art is one that will provide for optimum drug delivery. As with other carriers or vehicles, an ointment base should be inert, stable, nonirritating and nonsensitizing.

Parenteral Delivery

In one embodiment, preparations for parenteral administration are also contemplated here and are well known in the art. They include standard sterile aqueous or non-aqueous solutions, suspensions, or emulsions. Examples of non-aqueous solvents or vehicles are polyethylene glycol, propylene glycol, vegetable oils, such as olive oil and corn oil, gelatin, and injectable organic esters such as ethyl oleate. Such dosage forms may also contain preserving, wetting, emulsifying, and dispersing agents. These formulations are sterilized by filtration by incorporating sterilizing agents into the compositions, by irradiating the compositions, or by heating the compositions. They can also be manufactured using injectable sterile water, or sterile medium, immediately before use.

Pulmonary Delivery

In one embodiment, compounds of this invention, can also be delivered to the lungs by inhaling and traverse across the lung epithelial lining to the blood stream. A wide range of mechanical devices designed for pulmonary delivery of therapeutic products are commercially available including but not limited to nebulizers, metered dose inhalers, and powder inhalers, all of which are familiar to those skilled in the art. Such devices require appropriate formulations suitable for the dispensing of compounds.

The foregoing formulations and administration methods are intended to be illustrative and not limiting. It will be appreciated that using the teaching provided herein, other suitable formulations and modes of administration could be readily devised and applied to the stereoisomer peptides and the therapeutic compounds of this invention.

Dosages

In one embodiment, for all of the stereoisomer peptide compounds and stereoisomer peptide-polymer conjugate compounds, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends on the desired therapeutic effect, on the route of administration, and on the duration of the treatment desired. Generally, dosage levels of 0.001 to 10 mg/kg of body weight daily are administered to mammals. Physicians may initially use escalating dosages starting at a concentration that meet the requirements for each individual being treated.

In other embodiment, modifications and variations of the compositions of the present invention, and methods for use, will be obvious to those of skill in the art from the foregoing detailed descriptions, and which are intended to fall within the scope of the appended claims.

Treatment of Mammalian Diseases

In a preferred embodiment, the compounds of the invention are useful in the treatment of a variety of mammalian disease conditions and disorders. Examples of such diseases in humans are abnormal angiogenesis, pathological conditions of the eye including age-related macular degeneration, choroidal neovascularization and diabetic retinopathy, cancer, solid tumors, tumor metastasis, inflammatory diseases, Alzheimer's and Parkinson's diseases, atherosclerosis, cardiovascular diseases, multiple sclerosis, autoimmune diseases, diabetes, rheumatoid arthritis, stroke, neurological disorders, dementia, brain disorders, neurodegenerative disorders, neuropsychiatric illnesses, bipolar disorder, diseases caused by aging, and HIV/AIDS, and other pathogens including but not limited to prions, viruses, bacteria, fungi, and parasites.

The references cited here and throughout the entire specification are provided merely to clarify and illustrate the description of the present invention and is not an admission that any such reference is "prior art" to the present invention.

The following examples are meant to illustrate the invention. They are not meant to limit the invention in any way since many alternative methods, techniques, procedures, and approaches can be readily applied.

Example 1

Preparation of Retroinverso Cyclo D-Peptides

The peptides corresponding to the inverse ("inverso") of the naturally occurring sequence are prepared with D-isomers ("retro") using standard solid-phase peptide synthesis methods. At the N-terminus, a lysine may be added for later use (i.e., conjugation to a polymer) and the epsilon amine group is protected by acetylation. The epsilon group is deprotected after synthesis to mimic the attachment point that is used to conjugate directly, for example, to an activated carboxyl group of a polymer or to the free carboxyl group of the end terminal residue of a linker attached to the polymer. An acid sensitive resin (Cl-Trt), preloaded with the C-terminal amino acid is used for peptide synthesis to allow for the isolation of side-chain protected peptides. N-alpha-Fmoc and side-chain protected D-amino acids are activated using HCTU [O-(1H-6-Chloro-benzotriazole-1-yl)-1,1,3,3-tetramethyl-uronium hexa-fluoro-phosphate] and added at a 4-fold excess to peptide resin. An 8-fold excess of DIPEA (N,N-diisopropylethylamine) is added and the reaction proceeds for 40-80 minutes at room temperature. A ninhydrin test is performed to insure completion of the coupling cycle. Once peptide synthesis is complete, the N-terminal Fmoc group is removed to uncover the N-terminal amine and the protected peptide containing a C-terminal carboxyl is cleaved from the Cl-trt resin using 30% HFIP (Hexafluoroisopropanol) in DCM ($CH_2Cl_2$).

The peptide fragments containing the free N-terminal amine and C-terminal carboxyl are then cyclized (e.g., head-to-tail) to obtain the constrained cyclic structure of the peptide using PyBOP (benzotriazol-1-yl-oxytri-pyrrolidino-phosphonium hexa-fluoro-phosphate) and DIPEA at a ratio of 1:2:2 in DCM, overnight at room temperature. The cyclized peptides are then cleaved in 95% TFA, 2.5% water, 2.5% triisopropylsilane, QC'd by HPLC and MS, and purified using preparative HPLC columns with gradients of water: 0.1% TFA versus acetonitrile: 0.1% TFA. Fractions that meet purity requirements and are shown to contain the correct mass by nanospray mass spectrometry (MS) and tandem MS are then lyophilized for storage at −80° C. Amino acid analysis is utilized to determine the net amount of the peptide with the rest being counter-ions (acetate salt, sodium, potassium and other ions) as well as water of hydration. The peptide purity is evaluated by analytical HPLC, using a C-18 column (4.6×250 mm). The purified peptide originally produced as the TFA salt is then converted to the acetate salt using a Dowex resin that had been converted to the acetate salt form. Incubation of the peptide with the acetate resin affects the exchange of the TFA for acetate, resulting in a peptide in its acetate form. The peptide is subjected to concentration determination, and lyophilization. The final peptide is dispensed in small aliquots of 1 mg each and stored at low temperature until used.

Example 2

Cyclization of Peptides by Disulfide Bond

Oxidation of the Cys residues of a stereoisomer peptide to form one, two, or three intramolecular disulfide bonds is achieved using the oxidizing agent DMSO or iodine ($I_2$). Cyclization is achieved by dissolving the SH-group containing stereoisomer peptide in a phosphate or bicarbonate aqueous buffer at pH 7-9. The concentration of the stereoisomer peptide is approximately 1 mg/ml or less. Nonaqueous solvent such as DMF, DMSO or methanol could be used alone or with water along with an appropriate proton scavenger such as triethylamine or diisopropylethylamine. The cyclized stereoisomer peptide is purified using high performance liquid chromatography (HPLC) and often times the cyclo peptide will elute earlier than the uncyclized precursor. This is due to the diminished available hydrophobic surface area in the cyclized peptide, which minimizes its interaction with the reversed phase matrix. The cyclization can take from 15 minutes to 24 hours depending on the specific conditions used; typically room temperature, solvent, stereoisomer peptide composition, and solubility. The reaction can be monitored by HPLC or with Ellman's reagent, which allows monitoring the amount of free SH— group being consumed. In other embodiments, and preferably, the formation of Cys bonds is controlled by the selective use of thiol-protecting groups during peptide synthesis. For example, where two intramolecular disulfide bonds is desired, the peptide chain is synthesized with the four Cys residues of the core sequence protected with a thiol protecting group. Thereafter, the thiol protecting groups are removed from the Cys residues where the disulfide bond is desired effecting bisulfide cyclization of the monomer chain.

Example 3

Synthesis of Poly(Lactic-Co-Glycolic Acid)

PLGA is synthesized by random ring-opening co-polymerization of two different monomers, the cyclic dimers (1,4-dioxane-2,5-diones) of glycolic acid and lactic acid. The reaction is catalyzed by tin(II) 2-ethylhexanoate, tin(II) alkoxides, or aluminum isopropoxide. During polymerization, glycolic and lactic acid monomeric units are bound together by ester linkages, creating the polymer PLGA, which is the linear aliphatic polyester, the final product. Depending on the ratio of lactide to glycolide used for the polymerization, different forms of PLGA are obtained, and identified based on the monomers' ratio used. PLGA 75:25 has a copolymer composition of 75% lactic acid and 25% glycolic acid. PLGA is amorphous and has a glass transition temperature in the range of 40-60° C. Unlike the precursor, homopolymers of lactic acid (polylactide) and glycolic acid (polyglycolide) which show poor solubilities, PLGA is readily dissolved by a wide range of common solvents, including acetone, ethyl acetate, chlorinated solvents and tetrahydrofuran.

Example 4

Activation of PLGA and Preparation of PLGA-Stereoisomer Peptide Conjugates

PLGA is activated with EDAC (1-ethyl-3-(3-dimethyl amino propel) carbodiimide hydrochloride) to form the active intermediate o-Acylisourea, which is subsequently reacted with sulfo-NHS to form the second intermediate sulfoNHS-ester; after addition of the primary amine containing molecule (e.i. stereoisomer peptide), sulfo-NHS is released and an amide bond is created between the polymer PLGA and the stereoisomer peptide creating a PLA-stereoisomer peptide conjugate. In this invention, the stereoisomer peptide conjugates includes the peptide ligand.

Example 5

Preparation of PLGA-Stereoisomer Peptide Conjugates Nanoparticles

The double emulsion process water-in-oil-in-water (w/o/w) method is the method best suited for peptides. An aqueous or buffered solution of the stereoisomer peptide with a stabilizer (e.g., pluronic F68, PEG 4600) or sodium glutamate, is added to a solution of PLGA-stereoisomer peptide-PLGA conjugate in DCM (or ethyl acetate) with vigorous stifling to form the microemulsion which is then added with stifling into a large volume of water containing PVP (which minimizes burst effect) to obtain the w/o/w emulsion, followed by solvent removal by evaporation at reduced pressure or at atmospheric pressure to evaporate DCM, or by extraction to diffuse out DCM by adding a large amount of water and stifling. The solid microspheres are washed and collected by filtration, centrifugation, or sieving, and then dried or lyophilized to obtain the final PLGA-stereoisomer peptide conjugate.

The spray drying method is very rapid, convenient, easy to scale-up, involves mild conditions, and is less dependent on the solubility parameter of the drug and the polymer. This process requires a double-nozzle spray-drying technique that uses mannitol as an anti-adherent. A solution or dispersion of the stereoisomer peptide in a PLGA solution is sprayed from one nozzle and from another nozzle an aqueous mannitol solution is sprayed simultaneously producing the final microspheres. The surface of the spray-dried microspheres is coated with mannitol which allows decreased agglomeration. This method produces microspheres with higher yield and encapsulation ratio as compared to other procedures.

The low-temperature spraying method for preparing the nanoparticles is used to increase the efficiency of encapsulation and drug retention. The stereoisomer peptide-PLGA conjugate with excipients is suspended in a PLGA solution in acetone, ethyl acetate, or DCM. This suspension is then sprayed into a vessel containing liquid nitrogen overlaying a frozen extraction solvent like ethanol. The liquid nitrogen is subjected to evaporation causing the polymer solvent from the frozen droplets to be extracted then by liquid ethanol. This process increases the nanospheres encapsulation efficiencies above 95%.

Example 6

Preparation of PLGA Nanoparticles Carrying Stereoisomer Peptide-Ligand Conjugated on the Surface of the Polymer and Loaded with PLGA-Stereoisomer Peptide Conjugates The encapsulation of PLGA nanoparticles carrying on their surface a peptide ligand and loaded with a plurality of different PLGA-stereoisomer peptide comjugates are also prepared following the method of simple emulsion process: water-in-oil—(w/o/) with the low-temperature spraying method.

Example 7

Synthesis of Polymer Conjugates Containing Ligand-Targeted HPMA-GG-PL, and Conjugates Containing Stereoisomer-Peptides: HPMA-GFLG-D-Peptide Synthesis of polymer conjugates is carried out using the precursor HPMA-MA-GFLG-ONp to couple a target specific stereoisomer peptide in linear or cyclic form and in retro-inverso or inverso configuration to the polymer backbone via degradable GFKG linkers to generate a HPMA-GFLG-stereoisomer Peptide polymer conjugate, or using the precursor HPMA-MA-GG-ONp to couple a peptide-ligand (PL) (transduction domain or cell penetrating peptides), which is also a stereoisomer peptide, to the polymer backbone via non-degradable GG linkers to generate a HPMA-GG-$P_L$ polymer conjugate. Briefly, the precursor HPMA-MA-GFLG-ONp (20 mmol ONp) and stereoisomer-peptide (26 mmol) are dissolved in 400 μl DMF. 30 ml of N,N-diisopropylethylamine (DIPEA) (177 mmol) diluted in DMF (1:1, v:v) is added slowly drop wise with a Hamilton micro-syringe while stifling the mixture at room temperature in the dark overnight. Unreacted ONp groups are deactivated (hydrolyzed) with 1-amino-2-propanol (2 ml), the mixture containing HPMA-GFLG-stereoisomer-peptide is diluted in deionized water. The solution is dialyzed intensively and then lyophilized. A conjugate with high PL content is synthesized similarly using polymer precursor HPMA-MA-GG-ONp. The exact amount of stereoisomer peptide and stereoisomer peptide-ligand content of each separate conjugate is determined by amino acid analysis.

Example 8

Synthesis of Monomers MA-GFLG-D-Peptide and MA-GG-PL with Conjugated Stereoisomer Peptides MA-GFLG-D-peptide and MA-GG-$P_L$ monomers can be synthesized each separately following the procedure described above except that the monomer precursor MA-GFLG-ONp is used to attach a stereoisomer peptide and MA-GG-ONp is used to attach the peptide ligand, $P_L$. Briefly, the monomers MA-GFLG-ONp (20 mmol ONp) and stereoisomer peptide (26 mmol), and MA-GG-ONp (20 mmol ONp) and peptide-ligand $P_L$ (26 mmol), are dissolved in 400 μl DMF is separate reactions; 30 ml of N,N-diisopropylethylamine (DIPEA) (177 mmol) diluted in DMF (1:1, v:v) is added to each mixture slowly drop wise with a Hamilton micro-syringe while stifling the mixture at room temperature in the dark overnight. Unreacted ONp groups are deactivated (hydrolyzed) with 1-amino-2-propanol (2 ml), the mixture containing MA-GFLG-D-peptide or MA-GG-$P_L$ is diluted with deionized water. The solution is dialyzed intensively and then lyophilized. The exact amounts of peptide-ligand or stereoisomer peptide content of each separate monomer is determined by amino acid analysis.

The monomers MA-GFLG-D-peptide and MA-GG-$P_L$ are then polymerized with HPMA via radical polymerization of the monomers using AIBN (2,2'-azobisisobutyronitrile) as the initiator in the presence of DMSO and the inert gas argon to obtain the polymer conjugate HPMA-GFLG-D-peptide-GG-LP which contains one stereoisomer peptide coupled via a degradable GFLG linker and a peptide-ligand conjugated via a non-degradable GG linker. The peptide-ligand can be a transduction peptide, or a receptor binding peptide, or a cell penetrating peptide to guide the polymer to tissue, cells, or sub-cellular locations and deliver the stereoisomer peptide to the target protein to compete, bind, or block a functional site of the target disease protein.

Example 9

Copolymerization of Monomers HPMA, MA-$P_L$ and Preactivated Monomer MA-GFLG-ONp The polymerization is carried out using mixtures of HPMA, MA-$P_L$ and MA-GFLG-ONp at various molar ratios using the initiator 2,2'-azobisisobutironitrile (AIBN). The solution containing the monomers in desired molar ratios dissolved in acetone and mixed with the initiator is transferred to an ampoule and bubbled with nitrogen for 5 min, sealed and placed in an oil bath at 50° C. for 24 hours under stirring. After 24 hours the copolymers precipitate out of solution and the ampoules are cooled to room temperature and placed in the freezer for 20 minutes to increase the yield of the precipitated polymer further. The copolymer is filtered off, dissolved in methanol, and precipitated in ether. After filtration and washing with ether the copolymer is dried under vacuum. The molecular weight of the ligand-targeted copolymer HPMA-GFLG-ONp-$P_L$ is analyzed by HPLC.

Example 10

Synthesis of Monomer MA-$P_L$ without Linker

MA-$P_L$ (stereoisomer peptide-ligand) can be synthesized directly without a GG linker by mixing 0.1 mmol of the peptide-ligand in 1 ml of 0.1N NaOH (0.1 mmol) and cooled at 0° C. Freshly distilled MACL (15.6 mg, 0.15 mM) in 1 ml of dichloromethane is added drop wise a room temperature and allowed to react for one hour while maintaining the pH around 6-7. The organic layer is separated from the water layer, washed with 2 ml of water, and discarded. The aqueous layer together with the washings is mixed with 40 ml of EtOAc. Under vigorous stirring and cooling, HCL is added slowly until pH reaches 2-3. The organic layer is separated and the aqueous layer is extracted 3× with EtOAc (3×20 ml). The extracted layers are dried over anhydrous sodium sulfate overnight. The dried solution is filtered and washed with EtOAc, which is later removed with a rotary-evaporator to obtain the final product as a white powder, which is re-crystallized from EtOAc.

The copolymer precursor HPMA-MA-$P_L$-MA-GFLG-ONp and stereoisomer peptide are conjugated in the presence of DMF and DIPEA. The reactive ester groups of the pre-activated copolymer HPMA-$P_L$-GFLG-ONp are reacted with the stereoisomer peptide via nucleophilic attack of the amino groups (alpha-amino) forming amide linkages with the linker.

Example 11

Coupling Stereoisomer Peptides to Ligand-Targeted Pre-Activated Copolymer HPMA-GFLG-ONp-PL The copolymer precursor HPMA-MA-PL-MA-GFLG-ONp (20 mmol ONp) and stereoisomer peptide (26 mmol) are dissolved in 400 µl DMF. 30 ml of N,N-diisopropylethylamine (DIPEA) (177 mmol) diluted in DMF (1:1, v:v) is added slowly drop wise with a Hamilton micro-syringe while stirring the mixture at room temperature in the dark overnight. The reactive ester groups (i.e., carboxyl groups of residues converted to p-nitrophenyl ester) of the pre-activated copolymer HPMA-PL-GFLG-ONp are reacted with the stereoisomer peptide via nucleophilic attack of the amino groups (alpha-amino) forming amide linkages with the linker. Stereoisomer peptides can also be bound to the linker by the ε-amino group of a Lys residue attached to the linker or to the ε-amino group of a D-Lys residue in the stereoisomer peptide. Unreacted ONp groups are deactivated (hydrolyzed) with 1-amino-2-propanol (2 ml), the mixture containing the final product HPMA-PL-GFLG-D-peptide is diluted in deionized water. The solution is dialyzed intensively and then lyophilized. The exact content of stereoisomer peptide-ligand and stereoisomer peptide is determined by amino acid analysis.

Pre-activated copolymer HPMA-GFLG-ONp is also commercially available, allowing the reduction of several synthesis steps facilitating the rapid preparation of novel compounds. Briefly, coupling the amine group of different stereoisomer peptides directly to HPMA-GFLG-ONp in separate reactions, and then copolymerizing them all together with the monomer MA-GG-$P_L$, a ligand-targeted multi-stereoisomer peptide-polymer conjugate of the form HPMA-[GFLG-D-peptide]×3-GG-PL is created. The copolymer conjugates are synthesized via p-nitrophenyl ester aminolysis of the pre-activated copolymer precursor forming amide linkages between the reactive p-nitrophenyl ester groups of the linker and the amino groups, preferably ε-amino groups, in the stereoisomer D-peptide. This reaction is carried out by adding a solution of the D-peptide in DMF (dimethyl-formamide) and triethylamine (5:1), and the mixture is stirred overnight, at room temperature while protected from direct light, after which it is diluted with water (3 ml), dialyzed extensively against distilled deionized water and then lyophilized and stored at −20° C.

The skilled artisan will recognize that variations of the synthesis described in this specification may be used without departing from the spirit and scope of the invention. For example the stereoisomer peptide (1.3 times excess molar equivalents) may be dissolved in dry N,N-DMF under constant stirring followed by addition of dry pyridine (1:1 molar equivalents relative to the polymeric ONp content) and polymeric precursor in dry DMF. The reaction mixture is bubbled with nitrogen and continuously stirred at room temperature for 22 hours at 50° C. The reaction is terminated with 1-amino-2-propanol. The crude conjugate is dialyzed against deionized water, lyophilized, and stored at −20° C. The peptide content in the conjugate is determined by amino acid analysis. The conjugate molecular weight is estimated by size exclusion chromatography.

What is claimed is:

1. A ligand-targeted multi-stereoisomer peptide-polymer conjugate compound represented by the formula: [sP]n-(L)-Pol-sPL wherein:
   sP is a stereoisomer peptide,
   n is an integer from 2-4 representing a plurality of different stereoisomer peptides,
   said plurality of different stereoisomer peptides comprise the sequences
   SEQ ID NOs: 7, 11, 12 and 17;
   SEQ ID NOs: 7, 11, 12 and 27;
   SEQ ID NOs: 43, 48, 72 and 83; or
   SEQ ID NOs: 47, 48, 72, and 75,
   said peptides target each the functional domain of a specific protein involved in abnormal angiogenesis to inhibit, antagonize, bind, block, disrupt, interact and suppress, each simultaneously and independently, and positively, or negatively the target protein,
   said target protein is VEGF-165, tumstatin, neurophilin, VEGF Receptor, and somatostatin, or a-synuclein, amyloid, GSK-3, myelin, and tau,
   L is a linker,
   Pol is poly lactic-co-glycolic acid (PLGA); and
   sPL is a stereoisomer peptide ligand selected from the amino acid sequences consisting of SEQ ID NO:8, 10, 43, or 85.

2. The ligand-targeted multi-stereoisomer peptide-polymer conjugate compound of claim 1, wherein said stereoisomer peptide is made of D-amino acids.

3. The ligand-targeted multi-stereoisomer peptide-polymer conjugate compound of claim 2, wherein the stereoisomer peptide made of D-amino acids has inverso or retro-inverso configuration, and cyclic or linear structure.

4. The ligand-targeted multi-stereoisomer peptide polymer conjugate compound of claim 3, wherein cyclic stereoisomer peptide is cyclized via disulfide bond, amide bond, lactam bond, or thio-ether bond.

5. The ligand-targeted multi-stereoisomer peptide polymer conjugate compound of claim 3, wherein the linear structure is beta sheet or alpha-helix, and wherein the alpha-helix is stabilized by linking the terminal amino acid residues.

6. The ligand-targeted multi-stereoisomer peptide polymer conjugate compound of claim 1, wherein said poly lactic-co-glycolic acid (PLGA) is a polymer chain, a branched polymer, or polymer nanoparticles.

7. The ligand-targeted multi-stereoisomer peptide polymer conjugate compound of claim 6, wherein said polymer nanoparticles are loaded by encapsulation with a plurality of different stereoisomer peptides conjugated each separately to a poly lactic-co-glycolic acid (PLGA) polymer chain.

8. The ligand-targeted multi-stereoisomer peptide polymer conjugate compound of claim 7, wherein said polymer nanoparticles have a conjugated stereoisomer peptide ligand.

9. A composition comprising the compound of claim 1, wherein said composition contains an acceptable carrier, excipient, solubilizer, diluents, preservative, emulsifier and/or adjuvant.

* * * * *

SEQUENCE LISTING

<160> NUMBER OF SEQ ID NOS: 257

<210> SEQ ID NO 1
<211> LENGTH: 10
<212> TYPE: PRT
<213> ORGANISM: Artificial Sequence
<220> FEATURE:
<223> OTHER INFORMATION: Synthetic

<400> SEQUENCE: 1

Cys Arg Phe Tyr Val Val Met Trp Lys Cys
1               5                   10

<210> SEQ ID NO 2
<211> LENGTH: 10
<212> TYPE: PRT
<213> ORGANISM: Artificial sequence
<220> FEATURE:
<223> OTHER INFORMATION: Synthetic

<400> SEQUENCE: 2

Cys Gly Val Gln Thr Arg Ser Arg Arg Cys
1               5                   10

```
<210> SEQ ID NO 3
<211> LENGTH: 9
<212> TYPE: PRT
<213> ORGANISM: Artificial sequence
<220> FEATURE:
<223> OTHER INFORMATION: Synthetic

<400> SEQUENCE: 3

Cys Asn Gly Val Gln Tyr Arg Asn Cys
1               5

<210> SEQ ID NO 4
<211> LENGTH: 10
<212> TYPE: PRT
<213> ORGANISM: Artificial sequence
<220> FEATURE:
<223> OTHER INFORMATION: Synthetic

<400> SEQUENCE: 4

Cys Leu Leu Gly Gly Arg Leu Leu Gly Cys
1               5                   10

<210> SEQ ID NO 5
<211> LENGTH: 12
<212> TYPE: PRT
<213> ORGANISM: Artificial sequence
<220> FEATURE:
<223> OTHER INFORMATION: Synthetic

<400> SEQUENCE: 5

Cys Gly Ser Asp Pro Asn Gly Arg Arg Leu Thr Cys
1               5                   10

<210> SEQ ID NO 6
<211> LENGTH: 13
<212> TYPE: PRT
<213> ORGANISM: Artificial sequence
<220> FEATURE:
<223> OTHER INFORMATION: Synthetic

<400> SEQUENCE: 6

Cys Ile Val Arg Arg Ala Asp Arg Ala Ala Val Pro Cys
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Synthetic

<400> SEQUENCE: 7

Cys Gln Glu Tyr Pro Asp Cys
1               5

<210> SEQ ID NO 8
<211> LENGTH: 7
<212> TYPE: PRT
<213> ORGANISM: Artificial sequence
<220> FEATURE:
<223> OTHER INFORMATION: Synthetic

<400> SEQUENCE: 8

Cys Gly Asn Gly Arg Gly Cys
1               5
```

```
<210> SEQ ID NO 9
<211> LENGTH: 7
<212> TYPE: PRT
<213> ORGANISM: Artificial sequence
<220> FEATURE:
<223> OTHER INFORMATION: Synthetic

<400> SEQUENCE: 9

Cys Arg Gly Asp Phe Val Cys
1               5

<210> SEQ ID NO 10
<211> LENGTH: 10
<212> TYPE: PRT
<213> ORGANISM: Artificial sequence
<220> FEATURE:
<223> OTHER INFORMATION: Synthetic

<400> SEQUENCE: 10

Cys Arg Arg Arg Arg Arg Arg Arg Arg Cys
1               5                   10

<210> SEQ ID NO 11
<211> LENGTH: 7
<212> TYPE: PRT
<213> ORGANISM: Artificial sequence
<220> FEATURE:
<223> OTHER INFORMATION: Synthetic

<400> SEQUENCE: 11

Cys Tyr Ser Asn Ser Gly Cys
1               5

<210> SEQ ID NO 12
<211> LENGTH: 7
<212> TYPE: PRT
<213> ORGANISM: Artificial sequence
<220> FEATURE:
<223> OTHER INFORMATION: Synthetic

<400> SEQUENCE: 12

Gly Asn Lys Arg Thr Arg Gly
1               5

<210> SEQ ID NO 13
<211> LENGTH: 9
<212> TYPE: PRT
<213> ORGANISM: Artificial sequence
<220> FEATURE:
<223> OTHER INFORMATION: Synthetic

<400> SEQUENCE: 13

Cys Gly Thr Arg Thr Arg Arg Arg Cys
1               5

<210> SEQ ID NO 14
<211> LENGTH: 6
<212> TYPE: PRT
<213> ORGANISM: Artificial sequence
<220> FEATURE:
<223> OTHER INFORMATION: Synthetic

<400> SEQUENCE: 14

Cys Ala Thr Pro Phe Cys
1               5
```

```
<210> SEQ ID NO 15
<211> LENGTH: 7
<212> TYPE: PRT
<213> ORGANISM: Artificial sequence
<220> FEATURE:
<223> OTHER INFORMATION: Synthetic

<400> SEQUENCE: 15

Cys Ala Val Pro Phe Tyr Cys
1               5

<210> SEQ ID NO 16
<211> LENGTH: 6
<212> TYPE: PRT
<213> ORGANISM: Artificial sequence
<220> FEATURE:
<223> OTHER INFORMATION: Synthetic

<400> SEQUENCE: 16

Cys Ala Glu Ala Val Cys
1               5

<210> SEQ ID NO 17
<211> LENGTH: 9
<212> TYPE: PRT
<213> ORGANISM: Artificial sequence
<220> FEATURE:
<223> OTHER INFORMATION: Synthetic

<400> SEQUENCE: 17

Cys Ala Thr Trp Leu Pro Pro Arg Cys
1               5

<210> SEQ ID NO 18
<211> LENGTH: 7
<212> TYPE: PRT
<213> ORGANISM: Artificial sequence
<220> FEATURE:
<223> OTHER INFORMATION: Synthetic

<400> SEQUENCE: 18

Thr Trp Leu Pro Ile Pro Arg
1               5

<210> SEQ ID NO 19
<211> LENGTH: 9
<212> TYPE: PRT
<213> ORGANISM: Artificial sequence
<220> FEATURE:
<223> OTHER INFORMATION: Synthetic

<400> SEQUENCE: 19

Cys His His His Pro His His Gly Cys
1               5

<210> SEQ ID NO 20
<211> LENGTH: 6
<212> TYPE: PRT
<213> ORGANISM: Artificial sequence
<220> FEATURE:
<223> OTHER INFORMATION: Synthetic

<400> SEQUENCE: 20

Pro Gln Pro Arg Pro Leu
1               5

<210> SEQ ID NO 21
```

```
<211> LENGTH: 8
<212> TYPE: PRT
<213> ORGANISM: Artificial sequence
<220> FEATURE:
<223> OTHER INFORMATION: Synthetic

<400> SEQUENCE: 21

Thr Thr His Trp Gly Phe Thr Cys
1               5

<210> SEQ ID NO 22
<211> LENGTH: 13
<212> TYPE: PRT
<213> ORGANISM: Artificial sequence
<220> FEATURE:
<223> OTHER INFORMATION: Synthetic

<400> SEQUENCE: 22

Cys Trp His Ser Asp Met Glu Trp Trp Tyr Leu Leu Cys
1               5                   10

<210> SEQ ID NO 23
<211> LENGTH: 10
<212> TYPE: PRT
<213> ORGANISM: Artificial sequence
<220> FEATURE:
<223> OTHER INFORMATION: Synthetic

<400> SEQUENCE: 23

Cys Asp Phe Lys Leu Phe Ala Val Tyr Cys
1               5                   10

<210> SEQ ID NO 24
<211> LENGTH: 7
<212> TYPE: PRT
<213> ORGANISM: Artificial sequence
<220> FEATURE:
<223> OTHER INFORMATION: Synthetic

<400> SEQUENCE: 24

Gly Gly Arg Gly Asp Gly Gly
1               5

<210> SEQ ID NO 25
<211> LENGTH: 11
<212> TYPE: PRT
<213> ORGANISM: Artificial sequence
<220> FEATURE:
<223> OTHER INFORMATION: Synthetic

<400> SEQUENCE: 25

Cys Asp Ala Ile Arg Met Trp Glu Trp Glu Cys
1               5                   10

<210> SEQ ID NO 26
<211> LENGTH: 12
<212> TYPE: PRT
<213> ORGANISM: Artificial sequence
<220> FEATURE:
<223> OTHER INFORMATION: Synthetic

<400> SEQUENCE: 26

Cys Ser Leu Tyr Tyr Ile Gln Gln Asp Thr Lys Cys
1               5                   10

<210> SEQ ID NO 27
<211> LENGTH: 10
```

```
<212> TYPE: PRT
<213> ORGANISM: Artificial sequence
<220> FEATURE:
<223> OTHER INFORMATION: Synthetic

<400> SEQUENCE: 27

Cys Trp Cys Phe Trp Lys Thr Cys Thr Cys
1               5                   10

<210> SEQ ID NO 28
<211> LENGTH: 6
<212> TYPE: PRT
<213> ORGANISM: Artificial sequence
<220> FEATURE:
<223> OTHER INFORMATION: Synthetic

<400> SEQUENCE: 28

Lys Asn Thr Asp Ser Arg
1               5

<210> SEQ ID NO 29
<211> LENGTH: 10
<212> TYPE: PRT
<213> ORGANISM: Artificial sequence
<220> FEATURE:
<223> OTHER INFORMATION: Synthetic

<400> SEQUENCE: 29

His Val Ala Tyr Val Leu Ile Lys Phe Cys
1               5                   10

<210> SEQ ID NO 30
<211> LENGTH: 15
<212> TYPE: PRT
<213> ORGANISM: Artificial sequence
<220> FEATURE:
<223> OTHER INFORMATION: Synthetic

<400> SEQUENCE: 30

Cys Arg Gly Lys Phe Lys Arg Pro Pro Leu Arg Arg Val Arg Cys
1               5                   10                  15

<210> SEQ ID NO 31
<211> LENGTH: 17
<212> TYPE: PRT
<213> ORGANISM: Artificial sequence
<220> FEATURE:
<223> OTHER INFORMATION: Synthetic

<400> SEQUENCE: 31

Cys Arg Gly Lys Gly Lys Gly Gln Lys Arg Lys Arg Lys Lys Ser Arg
1               5                   10                  15

Cys

<210> SEQ ID NO 32
<211> LENGTH: 7
<212> TYPE: PRT
<213> ORGANISM: Artificial sequence
<220> FEATURE:
<223> OTHER INFORMATION: Synthetic

<400> SEQUENCE: 32

Cys Arg Ala Val Lys Tyr Cys
1               5

<210> SEQ ID NO 33
```

```
<211> LENGTH: 7
<212> TYPE: PRT
<213> ORGANISM: Artificial sequence
<220> FEATURE:
<223> OTHER INFORMATION: Synthetic

<400> SEQUENCE: 33

Leu Leu Arg Met Arg Ser Ala
1               5

<210> SEQ ID NO 34
<211> LENGTH: 12
<212> TYPE: PRT
<213> ORGANISM: Artificial sequence
<220> FEATURE:
<223> OTHER INFORMATION: Synthetic

<400> SEQUENCE: 34

Cys Arg Asn Pro Asp Gly Asp Ala Lys Pro Trp Cys
1               5                   10

<210> SEQ ID NO 35
<211> LENGTH: 9
<212> TYPE: PRT
<213> ORGANISM: Artificial sequence
<220> FEATURE:
<223> OTHER INFORMATION: Synthetic

<400> SEQUENCE: 35

Cys Ser Tyr Pro Ile Pro Asp Thr Cys
1               5

<210> SEQ ID NO 36
<211> LENGTH: 8
<212> TYPE: PRT
<213> ORGANISM: Artificial sequence
<220> FEATURE:
<223> OTHER INFORMATION: Synthetic

<400> SEQUENCE: 36

Cys Ala Arg Pro Cys Ala Pro Gly
1               5

<210> SEQ ID NO 37
<211> LENGTH: 14
<212> TYPE: PRT
<213> ORGANISM: Artificial sequence
<220> FEATURE:
<223> OTHER INFORMATION: Synthetic

<400> SEQUENCE: 37

Cys Asp Trp Trp Pro Leu Ala Phe Glu Ala Leu Leu Arg Cys
1               5                   10

<210> SEQ ID NO 38
<211> LENGTH: 4
<212> TYPE: PRT
<213> ORGANISM: Artificial sequence
<220> FEATURE:
<223> OTHER INFORMATION: Synthetic

<400> SEQUENCE: 38

Trp Leu Asp Val
1

<210> SEQ ID NO 39
<211> LENGTH: 10
```

```
<212> TYPE: PRT
<213> ORGANISM: Artificial sequence
<220> FEATURE:
<223> OTHER INFORMATION: Synthetic

<400> SEQUENCE: 39

Cys Lys Gly Val Ser Leu Ser Tyr Arg Cys
1               5                   10

<210> SEQ ID NO 40
<211> LENGTH: 9
<212> TYPE: PRT
<213> ORGANISM: Artificial sequence
<220> FEATURE:
<223> OTHER INFORMATION: Synthetic

<400> SEQUENCE: 40

Cys Pro Arg Cys Gly Val Pro Asp Cys
1               5

<210> SEQ ID NO 41
<211> LENGTH: 7
<212> TYPE: PRT
<213> ORGANISM: Artificial sequence
<220> FEATURE:
<223> OTHER INFORMATION: Synthetic

<400> SEQUENCE: 41

Cys Lys Leu Leu Gly Gly Cys
1               5

<210> SEQ ID NO 42
<211> LENGTH: 7
<212> TYPE: PRT
<213> ORGANISM: Artificial sequence
<220> FEATURE:
<223> OTHER INFORMATION: Synthetic

<400> SEQUENCE: 42

Cys Glu Ile Leu Asp Val Cys
1               5

<210> SEQ ID NO 43
<211> LENGTH: 7
<212> TYPE: PRT
<213> ORGANISM: Artificial sequence
<220> FEATURE:
<223> OTHER INFORMATION: Synthetic

<400> SEQUENCE: 43

Cys Lys Leu Asp Thr Gly Cys
1               5

<210> SEQ ID NO 44
<211> LENGTH: 7
<212> TYPE: PRT
<213> ORGANISM: Artificial sequence
<220> FEATURE:
<223> OTHER INFORMATION: Synthetic

<400> SEQUENCE: 44

Cys Lys Leu Asp Ile Gly Cys
1               5

<210> SEQ ID NO 45
<211> LENGTH: 6
<212> TYPE: PRT
```

```
<213> ORGANISM: Artificial sequence
<220> FEATURE:
<223> OTHER INFORMATION: Synthetic

<400> SEQUENCE: 45

Cys Phe Ser Val Asn Cys
1               5

<210> SEQ ID NO 46
<211> LENGTH: 6
<212> TYPE: PRT
<213> ORGANISM: Artificial sequence
<220> FEATURE:
<223> OTHER INFORMATION: Synthetic

<400> SEQUENCE: 46

Cys Asn Leu Asp Val Cys
1               5

<210> SEQ ID NO 47
<211> LENGTH: 6
<212> TYPE: PRT
<213> ORGANISM: Artificial sequence
<220> FEATURE:
<223> OTHER INFORMATION: Synthetic

<400> SEQUENCE: 47

Cys His Gly Lys His Cys
1               5

<210> SEQ ID NO 48
<211> LENGTH: 6
<212> TYPE: PRT
<213> ORGANISM: Artificial sequence
<220> FEATURE:
<223> OTHER INFORMATION: Synthetic

<400> SEQUENCE: 48

Cys His Glu Glu Arg Cys
1               5

<210> SEQ ID NO 49
<211> LENGTH: 6
<212> TYPE: PRT
<213> ORGANISM: Artificial sequence
<220> FEATURE:
<223> OTHER INFORMATION: Synthetic

<400> SEQUENCE: 49

Cys Asp Gly Glu Ala Cys
1               5

<210> SEQ ID NO 50
<211> LENGTH: 7
<212> TYPE: PRT
<213> ORGANISM: Artificial sequence
<220> FEATURE:
<223> OTHER INFORMATION: Synthetic

<400> SEQUENCE: 50

Cys Gly Arg Gly Asp Ser Ala
1               5

<210> SEQ ID NO 51
<211> LENGTH: 7
<212> TYPE: PRT
<213> ORGANISM: Artificial sequence
```

```
<220> FEATURE:
<223> OTHER INFORMATION: Synthetic

<400> SEQUENCE: 51

Arg Gln Pro Gly Asn Asn Tyr
1               5

<210> SEQ ID NO 52
<211> LENGTH: 9
<212> TYPE: PRT
<213> ORGANISM: Artificial sequence
<220> FEATURE:
<223> OTHER INFORMATION: Synthetic

<400> SEQUENCE: 52

Cys Tyr Ser Pro Trp Thr Asn Phe Cys
1               5

<210> SEQ ID NO 53
<211> LENGTH: 8
<212> TYPE: PRT
<213> ORGANISM: Artificial sequence
<220> FEATURE:
<223> OTHER INFORMATION: Synthetic

<400> SEQUENCE: 53

Cys Tyr Leu Pro Gln Thr Val Cys
1               5

<210> SEQ ID NO 54
<211> LENGTH: 10
<212> TYPE: PRT
<213> ORGANISM: Artificial sequence
<220> FEATURE:
<223> OTHER INFORMATION: Synthetic

<400> SEQUENCE: 54

Cys Lys Leu Ala Gly Arg Trp Pro Val Cys
1               5                   10

<210> SEQ ID NO 55
<211> LENGTH: 7
<212> TYPE: PRT
<213> ORGANISM: Artificial sequence
<220> FEATURE:
<223> OTHER INFORMATION: Synthetic

<400> SEQUENCE: 55

Pro Pro Glu Trp Gln Trp Leu
1               5

<210> SEQ ID NO 56
<211> LENGTH: 10
<212> TYPE: PRT
<213> ORGANISM: Artificial sequence
<220> FEATURE:
<223> OTHER INFORMATION: Synthetic

<400> SEQUENCE: 56

Lys Asp Asn Lys Phe Asn Gly Lys Gly Pro
1               5                   10

<210> SEQ ID NO 57
<211> LENGTH: 8
<212> TYPE: PRT
<213> ORGANISM: Artificial sequence
<220> FEATURE:
```

<223> OTHER INFORMATION: Synthetic

<400> SEQUENCE: 57

Cys Arg Ile Leu Leu Leu Lys Cys
1               5

<210> SEQ ID NO 58
<211> LENGTH: 4
<212> TYPE: PRT
<213> ORGANISM: Artificial sequence
<220> FEATURE:
<223> OTHER INFORMATION: Synthetic

<400> SEQUENCE: 58

Cys Asp Asp Cys
1

<210> SEQ ID NO 59
<211> LENGTH: 6
<212> TYPE: PRT
<213> ORGANISM: Artificial sequence
<220> FEATURE:
<223> OTHER INFORMATION: Synthetic

<400> SEQUENCE: 59

Cys Arg Trp Trp Leu Cys
1               5

<210> SEQ ID NO 60
<211> LENGTH: 13
<212> TYPE: PRT
<213> ORGANISM: Artificial sequence
<220> FEATURE:
<223> OTHER INFORMATION: Synthetic

<400> SEQUENCE: 60

Cys Phe Leu Leu Lys Leu Ala Gly Arg Trp Pro Val Cys
1               5                   10

<210> SEQ ID NO 61
<211> LENGTH: 5
<212> TYPE: PRT
<213> ORGANISM: Artificial sequence
<220> FEATURE:
<223> OTHER INFORMATION: Synthetic

<400> SEQUENCE: 61

Cys Trp Leu Trp Cys
1               5

<210> SEQ ID NO 62
<211> LENGTH: 11
<212> TYPE: PRT
<213> ORGANISM: Artificial sequence
<220> FEATURE:
<223> OTHER INFORMATION: Synthetic

<400> SEQUENCE: 62

Cys Thr Gly Leu Ala Trp Glu Trp Trp Arg Cys
1               5                   10

<210> SEQ ID NO 63
<211> LENGTH: 12
<212> TYPE: PRT
<213> ORGANISM: Artificial sequence
<220> FEATURE:
<223> OTHER INFORMATION: Synthetic

```
<400> SEQUENCE: 63

Phe Leu Gly Phe Leu Gly Ala Ala Gly Ser Thr Met
1               5                   10

<210> SEQ ID NO 64
<211> LENGTH: 14
<212> TYPE: PRT
<213> ORGANISM: Artificial sequence
<220> FEATURE:
<223> OTHER INFORMATION: Synthetic

<400> SEQUENCE: 64

Cys Gly Gly Ala Val Val Thr Gly Val Thr Ala Val Ala Cys
1               5                   10

<210> SEQ ID NO 65
<211> LENGTH: 12
<212> TYPE: PRT
<213> ORGANISM: Artificial sequence
<220> FEATURE:
<223> OTHER INFORMATION: Synthetic

<400> SEQUENCE: 65

Cys Trp Gly Leu Ala Trp Glu Trp Trp Arg Trp Cys
1               5                   10

<210> SEQ ID NO 66
<211> LENGTH: 13
<212> TYPE: PRT
<213> ORGANISM: Artificial sequence
<220> FEATURE:
<223> OTHER INFORMATION: Synthetic

<400> SEQUENCE: 66

Cys Ile Ala Thr Tyr Arg Lys Leu Leu Glu Ile Leu Cys
1               5                   10

<210> SEQ ID NO 67
<211> LENGTH: 10
<212> TYPE: PRT
<213> ORGANISM: Artificial sequence
<220> FEATURE:
<223> OTHER INFORMATION: Synthetic

<400> SEQUENCE: 67

Cys Glu Gly Lys Arg Pro Trp Ile Leu Cys
1               5                   10

<210> SEQ ID NO 68
<211> LENGTH: 11
<212> TYPE: PRT
<213> ORGANISM: Artificial sequence
<220> FEATURE:
<223> OTHER INFORMATION: Synthetic

<400> SEQUENCE: 68

Cys Ser His Leu Arg Lys Val Phe Asp Lys Cys
1               5                   10

<210> SEQ ID NO 69
<211> LENGTH: 16
<212> TYPE: PRT
<213> ORGANISM: Artificial sequence
<220> FEATURE:
<223> OTHER INFORMATION: Synthetic
```

<400> SEQUENCE: 69

Cys Leu Leu His Ile Ser Leu Leu Leu Ile Glu Ser Arg Leu Glu Cys
1               5                   10                  15

<210> SEQ ID NO 70
<211> LENGTH: 8
<212> TYPE: PRT
<213> ORGANISM: Artificial sequence
<220> FEATURE:
<223> OTHER INFORMATION: Synthetic

<400> SEQUENCE: 70

Cys Lys Pro Gln Leu Trp Pro Cys
1               5

<210> SEQ ID NO 71
<211> LENGTH: 8
<212> TYPE: PRT
<213> ORGANISM: Artificial sequence
<220> FEATURE:
<223> OTHER INFORMATION: Synthetic

<400> SEQUENCE: 71

Cys Lys Ala Gln Ala Trp Ala Cys
1               5

<210> SEQ ID NO 72
<211> LENGTH: 8
<212> TYPE: PRT
<213> ORGANISM: Artificial sequence
<220> FEATURE:
<223> OTHER INFORMATION: Synthetic

<400> SEQUENCE: 72

Lys Arg Leu Lys Glu Lys His Cys
1               5

<210> SEQ ID NO 73
<211> LENGTH: 7
<212> TYPE: PRT
<213> ORGANISM: Artificial sequence
<220> FEATURE:
<223> OTHER INFORMATION: Synthetic

<400> SEQUENCE: 73

Cys Met Glu Glu Val Asp Cys
1               5

<210> SEQ ID NO 74
<211> LENGTH: 10
<212> TYPE: PRT
<213> ORGANISM: Artificial sequence
<220> FEATURE:
<223> OTHER INFORMATION: Synthetic

<400> SEQUENCE: 74

Cys Gly Pro Thr Ile Glu Glu Val Asp Cys
1               5                   10

<210> SEQ ID NO 75
<211> LENGTH: 5
<212> TYPE: PRT
<213> ORGANISM: Artificial Sequence
<220> FEATURE:
<223> OTHER INFORMATION: Synthetic

<400> SEQUENCE: 75

```
Cys Lys Asp Ile Cys
1               5

<210> SEQ ID NO 76
<211> LENGTH: 9
<212> TYPE: PRT
<213> ORGANISM: Artificial sequence
<220> FEATURE:
<223> OTHER INFORMATION: Synthetic

<400> SEQUENCE: 76

Cys Tyr Asp Pro Trp Thr Pro Ser Cys
1               5

<210> SEQ ID NO 77
<211> LENGTH: 5
<212> TYPE: PRT
<213> ORGANISM: Artificial sequence
<220> FEATURE:
<223> OTHER INFORMATION: Synthetic

<400> SEQUENCE: 77

Cys Gly Pro Glu Cys
1               5

<210> SEQ ID NO 78
<211> LENGTH: 14
<212> TYPE: PRT
<213> ORGANISM: Artificial sequence
<220> FEATURE:
<223> OTHER INFORMATION: Synthetic

<400> SEQUENCE: 78

Cys Glu Ala Glu Lys Asn Arg Lys Leu Ala Asp Ile Ile Cys
1               5                   10

<210> SEQ ID NO 79
<211> LENGTH: 11
<212> TYPE: PRT
<213> ORGANISM: Artificial sequence
<220> FEATURE:
<223> OTHER INFORMATION: Synthetic

<400> SEQUENCE: 79

Cys Pro Arg Phe Lys Glu Tyr Phe Met Gln Cys
1               5                   10

<210> SEQ ID NO 80
<211> LENGTH: 11
<212> TYPE: PRT
<213> ORGANISM: Artificial sequence
<220> FEATURE:
<223> OTHER INFORMATION: Synthetic

<400> SEQUENCE: 80

Cys Ser Val Phe Tyr Asn Tyr Phe His Ser Cys
1               5                   10

<210> SEQ ID NO 81
<211> LENGTH: 11
<212> TYPE: PRT
<213> ORGANISM: Artificial sequence
<220> FEATURE:
<223> OTHER INFORMATION: Synthetic

<400> SEQUENCE: 81
```

Cys Leu Phe Ser Asn Leu Phe Tyr Gly Thr Cys
1               5                   10

<210> SEQ ID NO 82
<211> LENGTH: 11
<212> TYPE: PRT
<213> ORGANISM: Artificial sequence
<220> FEATURE:
<223> OTHER INFORMATION: Synthetic

<400> SEQUENCE: 82

Cys Val His His Gln Lys Leu Val Phe Phe Cys
1               5                   10

<210> SEQ ID NO 83
<211> LENGTH: 8
<212> TYPE: PRT
<213> ORGANISM: Artificial sequence
<220> FEATURE:
<223> OTHER INFORMATION: Synthetic

<400> SEQUENCE: 83

Cys Tyr Val Gln Ile Phe Phe Cys
1               5

<210> SEQ ID NO 84
<211> LENGTH: 8
<212> TYPE: PRT
<213> ORGANISM: Artificial sequence
<220> FEATURE:
<223> OTHER INFORMATION: Synthetic

<400> SEQUENCE: 84

Cys Tyr Leu Val Phe Phe Phe Cys
1               5

<210> SEQ ID NO 85
<211> LENGTH: 14
<212> TYPE: PRT
<213> ORGANISM: Artificial sequence
<220> FEATURE:
<223> OTHER INFORMATION: Synthetic

<400> SEQUENCE: 85

Cys Arg Pro Arg Thr Arg Leu His Thr His Arg Asn Arg Cys
1               5                   10

<210> SEQ ID NO 86
<211> LENGTH: 12
<212> TYPE: PRT
<213> ORGANISM: artificial sequence
<220> FEATURE:
<223> OTHER INFORMATION: Synthetic

<400> SEQUENCE: 86

Cys Trp Lys Trp Trp Pro Trp Lys Trp Trp Pro Cys
1               5                   10

<210> SEQ ID NO 87
<211> LENGTH: 13
<212> TYPE: PRT
<213> ORGANISM: Artificial sequence
<220> FEATURE:
<223> OTHER INFORMATION: Synthetic

<400> SEQUENCE: 87

Cys Ser Asn Trp Lys Trp Trp Pro Gly Ile Phe Asp Cys

```
<210> SEQ ID NO 88
<211> LENGTH: 14
<212> TYPE: PRT
<213> ORGANISM: Artificial sequence
<220> FEATURE:
<223> OTHER INFORMATION: Synthetic

<400> SEQUENCE: 88

Cys Thr Gly Asn Tyr Lys Ala Leu His Pro His Asn Gly Cys
1               5                   10

<210> SEQ ID NO 89
<211> LENGTH: 5
<212> TYPE: PRT
<213> ORGANISM: Artificial sequence
<220> FEATURE:
<223> OTHER INFORMATION: Synthetic

<400> SEQUENCE: 89

Cys Ser Val Thr Cys
1               5

<210> SEQ ID NO 90
<211> LENGTH: 14
<212> TYPE: PRT
<213> ORGANISM: Artificial sequence
<220> FEATURE:
<223> OTHER INFORMATION: Synthetic

<400> SEQUENCE: 90

Cys Ser Ala His Gly Thr Ser Thr Gly Val Pro Trp Pro Cys
1               5                   10

<210> SEQ ID NO 91
<211> LENGTH: 9
<212> TYPE: PRT
<213> ORGANISM: Artificial sequence
<220> FEATURE:
<223> OTHER INFORMATION: Synthetic

<400> SEQUENCE: 91

Cys Leu Lys Lys Thr Glu Thr Gln Cys
1               5

<210> SEQ ID NO 92
<211> LENGTH: 11
<212> TYPE: PRT
<213> ORGANISM: Artificial sequence
<220> FEATURE:
<223> OTHER INFORMATION: Synthetic

<400> SEQUENCE: 92

Lys Ala Phe Asp Ile Thr Tyr Val Arg Leu Lys
1               5                   10

<210> SEQ ID NO 93
<211> LENGTH: 11
<212> TYPE: PRT
<213> ORGANISM: Artificial sequence
<220> FEATURE:
<223> OTHER INFORMATION: Synthetic

<400> SEQUENCE: 93

Cys Ala Glu Tyr Trp Ala Leu Leu Ser Pro Cys
1               5                   10
```

<210> SEQ ID NO 94
<211> LENGTH: 6
<212> TYPE: PRT
<213> ORGANISM: Artificial sequence
<220> FEATURE:
<223> OTHER INFORMATION: Synthetic

<400> SEQUENCE: 94

Cys Phe Trp Lys Thr Cys
1               5

<210> SEQ ID NO 95
<211> LENGTH: 10
<212> TYPE: PRT
<213> ORGANISM: Artificial sequence
<220> FEATURE:
<223> OTHER INFORMATION: Synthetic

<400> SEQUENCE: 95

Cys Gly Leu Ile Ile Gln Lys Asn Glu Cys
1               5                   10

<210> SEQ ID NO 96
<211> LENGTH: 7
<212> TYPE: PRT
<213> ORGANISM: Artificial Sequence
<220> FEATURE:
<223> OTHER INFORMATION: Synthetic

<400> SEQUENCE: 96

Lys Pro His Ser Cys Asn Ala
1               5

<210> SEQ ID NO 97
<211> LENGTH: 14
<212> TYPE: PRT
<213> ORGANISM: Artificial sequence
<220> FEATURE:
<223> OTHER INFORMATION: Synthetic

<400> SEQUENCE: 97

Cys Asp Phe Lys Leu Phe Ala Val Tyr Ile Lys Tyr Arg Cys
1               5                   10

<210> SEQ ID NO 98
<211> LENGTH: 7
<212> TYPE: PRT
<213> ORGANISM: Artificial Sequence
<220> FEATURE:
<223> OTHER INFORMATION: Synthetic

<400> SEQUENCE: 98

Cys Pro His Ser Arg Asn Cys
1               5

<210> SEQ ID NO 99
<211> LENGTH: 28
<212> TYPE: PRT
<213> ORGANISM: Artificial sequence
<220> FEATURE:
<223> OTHER INFORMATION: Cyclic peptide and D-peptide analogs

<400> SEQUENCE: 99

Cys Gln Gly Thr Ser Asn Lys Leu Thr Gln Leu Gly Thr Phe Glu Asp
1               5                   10                  15

```
His Phe Leu Ser Leu Gln Arg Met Phe Asn Asn Cys
            20                  25
```

<210> SEQ ID NO 100
<211> LENGTH: 31
<212> TYPE: PRT
<213> ORGANISM: Artificial sequence
<220> FEATURE:
<223> OTHER INFORMATION: Cyclic peptide and D-peptide analogs

<400> SEQUENCE: 100

```
Cys Asn Val Glu Ser Ile Gln Trp Arg Asp Ile Val Ser Ser Asp Phe
1               5                   10                  15

Leu Ser Asn Met Ser Met Asp Phe Gln Asn His Leu Gly Ser Cys
            20                  25                  30
```

<210> SEQ ID NO 101
<211> LENGTH: 18
<212> TYPE: PRT
<213> ORGANISM: Artificial sequence
<220> FEATURE:
<223> OTHER INFORMATION: Cyclic peptide and D-peptide analogs

<400> SEQUENCE: 101

```
Cys Asp Pro Ser Cys Pro Asn Gly Ser Cys Trp Gly Ala Gly Glu Glu
1               5                   10                  15

Asn Cys
```

<210> SEQ ID NO 102
<211> LENGTH: 17
<212> TYPE: PRT
<213> ORGANISM: Artificial sequence
<220> FEATURE:
<223> OTHER INFORMATION: Cyclic peptide and D-peptide analogs

<400> SEQUENCE: 102

```
Cys Ala Gln Gln Cys Ser Gly Arg Cys Arg Gly Lys Ser Pro Ser Asp
1               5                   10                  15

Cys
```

<210> SEQ ID NO 103
<211> LENGTH: 17
<212> TYPE: PRT
<213> ORGANISM: Artificial sequence
<220> FEATURE:
<223> OTHER INFORMATION: Cyclic peptide and D-peptide analogs

<400> SEQUENCE: 103

```
Cys His Asn Gln Cys Ala Ala Gly Cys Thr Gly Pro Arg Glu Ser Asp
1               5                   10                  15

Cys
```

<210> SEQ ID NO 104
<211> LENGTH: 10
<212> TYPE: PRT
<213> ORGANISM: Artificial sequence
<220> FEATURE:
<223> OTHER INFORMATION: Cyclic peptide and D-peptide analogs

<400> SEQUENCE: 104

```
Cys Arg Lys Phe Arg Asp Glu Ala Thr Cys
1               5                   10
```

<210> SEQ ID NO 105

```
<211> LENGTH: 28
<212> TYPE: PRT
<213> ORGANISM: Artificial sequence
<220> FEATURE:
<223> OTHER INFORMATION: Cyclic peptide and D-peptide analogs

<400> SEQUENCE: 105

Cys Pro Pro Leu Met Leu Tyr Asn Pro Thr Thr Tyr Gln Met Asp Val
1               5                   10                  15

Asn Pro Glu Gly Lys Tyr Ser Phe Gly Ala Thr Cys
            20                  25

<210> SEQ ID NO 106
<211> LENGTH: 13
<212> TYPE: PRT
<213> ORGANISM: Artificial sequence
<220> FEATURE:
<223> OTHER INFORMATION: Cyclic peptide and D-peptide analogs

<400> SEQUENCE: 106

Cys Pro Arg Asn Tyr Val Val Thr Asp His Gly Ser Cys
1               5                   10

<210> SEQ ID NO 107
<211> LENGTH: 16
<212> TYPE: PRT
<213> ORGANISM: Artificial sequence
<220> FEATURE:
<223> OTHER INFORMATION: Cyclic peptide and D-peptide analogs

<400> SEQUENCE: 107

Cys Gly Ala Asp Ser Tyr Glu Met Glu Glu Asp Gly Val Arg Lys Cys
1               5                   10                  15

<210> SEQ ID NO 108
<211> LENGTH: 5
<212> TYPE: PRT
<213> ORGANISM: Artificial sequence
<220> FEATURE:
<223> OTHER INFORMATION: D-peptide and analogs

<400> SEQUENCE: 108

Cys Val Pro Trp Cys
1               5

<210> SEQ ID NO 109
<211> LENGTH: 23
<212> TYPE: PRT
<213> ORGANISM: Artificial sequence
<220> FEATURE:
<223> OTHER INFORMATION: Cyclic peptide and D-peptide analogs

<400> SEQUENCE: 109

Cys Gly Ala Asp Ser Tyr Glu Met Glu Glu Asp Gly Val Arg Lys Cys
1               5                   10                  15

Lys Lys Cys Glu Gly Pro Cys
            20

<210> SEQ ID NO 110
<211> LENGTH: 26
<212> TYPE: PRT
<213> ORGANISM: Artificial sequence
<220> FEATURE:
<223> OTHER INFORMATION: Cyclic peptide and D-peptide analogs

<400> SEQUENCE: 110
```

```
Cys Asn Gly Ile Gly Ile Gly Glu Phe Lys Asp Ser Leu Ser Ile Asn
1               5                   10                  15

Ala Thr Asn Ile Lys His Phe Lys Asn Cys
            20                  25
```

<210> SEQ ID NO 111
<211> LENGTH: 30
<212> TYPE: PRT
<213> ORGANISM: Artificial sequence
<220> FEATURE:
<223> OTHER INFORMATION: Cyclic peptide and D-peptide analogs

<400> SEQUENCE: 111

```
Cys Tyr Ala Asn Thr Ile Asn Trp Lys Lys Leu Phe Gly Thr Ser Gly
1               5                   10                  15

Gln Lys Thr Lys Ile Ile Ser Asn Arg Gly Glu Asn Ser Cys
            20                  25                  30
```

<210> SEQ ID NO 112
<211> LENGTH: 18
<212> TYPE: PRT
<213> ORGANISM: Artificial sequence
<220> FEATURE:
<223> OTHER INFORMATION: Cyclic peptides and D-peptide analogs

<400> SEQUENCE: 112

```
Cys His Ala Leu Cys Ser Pro Glu Gly Cys Trp Gly Pro Glu Pro Arg
1               5                   10                  15

Asp Cys
```

<210> SEQ ID NO 113
<211> LENGTH: 10
<212> TYPE: PRT
<213> ORGANISM: Artificial sequence
<220> FEATURE:
<223> OTHER INFORMATION: Cyclic peptide and D-peptide analogs

<400> SEQUENCE: 113

```
Cys Arg Asn Val Ser Arg Gly Arg Glu Cys
1               5                   10
```

<210> SEQ ID NO 114
<211> LENGTH: 17
<212> TYPE: PRT
<213> ORGANISM: Artificial sequence
<220> FEATURE:
<223> OTHER INFORMATION: Cyclic peptide and D-peptide analogs

<400> SEQUENCE: 114

```
Cys Asn Leu Leu Glu Gly Glu Pro Arg Glu Phe Val Glu Asn Ser Glu
1               5                   10                  15

Cys
```

<210> SEQ ID NO 115
<211> LENGTH: 22
<212> TYPE: PRT
<213> ORGANISM: Artificial sequence
<220> FEATURE:
<223> OTHER INFORMATION: Cyclic peptide and D-peptide analogs

<400> SEQUENCE: 115

```
Cys His Pro Glu Cys Leu Pro Gln Ala Met Asn Ile Thr Cys Thr Gly
1               5                   10                  15

Arg Gly Pro Asp Asn Cys
```

```
            20

<210> SEQ ID NO 116
<211> LENGTH: 10
<212> TYPE: PRT
<213> ORGANISM: Artificial sequence
<220> FEATURE:
<223> OTHER INFORMATION: Cyclic peptide and D-peptide analogs

<400> SEQUENCE: 116

Cys Ala His Tyr Ile Asp Gly Pro His Cys
1               5                   10

<210> SEQ ID NO 117
<211> LENGTH: 23
<212> TYPE: PRT
<213> ORGANISM: Artificial sequence
<220> FEATURE:
<223> OTHER INFORMATION: Cyclic peptide and D-peptide analogs

<400> SEQUENCE: 117

Cys Pro Ala Gly Val Met Gly Glu Asn Asn Thr Leu Val Trp Lys Tyr
1               5                   10                  15

Ala Asp Ala Gly His Val Cys
            20

<210> SEQ ID NO 118
<211> LENGTH: 17
<212> TYPE: PRT
<213> ORGANISM: Artificial sequence
<220> FEATURE:
<223> OTHER INFORMATION: Cyclic peptide and D-peptide analogs

<400> SEQUENCE: 118

Cys His Pro Asn Cys Thr Tyr Gly Cys Thr Gly Pro Gly Leu Glu Gly
1               5                   10                  15

Cys

<210> SEQ ID NO 119
<211> LENGTH: 7
<212> TYPE: PRT
<213> ORGANISM: Artificial sequence
<220> FEATURE:
<223> OTHER INFORMATION: Cyclic peptide and D-peptide analogs

<400> SEQUENCE: 119

Cys Arg Leu Leu Gly Ile Cys
1               5

<210> SEQ ID NO 120
<211> LENGTH: 22
<212> TYPE: PRT
<213> ORGANISM: Artificial sequence
<220> FEATURE:
<223> OTHER INFORMATION: Cyclic peptide and D-peptide analogs

<400> SEQUENCE: 120

Cys Leu Leu Asp Tyr Val Arg Glu His Lys Asp Asn Ile Gly Ser Gln
1               5                   10                  15

Tyr Leu Leu Asn Trp Cys
            20

<210> SEQ ID NO 121
<211> LENGTH: 12
<212> TYPE: PRT
```

```
<213> ORGANISM: Artificial sequence
<220> FEATURE:
<223> OTHER INFORMATION: Cyclic peptide and D-peptide analogs

<400> SEQUENCE: 121

Cys Ser Leu Leu Gly Gly Arg Leu Leu Gly Gln Cys
1               5                   10

<210> SEQ ID NO 122
<211> LENGTH: 10
<212> TYPE: PRT
<213> ORGANISM: Artificial sequence
<220> FEATURE:
<223> OTHER INFORMATION: Cyclic peptides and D-peptide analogs

<400> SEQUENCE: 122

Cys Ile Asp Arg Asn Gly Leu Gln Ser Cys
1               5                   10

<210> SEQ ID NO 123
<211> LENGTH: 7
<212> TYPE: PRT
<213> ORGANISM: Artificial sequence
<220> FEATURE:
<223> OTHER INFORMATION: Cyclic peptide and D-peptide analogs

<400> SEQUENCE: 123

Cys Phe Asn Gly Arg Asp Cys
1               5

<210> SEQ ID NO 124
<211> LENGTH: 12
<212> TYPE: PRT
<213> ORGANISM: Artificial sequence
<220> FEATURE:
<223> OTHER INFORMATION: Linear peptide and D-peptide analogs

<400> SEQUENCE: 124

His Glu Val Val Lys Phe Met Asp Val Tyr Gln Arg
1               5                   10

<210> SEQ ID NO 125
<211> LENGTH: 20
<212> TYPE: PRT
<213> ORGANISM: Artificial sequence
<220> FEATURE:
<223> OTHER INFORMATION: Linear peptide and D-peptide analogs

<400> SEQUENCE: 125

Phe Leu Leu Ser Trp Val His Trp Ser Leu Ala Leu Leu Leu Tyr Leu
1               5                   10                  15

His His Ala Lys
            20

<210> SEQ ID NO 126
<211> LENGTH: 18
<212> TYPE: PRT
<213> ORGANISM: Artificial sequence
<220> FEATURE:
<223> OTHER INFORMATION: Cyclic peptide and D-peptide analogs

<400> SEQUENCE: 126

Cys Val Pro Leu Met Arg Cys Gly Gly Cys Cys Asn Asp Glu Gly Leu
1               5                   10                  15

Glu Cys
```

```
<210> SEQ ID NO 127
<211> LENGTH: 22
<212> TYPE: PRT
<213> ORGANISM: Artificial sequence
<220> FEATURE:
<223> OTHER INFORMATION: Cyclic peptide and D-peptide analogs

<400> SEQUENCE: 127

Cys Gly Pro Cys Ser Glu Arg Arg Lys His Leu Phe Val Gln Asp Pro
1               5                   10                  15

Gln Thr Cys Lys Cys Ser
            20

<210> SEQ ID NO 128
<211> LENGTH: 22
<212> TYPE: PRT
<213> ORGANISM: Artificial sequence
<220> FEATURE:
<223> OTHER INFORMATION: Cyclic peptide and D-peptide analogs

<400> SEQUENCE: 128

Cys Lys Asn Thr Asp Ser Arg Cys Lys Ala Arg Gln Leu Glu Leu Asn
1               5                   10                  15

Glu Arg Thr Cys Arg Cys
            20

<210> SEQ ID NO 129
<211> LENGTH: 16
<212> TYPE: PRT
<213> ORGANISM: Artificial sequence
<220> FEATURE:
<223> OTHER INFORMATION: Linear peptide and D-peptide analogs

<400> SEQUENCE: 129

His Ala Asn Arg Ile Tyr Arg Met Ile Lys Leu Gly Leu Gly Ile Asp
1               5                   10                  15

<210> SEQ ID NO 130
<211> LENGTH: 21
<212> TYPE: PRT
<213> ORGANISM: Artificial sequence
<220> FEATURE:
<223> OTHER INFORMATION: Linear peptide and D-peptide analogs

<400> SEQUENCE: 130

Lys Ile Met Lys Asp Ile Leu Glu Lys Lys Val Glu Lys Val Val Val
1               5                   10                  15

Ser Asn Arg Leu Val
            20

<210> SEQ ID NO 131
<211> LENGTH: 16
<212> TYPE: PRT
<213> ORGANISM: Artificial sequence
<220> FEATURE:
<223> OTHER INFORMATION: Linear peptide and D-peptide analogs

<400> SEQUENCE: 131

Gly Gln Phe Gly Val Gly Phe Tyr Ser Ala Tyr Leu Val Ala Glu Lys
1               5                   10                  15

<210> SEQ ID NO 132
<211> LENGTH: 7
<212> TYPE: PRT
<213> ORGANISM: Artificial sequence
```

```
<220> FEATURE:
<223> OTHER INFORMATION: Cyclic peptide and D-peptide analogs

<400> SEQUENCE: 132

Cys Met Glu Glu Val Asp Cys
1               5

<210> SEQ ID NO 133
<211> LENGTH: 13
<212> TYPE: PRT
<213> ORGANISM: Artificial sequence
<220> FEATURE:
<223> OTHER INFORMATION: Linear peptide and D-peptide analogs

<400> SEQUENCE: 133

Thr Thr Pro Ser Tyr Val Ala Phe Thr Asp Thr Glu Arg
1               5                   10

<210> SEQ ID NO 134
<211> LENGTH: 13
<212> TYPE: PRT
<213> ORGANISM: Artificial sequence
<220> FEATURE:
<223> OTHER INFORMATION: Linear peptide and D-peptide analogs

<400> SEQUENCE: 134

Lys Tyr Lys Ala Glu Asp Glu Val Gln Arg Glu Lys Ile
1               5                   10

<210> SEQ ID NO 135
<211> LENGTH: 10
<212> TYPE: PRT
<213> ORGANISM: Artificial sequence
<220> FEATURE:
<223> OTHER INFORMATION: Cyclic peptide and D-peptide analogs

<400> SEQUENCE: 135

Cys Gly Pro Thr Ile Glu Glu Val Asp Cys
1               5                   10

<210> SEQ ID NO 136
<211> LENGTH: 12
<212> TYPE: PRT
<213> ORGANISM: Artificial sequence
<220> FEATURE:
<223> OTHER INFORMATION: Linear peptide and D-peptide analogs

<400> SEQUENCE: 136

Ala Arg Phe Glu Glu Leu Asn Ala Asp Leu Phe Arg
1               5                   10

<210> SEQ ID NO 137
<211> LENGTH: 16
<212> TYPE: PRT
<213> ORGANISM: Artificial sequence
<220> FEATURE:
<223> OTHER INFORMATION: Linear peptide and D-peptide analogs

<400> SEQUENCE: 137

Ser Thr Ala Gly Asp Thr His Leu Gly Gly Glu Asp Phe Asp Asn Arg
1               5                   10                  15

<210> SEQ ID NO 138
<211> LENGTH: 14
<212> TYPE: PRT
<213> ORGANISM: Artificial sequence
<220> FEATURE:
```

```
<223> OTHER INFORMATION: Linear peptide and D-peptide analogs

<400> SEQUENCE: 138

Lys Leu Leu Gln Asp Phe Phe Asn Gly Lys Glu Leu Asn Lys
1               5                   10

<210> SEQ ID NO 139
<211> LENGTH: 15
<212> TYPE: PRT
<213> ORGANISM: Artificial sequence
<220> FEATURE:
<223> OTHER INFORMATION: Linear peptide and D-peptide analogs

<400> SEQUENCE: 139

Met Val Leu Thr Lys Met Lys Glu Ile Ala Glu Ala Tyr Leu Gly
1               5                   10                  15

<210> SEQ ID NO 140
<211> LENGTH: 16
<212> TYPE: PRT
<213> ORGANISM: Artificial sequence
<220> FEATURE:
<223> OTHER INFORMATION: Linear peptide and D-peptide analogs

<400> SEQUENCE: 140

Gln Ala Thr Lys Asp Ala Gly Val Ile Ala Gly Leu Asn Val Leu Arg
1               5                   10                  15

<210> SEQ ID NO 141
<211> LENGTH: 16
<212> TYPE: PRT
<213> ORGANISM: Artificial sequence
<220> FEATURE:
<223> OTHER INFORMATION: Linear peptide and D-peptide analogs

<400> SEQUENCE: 141

Asn Gln Val Ala Met Asn Pro Thr Asn Thr Val Phe Asp Ala Lys Arg
1               5                   10                  15

<210> SEQ ID NO 142
<211> LENGTH: 12
<212> TYPE: PRT
<213> ORGANISM: Artificial sequence
<220> FEATURE:
<223> OTHER INFORMATION: Linear peptide and D-peptide analogs

<400> SEQUENCE: 142

Arg Phe Asp Asp Ala Val Val Gln Ser Asp Met Lys
1               5                   10

<210> SEQ ID NO 143
<211> LENGTH: 5
<212> TYPE: PRT
<213> ORGANISM: Artificial sequence
<220> FEATURE:
<223> OTHER INFORMATION: Cyclic peptide and D-peptide analogs

<400> SEQUENCE: 143

Cys Leu Asp Val Cys
1               5

<210> SEQ ID NO 144
<211> LENGTH: 10
<212> TYPE: PRT
<213> ORGANISM: Artificial sequence
<220> FEATURE:
<223> OTHER INFORMATION: Linear peptide and D-peptide analogs
```

```
<400> SEQUENCE: 144

Met Val Asn His Phe Ile Ala Glu Phe Lys
1               5                   10

<210> SEQ ID NO 145
<211> LENGTH: 13
<212> TYPE: PRT
<213> ORGANISM: Artificial sequence
<220> FEATURE:
<223> OTHER INFORMATION: Linear peptide and D-peptide analogs

<400> SEQUENCE: 145

Arg Ile Met Ser Ser Ala Lys Arg Pro Leu Trp Leu Asn
1               5                   10

<210> SEQ ID NO 146
<211> LENGTH: 16
<212> TYPE: PRT
<213> ORGANISM: Artificial sequence
<220> FEATURE:
<223> OTHER INFORMATION: Linear peptide and D-peptide analogs

<400> SEQUENCE: 146

Gly Leu Ile Glu Val Val Arg Asn Ser His Thr Ile Met Gln Ile Gln
1               5                   10                  15

<210> SEQ ID NO 147
<211> LENGTH: 7
<212> TYPE: PRT
<213> ORGANISM: Artificial sequence
<220> FEATURE:
<223> OTHER INFORMATION: Linear peptide and D-peptide analogs

<400> SEQUENCE: 147

Ile Phe Lys Asn Gly Asp Asp
1               5

<210> SEQ ID NO 148
<211> LENGTH: 14
<212> TYPE: PRT
<213> ORGANISM: Artificial sequence
<220> FEATURE:
<223> OTHER INFORMATION: Linear peptide and D-peptide analogs

<400> SEQUENCE: 148

Gly Gln Leu Phe His Ile Asp Phe Gly His Phe Leu Asp His
1               5                   10

<210> SEQ ID NO 149
<211> LENGTH: 10
<212> TYPE: PRT
<213> ORGANISM: Artificial sequence
<220> FEATURE:
<223> OTHER INFORMATION: Linear peptide and D-peptide analogs

<400> SEQUENCE: 149

Asp Arg His Asn Ser Asn Ile Met Val Lys
1               5                   10

<210> SEQ ID NO 150
<211> LENGTH: 15
<212> TYPE: PRT
<213> ORGANISM: Artificial sequence
<220> FEATURE:
<223> OTHER INFORMATION: Linear peptide and D-peptide analogs
```

```
<400> SEQUENCE: 150

Glu Val Val Gly Arg Gly Ala Phe Gly Val Val Cys Lys Ala Lys
1               5                   10                  15

<210> SEQ ID NO 151
<211> LENGTH: 11
<212> TYPE: PRT
<213> ORGANISM: Artificial sequence
<220> FEATURE:
<223> OTHER INFORMATION: Linear peptide and D-peptide analogs

<400> SEQUENCE: 151

Arg Ala Lys Asp Val Ala Ile Lys Gln Ile Glu
1               5                   10

<210> SEQ ID NO 152
<211> LENGTH: 19
<212> TYPE: PRT
<213> ORGANISM: Artificial sequence
<220> FEATURE:
<223> OTHER INFORMATION: Linear peptide and D-peptide analogs

<400> SEQUENCE: 152

Asn Leu Leu Leu Val Ala Gly Gly Thr Val Leu Lys Ile Cys Asp Phe
1               5                   10                  15

Gly Thr Ala

<210> SEQ ID NO 153
<211> LENGTH: 9
<212> TYPE: PRT
<213> ORGANISM: Artificial sequence
<220> FEATURE:
<223> OTHER INFORMATION: Linear peptide and D-peptide analogs

<400> SEQUENCE: 153

Val Ile Thr Ser Lys Gln Arg Pro Arg
1               5

<210> SEQ ID NO 154
<211> LENGTH: 8
<212> TYPE: PRT
<213> ORGANISM: Artificial sequence
<220> FEATURE:
<223> OTHER INFORMATION: Linear peptide and D-peptide analogs

<400> SEQUENCE: 154

Phe Leu Leu Lys Gly His Glu Asp
1               5

<210> SEQ ID NO 155
<211> LENGTH: 5
<212> TYPE: PRT
<213> ORGANISM: Artificial sequence
<220> FEATURE:
<223> OTHER INFORMATION: Linear peptide and D-peptide analogs

<400> SEQUENCE: 155

Ser Asn Leu Met Leu
1               5

<210> SEQ ID NO 156
<211> LENGTH: 10
<212> TYPE: PRT
<213> ORGANISM: Artificial sequence
<220> FEATURE:
<223> OTHER INFORMATION: Cyclic peptide and D-peptide analogs
```

<400> SEQUENCE: 156

Cys Ile Gly Trp Val Pro His Cys Asp Thr
1               5                   10

<210> SEQ ID NO 157
<211> LENGTH: 15
<212> TYPE: PRT
<213> ORGANISM: Artificial sequence
<220> FEATURE:
<223> OTHER INFORMATION: Linear peptide and D-peptide analogs

<400> SEQUENCE: 157

Thr Gln Ala Trp Asp Leu Tyr Tyr His Val Phe Arg Arg Ile Ser
1               5                   10                  15

<210> SEQ ID NO 158
<211> LENGTH: 13
<212> TYPE: PRT
<213> ORGANISM: Artificial sequence
<220> FEATURE:
<223> OTHER INFORMATION: Linear peptide and D-peptide analogs

<400> SEQUENCE: 158

His Glu Gly Leu Glu Glu Ala Ser Arg Leu Tyr Phe Gly
1               5                   10

<210> SEQ ID NO 159
<211> LENGTH: 14
<212> TYPE: PRT
<213> ORGANISM: Artificial sequence
<220> FEATURE:
<223> OTHER INFORMATION: Linear peptide and D-peptide analogs

<400> SEQUENCE: 159

Arg Val Met Gln Leu Phe Gly Leu Val Asn Thr Leu Leu Ala
1               5                   10

<210> SEQ ID NO 160
<211> LENGTH: 13
<212> TYPE: PRT
<213> ORGANISM: Artificial sequence
<220> FEATURE:
<223> OTHER INFORMATION: Linear peptide and D-peptide analogs

<400> SEQUENCE: 160

Lys Ile Leu Leu Asn Ile Glu His Arg Ile Met Leu Arg
1               5                   10

<210> SEQ ID NO 161
<211> LENGTH: 9
<212> TYPE: PRT
<213> ORGANISM: Artificial sequence
<220> FEATURE:
<223> OTHER INFORMATION: Linear peptide and D-peptide analogs

<400> SEQUENCE: 161

Asp Leu Ala Lys Leu Leu Trp Leu Lys
1               5

<210> SEQ ID NO 162
<211> LENGTH: 13
<212> TYPE: PRT
<213> ORGANISM: Artificial sequence
<220> FEATURE:
<223> OTHER INFORMATION: Linear peptide and D-peptide analogs

```
<400> SEQUENCE: 162

Ser Leu Ala Val Met Ser Met Val Gly Tyr Ile Leu Gly
1               5                   10

<210> SEQ ID NO 163
<211> LENGTH: 16
<212> TYPE: PRT
<213> ORGANISM: Artificial sequence
<220> FEATURE:
<223> OTHER INFORMATION: Linear peptide and D-peptide analogs

<400> SEQUENCE: 163

Arg Leu Thr Arg Met Leu Thr Asn Ala Met Glu Val Thr Gly Leu Asp
1               5                   10                  15

<210> SEQ ID NO 164
<211> LENGTH: 8
<212> TYPE: PRT
<213> ORGANISM: Artificial sequence
<220> FEATURE:
<223> OTHER INFORMATION: Linear peptide and D-peptide analogs

<400> SEQUENCE: 164

His Thr Val Met Glu Val Leu Arg
1               5

<210> SEQ ID NO 165
<211> LENGTH: 10
<212> TYPE: PRT
<213> ORGANISM: Artificial sequence
<220> FEATURE:
<223> OTHER INFORMATION: Linear peptide and D-peptide analogs

<400> SEQUENCE: 165

Gly Arg Gly Ala Phe Gly Gln Val Ile Glu
1               5                   10

<210> SEQ ID NO 166
<211> LENGTH: 9
<212> TYPE: PRT
<213> ORGANISM: Artificial sequence
<220> FEATURE:
<223> OTHER INFORMATION: linear peptide and D-peptide analogs

<400> SEQUENCE: 166

Arg Thr Val Ala Val Lys Met Leu Lys
1               5

<210> SEQ ID NO 167
<211> LENGTH: 16
<212> TYPE: PRT
<213> ORGANISM: Artificial sequence
<220> FEATURE:
<223> OTHER INFORMATION: Linear peptide and D-peptide analogs

<400> SEQUENCE: 167

Val Ile Val Glu Phe Cys Lys Phe Gly Asn Leu Ser Thr Tyr Leu Arg
1               5                   10                  15

<210> SEQ ID NO 168
<211> LENGTH: 5
<212> TYPE: PRT
<213> ORGANISM: Artificial sequence
<220> FEATURE:
<223> OTHER INFORMATION: Cyclic peptide and D-peptide analogs

<400> SEQUENCE: 168
```

```
Cys Leu Asp Thr Cys
1               5

<210> SEQ ID NO 169
<211> LENGTH: 8
<212> TYPE: PRT
<213> ORGANISM: Artificial sequence
<220> FEATURE:
<223> OTHER INFORMATION: Linear peptide and D-peptide analogs

<400> SEQUENCE: 169

Gly Asp Ala Arg Leu Pro Leu Lys
1               5

<210> SEQ ID NO 170
<211> LENGTH: 11
<212> TYPE: PRT
<213> ORGANISM: Artificial sequence
<220> FEATURE:
<223> OTHER INFORMATION: Linear peptide and D-peptide analogs

<400> SEQUENCE: 170

Val Leu Gly Ser Gly Ala Phe Gly Lys Val Val
1               5                   10

<210> SEQ ID NO 171
<211> LENGTH: 10
<212> TYPE: PRT
<213> ORGANISM: Artificial sequence
<220> FEATURE:
<223> OTHER INFORMATION: Linear peptide and D-peptide analogs

<400> SEQUENCE: 171

Val Met Lys Val Ala Val Lys Met Leu Lys
1               5                   10

<210> SEQ ID NO 172
<211> LENGTH: 9
<212> TYPE: PRT
<213> ORGANISM: Artificial sequence
<220> FEATURE:
<223> OTHER INFORMATION: Linear peptide and D-peptide analogs

<400> SEQUENCE: 172

Ile Thr Glu Tyr Cys Phe Tyr Gly Asp
1               5

<210> SEQ ID NO 173
<211> LENGTH: 9
<212> TYPE: PRT
<213> ORGANISM: Artificial sequence
<220> FEATURE:
<223> OTHER INFORMATION: Linear peptide and D-peptide analogs

<400> SEQUENCE: 173

Arg Asp Leu Ala Ala Arg Asn Val Leu
1               5

<210> SEQ ID NO 174
<211> LENGTH: 11
<212> TYPE: PRT
<213> ORGANISM: Artificial sequence
<220> FEATURE:
<223> OTHER INFORMATION: Linear peptide and D-peptide analogs

<400> SEQUENCE: 174
```

```
Thr Met Lys Val Ala Val Lys Met Leu Lys Ser
1               5                   10
```

<210> SEQ ID NO 175
<211> LENGTH: 15
<212> TYPE: PRT
<213> ORGANISM: Artificial sequence
<220> FEATURE:
<223> OTHER INFORMATION: Linear peptide and D-peptide analogs

<400> SEQUENCE: 175

```
Arg Thr Leu Gly Ser Gly Ala Phe Gly Gln Val Val Glu Ala Thr
1               5                   10                  15
```

<210> SEQ ID NO 176
<211> LENGTH: 9
<212> TYPE: PRT
<213> ORGANISM: Artificial sequence
<220> FEATURE:
<223> OTHER INFORMATION: Linear peptide and D-peptide analogs

<400> SEQUENCE: 176

```
Ile Thr Glu Tyr Cys Arg Tyr Gly Asp
1               5
```

<210> SEQ ID NO 177
<211> LENGTH: 53
<212> TYPE: PRT
<213> ORGANISM: Artificial sequence
<220> FEATURE:
<223> OTHER INFORMATION: Cyclic peptide and D-peptide analogs

<400> SEQUENCE: 177

```
Cys Pro Asp Ser Gln Phe Glu Cys Pro Asp Phe Ser Thr Cys Cys Val
1               5                   10                  15

Met Val Asp Gly Ser Trp Gly Cys Cys Pro Met Pro Gln Ala Ser Cys
                20                  25                  30

Cys Glu Asp Arg Val His Cys Cys Pro His Gly Ala Phe Cys Asp Leu
            35                  40                  45

Val His Thr Arg Cys
            50
```

<210> SEQ ID NO 178
<211> LENGTH: 24
<212> TYPE: PRT
<213> ORGANISM: Artificial sequence
<220> FEATURE:
<223> OTHER INFORMATION: Cyclic peptide and D-peptide analogs

<400> SEQUENCE: 178

```
Cys Pro Asp Ser Gln Phe Glu Cys Pro Asp Phe Ser Thr Cys Cys Val
1               5                   10                  15

Met Val Asp Gly Ser Trp Gly Cys
                20
```

<210> SEQ ID NO 179
<211> LENGTH: 29
<212> TYPE: PRT
<213> ORGANISM: Artificial sequence
<220> FEATURE:
<223> OTHER INFORMATION: Cyclic peptide and D-peptide analogs

<400> SEQUENCE: 179

```
Cys Pro Met Pro Gln Ala Ser Cys Cys Glu Asp Arg Val His Cys Cys
1               5                   10                  15
```

```
Pro His Gly Ala Phe Cys Asp Leu Val His Thr Arg Cys
            20                  25
```

```
<210> SEQ ID NO 180
<211> LENGTH: 18
<212> TYPE: PRT
<213> ORGANISM: Artificial sequence
<220> FEATURE:
<223> OTHER INFORMATION: Cyclic peptide and D-peptide analogs

<400> SEQUENCE: 180

Cys Val Met Val Asp Gly Ser Trp Gly Cys Cys Pro Met Pro Gln Ala
1               5                   10                  15

Ser Cys
```

```
<210> SEQ ID NO 181
<211> LENGTH: 21
<212> TYPE: PRT
<213> ORGANISM: Artificial sequence
<220> FEATURE:
<223> OTHER INFORMATION: Cyclic peptide and D-peptide analogs

<400> SEQUENCE: 181

Cys Glu Asp Arg Val His Cys Cys Pro His Gly Ala Phe Cys Asp Leu
1               5                   10                  15

Val His Thr Arg Cys
            20
```

```
<210> SEQ ID NO 182
<211> LENGTH: 52
<212> TYPE: PRT
<213> ORGANISM: Artificial sequence
<220> FEATURE:
<223> OTHER INFORMATION: Cyclic peptide and D-peptide analogs

<400> SEQUENCE: 182

Cys Asp Gln His Thr Ser Cys Pro Val Gly Gln Thr Cys Cys Pro Ser
1               5                   10                  15

Leu Gly Gly Ser Trp Ala Cys Cys Gln Leu Pro His Ala Val Cys Cys
            20                  25                  30

Glu Asp Arg Gln His Cys Cys Pro Ala Gly Tyr Thr Cys Asn Val Lys
        35                  40                  45

Ala Arg Ser Cys
    50
```

```
<210> SEQ ID NO 183
<211> LENGTH: 23
<212> TYPE: PRT
<213> ORGANISM: Artificial sequence
<220> FEATURE:
<223> OTHER INFORMATION: Cyclic peptide and D-peptide analogs

<400> SEQUENCE: 183

Cys Asp Gln His Thr Ser Cys Pro Val Gly Gln Thr Cys Cys Pro Ser
1               5                   10                  15

Leu Gly Gly Ser Trp Ala Cys
            20
```

```
<210> SEQ ID NO 184
<211> LENGTH: 29
<212> TYPE: PRT
<213> ORGANISM: Artificial sequence
<220> FEATURE:
```

```
<223> OTHER INFORMATION: Cyclic peptide and D-peptide analogs

<400> SEQUENCE: 184

Cys Gln Leu Pro His Ala Val Cys Cys Glu Asp Arg Gln His Cys Cys
1               5                   10                  15

Pro Ala Gly Tyr Thr Cys Asn Val Lys Ala Arg Ser Cys
            20                  25

<210> SEQ ID NO 185
<211> LENGTH: 18
<212> TYPE: PRT
<213> ORGANISM: Artificial sequence
<220> FEATURE:
<223> OTHER INFORMATION: Cyclic peptide and D-peptide analogs

<400> SEQUENCE: 185

Cys Pro Ser Leu Gly Gly Ser Trp Ala Cys Cys Gln Leu Pro His Ala
1               5                   10                  15

Val Cys

<210> SEQ ID NO 186
<211> LENGTH: 21
<212> TYPE: PRT
<213> ORGANISM: Artificial sequence
<220> FEATURE:
<223> OTHER INFORMATION: Cyclic peptide and D-peptide analogs

<400> SEQUENCE: 186

Cys Glu Asp Arg Gln His Cys Cys Pro Ala Gly Tyr Thr Cys Asn Val
1               5                   10                  15

Lys Ala Arg Ser Cys
            20

<210> SEQ ID NO 187
<211> LENGTH: 52
<212> TYPE: PRT
<213> ORGANISM: Artificial sequence
<220> FEATURE:
<223> OTHER INFORMATION: Cyclic peptide and D-peptide analogs

<400> SEQUENCE: 187

Cys Asp Met Glu Val Ser Cys Pro Asp Gly Tyr Thr Cys Cys Arg Leu
1               5                   10                  15

Gln Ser Gly Ala Trp Gly Cys Cys Pro Phe Thr Gln Ala Val Cys Cys
            20                  25                  30

Glu Asp His Ile His Cys Cys Pro Ala Gly Phe Thr Cys Asp Thr Gln
        35                  40                  45

Lys Gly Thr Cys
    50

<210> SEQ ID NO 188
<211> LENGTH: 23
<212> TYPE: PRT
<213> ORGANISM: Artificial sequence
<220> FEATURE:
<223> OTHER INFORMATION: Cyclic peptide and D-peptide analogs

<400> SEQUENCE: 188

Cys Asp Met Glu Val Ser Cys Pro Asp Gly Tyr Thr Cys Cys Arg Leu
1               5                   10                  15

Gln Ser Gly Ala Trp Gly Cys
            20
```

<210> SEQ ID NO 189
<211> LENGTH: 29
<212> TYPE: PRT
<213> ORGANISM: Artificial sequence
<220> FEATURE:
<223> OTHER INFORMATION: Cyclic peptide and D-peptide analogs

<400> SEQUENCE: 189

Cys Pro Phe Thr Gln Ala Val Cys Cys Glu Asp His Ile His Cys Cys
1               5                   10                  15

Pro Ala Gly Phe Thr Cys Asp Thr Gln Lys Gly Thr Cys
            20                  25

<210> SEQ ID NO 190
<211> LENGTH: 18
<212> TYPE: PRT
<213> ORGANISM: Artificial sequence
<220> FEATURE:
<223> OTHER INFORMATION: Cyclic peptide and D-peptide analogs

<400> SEQUENCE: 190

Cys Arg Leu Gln Ser Gly Ala Trp Gly Cys Cys Pro Phe Thr Gln Ala
1               5                   10                  15

Val Cys

<210> SEQ ID NO 191
<211> LENGTH: 21
<212> TYPE: PRT
<213> ORGANISM: Artificial sequence
<220> FEATURE:
<223> OTHER INFORMATION: Cyclic peptide and D-peptide analogs

<400> SEQUENCE: 191

Cys Glu Asp His Ile His Cys Cys Pro Ala Gly Phe Thr Cys Asp Thr
1               5                   10                  15

Gln Lys Gly Thr Cys
            20

<210> SEQ ID NO 192
<211> LENGTH: 28
<212> TYPE: PRT
<213> ORGANISM: Artificial sequence
<220> FEATURE:
<223> OTHER INFORMATION: Cyclic peptide and D-peptide analogs

<400> SEQUENCE: 192

Cys Gly Gly Arg Leu Asn Ser Lys Asp Ala Gly Tyr Ile Thr Ser Pro
1               5                   10                  15

Gly Tyr Pro Gln Asp Tyr Pro Ser His Gln Asn Cys
            20                  25

<210> SEQ ID NO 193
<211> LENGTH: 27
<212> TYPE: PRT
<213> ORGANISM: Artificial sequence
<220> FEATURE:
<223> OTHER INFORMATION: Cyclic peptide and D-peptide analogs

<400> SEQUENCE: 193

Cys Ser Lys Asn Phe Thr Ser Pro Asn Gly Thr Ile Glu Ser Pro Gly
1               5                   10                  15

Phe Pro Glu Lys Tyr Pro His Asn Leu Asp Cys
            20                  25

```
<210> SEQ ID NO 194
<211> LENGTH: 23
<212> TYPE: PRT
<213> ORGANISM: Artificial sequence
<220> FEATURE:
<223> OTHER INFORMATION: Cyclic peptide and D-peptide analogs

<400> SEQUENCE: 194

Cys Lys Tyr Asp Trp Leu Asp Ile Trp Asp Gly Ile Pro His Val Gly
1               5                   10                  15

Pro Leu Ile Gly Lys Tyr Cys
            20

<210> SEQ ID NO 195
<211> LENGTH: 7
<212> TYPE: PRT
<213> ORGANISM: Artificial sequence
<220> FEATURE:
<223> OTHER INFORMATION: Cyclic peptide and D-peptide analogs

<400> SEQUENCE: 195

Cys Trp Leu Asp Ile Trp Cys
1               5

<210> SEQ ID NO 196
<211> LENGTH: 10
<212> TYPE: PRT
<213> ORGANISM: Artificial sequence
<220> FEATURE:
<223> OTHER INFORMATION: Cyclic peptide and D-peptide analogs

<400> SEQUENCE: 196

Cys Asn Gly Trp Thr Pro Asn Leu Asp Cys
1               5                   10

<210> SEQ ID NO 197
<211> LENGTH: 14
<212> TYPE: PRT
<213> ORGANISM: Artificial sequence
<220> FEATURE:
<223> OTHER INFORMATION: Cyclic peptide and D-peptide analogs

<400> SEQUENCE: 197

Cys Arg Ser Gln Asp Ile Asp Ala Asp Gly Gln Gly Phe Cys
1               5                   10

<210> SEQ ID NO 198
<211> LENGTH: 11
<212> TYPE: PRT
<213> ORGANISM: Artificial sequence
<220> FEATURE:
<223> OTHER INFORMATION: Linear peptide and D-peptide analogs

<400> SEQUENCE: 198

Met Asp Leu Ser Tyr Ser Met Lys Asp Leu
1               5                   10

<210> SEQ ID NO 199
<211> LENGTH: 7
<212> TYPE: PRT
<213> ORGANISM: Artificial sequence
<220> FEATURE:
<223> OTHER INFORMATION: Cyclic peptide and D-peptide analogs

<400> SEQUENCE: 199

Cys Leu Leu Asp Thr Gly Cys
```

```
1               5

<210> SEQ ID NO 200
<211> LENGTH: 14
<212> TYPE: PRT
<213> ORGANISM: Artificial sequence
<220> FEATURE:
<223> OTHER INFORMATION: Linear peptide and D-peptide analogs

<400> SEQUENCE: 200

His Leu Leu Val Phe Thr Thr Asp Ala Lys Thr His Ile Ala
1               5                   10

<210> SEQ ID NO 201
<211> LENGTH: 8
<212> TYPE: PRT
<213> ORGANISM: Artificial sequence
<220> FEATURE:
<223> OTHER INFORMATION: Cyclic peptide and D-peptide analogs

<400> SEQUENCE: 201

Cys Tyr Asp Met Lys Thr Thr Cys
1               5

<210> SEQ ID NO 202
<211> LENGTH: 13
<212> TYPE: PRT
<213> ORGANISM: Artificial sequence
<220> FEATURE:
<223> OTHER INFORMATION: Cyclic peptide and D-peptide analogs

<400> SEQUENCE: 202

Cys Leu Asn Asn Glu Val Ile Pro Gly Leu Lys Ser Cys
1               5                   10

<210> SEQ ID NO 203
<211> LENGTH: 25
<212> TYPE: PRT
<213> ORGANISM: Artificial sequence
<220> FEATURE:
<223> OTHER INFORMATION: Cyclic peptide and D-peptide analogs

<400> SEQUENCE: 203

Cys Cys Phe Ala Tyr Ile Ala Arg Pro Leu Pro Arg Ala His Ile Lys
1               5                   10                  15

Glu Tyr Phe Tyr Thr Ser Gly Lys Cys
            20                  25

<210> SEQ ID NO 204
<211> LENGTH: 41
<212> TYPE: PRT
<213> ORGANISM: Artificial sequence
<220> FEATURE:
<223> OTHER INFORMATION: Cyclic peptide and D-peptide analogs

<400> SEQUENCE: 204

Cys Cys Phe Ala Tyr Ile Ala Arg Pro Leu Pro Arg Ala His Ile Lys
1               5                   10                  15

Glu Tyr Phe Tyr Thr Ser Gly Lys Cys Ser Asn Pro Ala Val Val Phe
            20                  25                  30

Val Thr Arg Lys Asn Arg Gln Val Cys
            35                  40

<210> SEQ ID NO 205
<211> LENGTH: 7
```

```
<212> TYPE: PRT
<213> ORGANISM: Artificial sequence
<220> FEATURE:
<223> OTHER INFORMATION: Cyclic peptide and D-peptide analogs

<400> SEQUENCE: 205

Cys Ser Leu Leu Gly Ile Cys
1               5

<210> SEQ ID NO 206
<211> LENGTH: 12
<212> TYPE: PRT
<213> ORGANISM: Artificial sequence
<220> FEATURE:
<223> OTHER INFORMATION: Linear peptide and D-peptide analogs

<400> SEQUENCE: 206

Arg Phe Ile Val Val Val Lys Ala Thr Lys Ala Tyr
1               5                   10

<210> SEQ ID NO 207
<211> LENGTH: 14
<212> TYPE: PRT
<213> ORGANISM: Artificial sequence
<220> FEATURE:
<223> OTHER INFORMATION: Linear peptide and D-peptide analogs

<400> SEQUENCE: 207

Thr Trp Gly Lys Val Thr Ser Leu Leu Ile Trp Val Ile Ser
1               5                   10

<210> SEQ ID NO 208
<211> LENGTH: 12
<212> TYPE: PRT
<213> ORGANISM: Artificial sequence
<220> FEATURE:
<223> OTHER INFORMATION: Linear peptide and D-peptide analogs

<400> SEQUENCE: 208

Arg Arg Leu Arg Ile Met Thr Asn Ile Tyr Leu Leu
1               5                   10

<210> SEQ ID NO 209
<211> LENGTH: 13
<212> TYPE: PRT
<213> ORGANISM: Artificial sequence
<220> FEATURE:
<223> OTHER INFORMATION: Cyclic peptide and D-peptide analogs

<400> SEQUENCE: 209

Cys Asn Lys Cys Tyr Cys Lys Lys Cys Cys Tyr His Cys
1               5                   10

<210> SEQ ID NO 210
<211> LENGTH: 7
<212> TYPE: PRT
<213> ORGANISM: Artificial sequence
<220> FEATURE:
<223> OTHER INFORMATION: Cyclic peptide and D-peptide analogs

<400> SEQUENCE: 210

Cys Pro Arg Gly Asp Pro Cys
1               5

<210> SEQ ID NO 211
<211> LENGTH: 7
<212> TYPE: PRT
```

```
<213> ORGANISM: Artificial sequence
<220> FEATURE:
<223> OTHER INFORMATION: Cyclic peptide and D-peptide analogs

<400> SEQUENCE: 211

Cys Val Leu Asp Val Gly Cys
1               5

<210> SEQ ID NO 212
<211> LENGTH: 31
<212> TYPE: PRT
<213> ORGANISM: Artificial sequence
<220> FEATURE:
<223> OTHER INFORMATION: Cyclic peptide and D-peptide analogs

<400> SEQUENCE: 212

Cys Glu Thr Trp Arg Thr Glu Ala Pro Ser Ala Thr Gly Gln Ala Ser
1               5                   10                  15

Ser Leu Leu Gly Gly Arg Leu Leu Gly Gln Ser Ala Ala Ser Cys
            20                  25                  30

<210> SEQ ID NO 213
<211> LENGTH: 6
<212> TYPE: PRT
<213> ORGANISM: Artificial sequence
<220> FEATURE:
<223> OTHER INFORMATION: Cyclic peptide and D-peptide analogs

<400> SEQUENCE: 213

Cys Ser Val Thr Cys Gly
1               5

<210> SEQ ID NO 214
<211> LENGTH: 12
<212> TYPE: PRT
<213> ORGANISM: Artificial sequence
<220> FEATURE:
<223> OTHER INFORMATION: Cyclic peptide and D-peptide analogs

<400> SEQUENCE: 214

Cys Lys Asp Asn Lys Phe Asn Gly Lys Gly Pro Cys
1               5                   10

<210> SEQ ID NO 215
<211> LENGTH: 20
<212> TYPE: PRT
<213> ORGANISM: Artificial sequence
<220> FEATURE:
<223> OTHER INFORMATION: Linear peptide and D-peptide analogs

<400> SEQUENCE: 215

Gln His Leu Leu Gln Leu Thr Val Trp Gly Ile Lys Gln Leu Gln Ala
1               5                   10                  15

Arg Ile Leu Ala
            20

<210> SEQ ID NO 216
<211> LENGTH: 11
<212> TYPE: PRT
<213> ORGANISM: Artificial sequence
<220> FEATURE:
<223> OTHER INFORMATION: Linear peptide and D-peptide analogs

<400> SEQUENCE: 216

Asn Val Ser Tyr Ile Cys Ser Arg Tyr Tyr Arg
1               5                   10
```

<210> SEQ ID NO 217
<211> LENGTH: 10
<212> TYPE: PRT
<213> ORGANISM: Artificial sequence
<220> FEATURE:
<223> OTHER INFORMATION: Linear peptide and D-peptide analogs

<400> SEQUENCE: 217

His Arg Asp Ile Lys Pro Gln Asn Leu Leu
1               5                   10

<210> SEQ ID NO 218
<211> LENGTH: 7
<212> TYPE: PRT
<213> ORGANISM: Artificial sequence
<220> FEATURE:
<223> OTHER INFORMATION: Cyclic peptide and D-peptide analogs

<400> SEQUENCE: 218

Cys Arg Leu Leu Gly Gln Cys
1               5

<210> SEQ ID NO 219
<211> LENGTH: 10
<212> TYPE: PRT
<213> ORGANISM: Artificial sequence
<220> FEATURE:
<223> OTHER INFORMATION: Linear peptide and D-peptide analogs

<400> SEQUENCE: 219

Val Ile Gly Asn Gly Ser Phe Gly Val Val
1               5                   10

<210> SEQ ID NO 220
<211> LENGTH: 36
<212> TYPE: PRT
<213> ORGANISM: Artificial sequence
<220> FEATURE:
<223> OTHER INFORMATION: Cyclic peptide and D-peptide analogs

<400> SEQUENCE: 220

Cys Val Asn Ile Thr Ile Lys Gln His Thr Val Thr Thr Thr Thr Lys
1               5                   10                  15

Gly Glu Asn Phe Thr Glu Thr Asp Val Lys Met Met Glu Arg Val Val
            20                  25                  30

Glu Gln Met Cys
        35

<210> SEQ ID NO 221
<211> LENGTH: 12
<212> TYPE: PRT
<213> ORGANISM: Artificial sequence
<220> FEATURE:
<223> OTHER INFORMATION: Linear peptide and D-peptide analogs

<400> SEQUENCE: 221

Tyr Arg Gly Tyr Arg Gly Tyr Arg Gly Tyr Arg Gly
1               5                   10

<210> SEQ ID NO 222
<211> LENGTH: 8
<212> TYPE: PRT
<213> ORGANISM: Artificial sequence
<220> FEATURE:
<223> OTHER INFORMATION: Linear peptide and D-peptide analogs

```
<400> SEQUENCE: 222

Arg Tyr Arg Tyr Arg Tyr Arg Tyr
1               5

<210> SEQ ID NO 223
<211> LENGTH: 8
<212> TYPE: PRT
<213> ORGANISM: Artificial sequence
<220> FEATURE:
<223> OTHER INFORMATION: Linear peptide and D-peptide analogs

<400> SEQUENCE: 223

Glu Ala Tyr Glu Met Pro Ser Glu
1               5

<210> SEQ ID NO 224
<211> LENGTH: 12
<212> TYPE: PRT
<213> ORGANISM: Artificial sequence
<220> FEATURE:
<223> OTHER INFORMATION: Linear peptide and D-peptide analogs

<400> SEQUENCE: 224

Gly Val Val His Gly Val Ala Thr Val Ala Glu Lys
1               5                   10

<210> SEQ ID NO 225
<211> LENGTH: 17
<212> TYPE: PRT
<213> ORGANISM: Artificial sequence
<220> FEATURE:
<223> OTHER INFORMATION: Cyclic peptide and D-peptide analogs

<400> SEQUENCE: 225

Cys Pro Gly Ala Cys Val Cys Tyr Asn Glu Pro Lys Val Thr Thr Ser
1               5                   10                  15

Cys

<210> SEQ ID NO 226
<211> LENGTH: 10
<212> TYPE: PRT
<213> ORGANISM: Artificial sequence
<220> FEATURE:
<223> OTHER INFORMATION: Linear peptide and D-peptide analogs

<400> SEQUENCE: 226

Arg Asn Leu Thr Ile Leu Trp Leu His Ser
1               5                   10

<210> SEQ ID NO 227
<211> LENGTH: 8
<212> TYPE: PRT
<213> ORGANISM: Artificial sequence
<220> FEATURE:
<223> OTHER INFORMATION: Linear peptide and D-peptide analogs

<400> SEQUENCE: 227

Thr His Leu Phe Leu His Gly Asn
1               5

<210> SEQ ID NO 228
<211> LENGTH: 24
<212> TYPE: PRT
<213> ORGANISM: Artificial sequence
<220> FEATURE:
```

<223> OTHER INFORMATION: Cyclic peptide and D-peptide analogs

<400> SEQUENCE: 228

Cys Asp Cys Arg Ala Arg Pro Leu Trp Ala Trp Leu Gln Lys Phe Arg
1               5                   10                  15

Gly Ser Ser Ser Glu Val Pro Cys
            20

<210> SEQ ID NO 229
<211> LENGTH: 11
<212> TYPE: PRT
<213> ORGANISM: Artificial sequence
<220> FEATURE:
<223> OTHER INFORMATION: Linear peptide and D-peptide analogs

<400> SEQUENCE: 229

Phe Leu Gly Ala Ala Gly Ser Thr Met Gly Ala
1               5                   10

<210> SEQ ID NO 230
<211> LENGTH: 11
<212> TYPE: PRT
<213> ORGANISM: Artificial sequence
<220> FEATURE:
<223> OTHER INFORMATION: Linear peptide and D-peptide analogs

<400> SEQUENCE: 230

Phe Leu Leu Lys Leu Ala Gly Arg Trp Pro Val
1               5                   10

<210> SEQ ID NO 231
<211> LENGTH: 9
<212> TYPE: PRT
<213> ORGANISM: Artificial sequence
<220> FEATURE:
<223> OTHER INFORMATION: Linear peptide and D-peptide analogs

<400> SEQUENCE: 231

Ile Val Gly Ala Glu Thr Phe Tyr Val
1               5

<210> SEQ ID NO 232
<211> LENGTH: 11
<212> TYPE: PRT
<213> ORGANISM: Artificial sequence
<220> FEATURE:
<223> OTHER INFORMATION: Linear peptide and D-peptide analogs

<400> SEQUENCE: 232

Ala Leu Leu Asp Thr Gly Ala Asp Asp Thr Val
1               5                   10

<210> SEQ ID NO 233
<211> LENGTH: 16
<212> TYPE: PRT
<213> ORGANISM: Artificial sequence
<220> FEATURE:
<223> OTHER INFORMATION: Linear peptide and D-peptide analogs

<400> SEQUENCE: 233

Ala His Lys Leu Gly Ser Gly Ala Tyr Gly Glu Val Leu Leu Cys Arg
1               5                   10                  15

<210> SEQ ID NO 234
<211> LENGTH: 12
<212> TYPE: PRT

```
<213> ORGANISM: Artificial sequence
<220> FEATURE:
<223> OTHER INFORMATION: Linear peptide and D-peptide analogs

<400> SEQUENCE: 234

Lys Leu Arg Asp Arg Leu Gly Thr Ala Tyr Tyr Ile
1               5                   10

<210> SEQ ID NO 235
<211> LENGTH: 10
<212> TYPE: PRT
<213> ORGANISM: Artificial sequence
<220> FEATURE:
<223> OTHER INFORMATION: Linear peptide and D-peptide analogs

<400> SEQUENCE: 235

Arg Leu Arg Asp Ala Phe Asn Leu Phe Asp
1               5                   10

<210> SEQ ID NO 236
<211> LENGTH: 22
<212> TYPE: PRT
<213> ORGANISM: Artificial sequence
<220> FEATURE:
<223> OTHER INFORMATION: Linear peptide and D-peptide analogs

<400> SEQUENCE: 236

Asn Lys Ala Val Met Asp Leu Lys Tyr His Leu Gln Lys Val Tyr Ala
1               5                   10                  15

Asn Tyr Leu Ser Gln Glu
            20

<210> SEQ ID NO 237
<211> LENGTH: 11
<212> TYPE: PRT
<213> ORGANISM: Artificial sequence
<220> FEATURE:
<223> OTHER INFORMATION: Linear peptide and D-peptide analogs

<400> SEQUENCE: 237

Phe Ile Ile Gly Gly Ser Val Val Tyr Gln Glu
1               5                   10

<210> SEQ ID NO 238
<211> LENGTH: 10
<212> TYPE: PRT
<213> ORGANISM: Artificial sequence
<220> FEATURE:
<223> OTHER INFORMATION: Cyclic peptide and D-peptide analogs

<400> SEQUENCE: 238

Cys Asn Ser Leu Asp Met Lys Tyr Phe Cys
1               5                   10

<210> SEQ ID NO 239
<211> LENGTH: 13
<212> TYPE: PRT
<213> ORGANISM: Artificial sequence
<220> FEATURE:
<223> OTHER INFORMATION: Linear peptide and D-peptide analogs

<400> SEQUENCE: 239

Ser Trp Glu Ser Ile Pro Lys Lys Phe Lys Pro Leu Ser
1               5                   10

<210> SEQ ID NO 240
```

```
<211> LENGTH: 20
<212> TYPE: PRT
<213> ORGANISM: Artificial sequence
<220> FEATURE:
<223> OTHER INFORMATION: Cyclic peptide and D-peptide analogs

<400> SEQUENCE: 240

Cys Cys Phe Cys Leu Pro Gly Gly Gly Gly Val Cys Cys Leu Cys Ser
1               5                   10                  15

Glu Cys Ile Cys
            20

<210> SEQ ID NO 241
<211> LENGTH: 20
<212> TYPE: PRT
<213> ORGANISM: Artificial sequence
<220> FEATURE:
<223> OTHER INFORMATION: Linear peptide and D-peptide analogs

<400> SEQUENCE: 241

Arg Ala Leu Gln Val Val Arg Ala Arg Lys Gln Ile Val Ala Gly Val
1               5                   10                  15

Asn Tyr Phe Leu
            20

<210> SEQ ID NO 242
<211> LENGTH: 15
<212> TYPE: PRT
<213> ORGANISM: Artificial sequence
<220> FEATURE:
<223> OTHER INFORMATION: Cyclic peptide and D-peptide analogs

<400> SEQUENCE: 242

Cys Val Lys Gln Cys Cys Val Cys Cys Lys Gly Lys Asn Gly Cys
1               5                   10                  15

<210> SEQ ID NO 243
<211> LENGTH: 21
<212> TYPE: PRT
<213> ORGANISM: Artificial sequence
<220> FEATURE:
<223> OTHER INFORMATION: Cyclic peptide and D-peptide analogs

<400> SEQUENCE: 243

Cys Arg Gln Val Cys Pro Lys Ala Thr Arg Phe Val Cys Val Cys Cys
1               5                   10                  15

Lys Lys Ser Asp Cys
            20

<210> SEQ ID NO 244
<211> LENGTH: 17
<212> TYPE: PRT
<213> ORGANISM: Artificial sequence
<220> FEATURE:
<223> OTHER INFORMATION: Cyclic peptide and D-peptide analogs

<400> SEQUENCE: 244

Cys Arg Asp Asp Ser Glu Cys Ile Thr Arg Leu Cys Arg Lys Arg Arg
1               5                   10                  15

Cys

<210> SEQ ID NO 245
<211> LENGTH: 18
<212> TYPE: PRT
<213> ORGANISM: Artificial sequence
```

```
<220> FEATURE:
<223> OTHER INFORMATION: Cyclic peptide and D-peptide analogs

<400> SEQUENCE: 245

Arg Cys Ile Cys Thr Arg Gly Phe Cys Arg Cys Leu Cys Arg Arg Gly
1               5                   10                  15

Val Cys

<210> SEQ ID NO 246
<211> LENGTH: 18
<212> TYPE: PRT
<213> ORGANISM: Artificial sequence
<220> FEATURE:
<223> OTHER INFORMATION: Cyclic peptide and D-peptide analogs

<400> SEQUENCE: 246

Arg Cys Ile Cys Gly Arg Gly Ile Cys Arg Cys Ile Cys Gly Arg Gly
1               5                   10                  15

Ile Cys

<210> SEQ ID NO 247
<211> LENGTH: 15
<212> TYPE: PRT
<213> ORGANISM: Artificial sequence
<220> FEATURE:
<223> OTHER INFORMATION: Linear peptide and D-peptide analogs

<400> SEQUENCE: 247

Leu Ala Ala Arg Trp Ala Ala Lys Glu Ala Val Lys Ala Trp Ser
1               5                   10                  15

<210> SEQ ID NO 248
<211> LENGTH: 12
<212> TYPE: PRT
<213> ORGANISM: Artificial sequence
<220> FEATURE:
<223> OTHER INFORMATION: Linear peptide and D-peptide analogs

<400> SEQUENCE: 248

Val Pro Thr Met Gly Ala Leu His Glu Gly His Leu
1               5                   10

<210> SEQ ID NO 249
<211> LENGTH: 9
<212> TYPE: PRT
<213> ORGANISM: Artificial sequence
<220> FEATURE:
<223> OTHER INFORMATION: Linear peptide and D-peptide analogs

<400> SEQUENCE: 249

Ala Gly Val Leu Thr Val Val Leu Lys
1               5

<210> SEQ ID NO 250
<211> LENGTH: 12
<212> TYPE: PRT
<213> ORGANISM: Artificial sequence
<220> FEATURE:
<223> OTHER INFORMATION: Cyclic peptide and D-peptide analogs

<400> SEQUENCE: 250

Cys Phe Phe Gly Glu Lys Asp Tyr Gln Gln Leu Cys
1               5                   10

<210> SEQ ID NO 251
```

```
<211> LENGTH: 13
<212> TYPE: PRT
<213> ORGANISM: Artificial sequence
<220> FEATURE:
<223> OTHER INFORMATION: Cyclic peptide and D-peptide analogs

<400> SEQUENCE: 251

Met Lys Glu Val Leu Phe Tyr Leu Gly Gln Tyr Ile Met
1               5                   10

<210> SEQ ID NO 252
<211> LENGTH: 11
<212> TYPE: PRT
<213> ORGANISM: Artificial sequence
<220> FEATURE:
<223> OTHER INFORMATION: Cyclic peptide and D-peptide analogs

<400> SEQUENCE: 252

Cys Ala Glu Tyr Trp Ala Leu Leu Ser Pro Cys
1               5                   10

<210> SEQ ID NO 253
<211> LENGTH: 13
<212> TYPE: PRT
<213> ORGANISM: Artificial sequence
<220> FEATURE:
<223> OTHER INFORMATION: Cyclic peptide and D-peptide analogs

<400> SEQUENCE: 253

Cys Leu Thr Phe Glu His Trp Trp Ala Gln Leu Thr Cys
1               5                   10

<210> SEQ ID NO 254
<211> LENGTH: 7
<212> TYPE: PRT
<213> ORGANISM: Artificial sequence
<220> FEATURE:
<223> OTHER INFORMATION: Cyclic peptide and D-peptide analogs

<400> SEQUENCE: 254

Lys Pro His Ser Cys Asn Ala
1               5

<210> SEQ ID NO 255
<211> LENGTH: 13
<212> TYPE: PRT
<213> ORGANISM: Artificial sequence
<220> FEATURE:
<223> OTHER INFORMATION: Cyclic peptide and D-peptide analogs

<400> SEQUENCE: 255

Cys Asp Phe Lys Leu Ala Val Tyr Ile Lys Tyr Arg Cys
1               5                   10

<210> SEQ ID NO 256
<211> LENGTH: 12
<212> TYPE: PRT
<213> ORGANISM: Artificial sequence
<220> FEATURE:
<223> OTHER INFORMATION: Cyclic peptide and D-peptide analogs

<400> SEQUENCE: 256

Cys Lys Asn Phe Phe Trp Lys Thr Phe Thr Ser Cys
1               5                   10

<210> SEQ ID NO 257
<211> LENGTH: 6
```

```
<212> TYPE: PRT
<213> ORGANISM: Artificial sequence
<220> FEATURE:
<223> OTHER INFORMATION: Cyclic peptide and D-peptide analogs

<400> SEQUENCE: 257

Cys Phe Trp Lys Thr Cys
1               5
```